US010605725B2

(12) United States Patent
Mallery et al.

(10) Patent No.: US 10,605,725 B2
(45) Date of Patent: Mar. 31, 2020

(54) WINDOW OBSCURATION SENSORS FOR MOBILE GAS AND CHEMICAL IMAGING CAMERAS

(71) Applicant: REBELLION PHOTONICS, INC., Houston, TX (US)

(72) Inventors: Ryan Mallery, Houston, TX (US); Ohad Israel Balila, Friendswood, TX (US); Robert Timothy Kester, Friendswood, TX (US)

(73) Assignee: REBELLION PHOTONICS, INC., Houston, TX (US)

( * ) Notice: Subject to any disclaimer, the term of this patent is extended or adjusted under 35 U.S.C. 154(b) by 0 days.

(21) Appl. No.: 16/185,399

(22) Filed: Nov. 9, 2018

(65) Prior Publication Data

US 2019/0137388 A1 May 9, 2019

Related U.S. Application Data

(60) Provisional application No. 62/584,684, filed on Nov. 10, 2017, provisional application No. 62/584,076, filed on Nov. 9, 2017.

(51) Int. Cl.
*G01N 21/3504* (2014.01)
*H04N 5/33* (2006.01)
(Continued)

(52) U.S. Cl.
CPC ........ *G01N 21/3504* (2013.01); *G01J 5/0806* (2013.01); *G01N 21/314* (2013.01); *H04N 5/33* (2013.01)

(58) Field of Classification Search
CPC ........... G01N 15/1434; G01N 21/3504; G01N 21/314; H04N 5/33; G01J 5/0806
See application file for complete search history.

(56) References Cited

U.S. PATENT DOCUMENTS 3,841,763 A   10/1974 Lewis
3,849,005 A   11/1974 Girard et al.
(Continued)

FOREIGN PATENT DOCUMENTS

CA   2 365 866   9/2000
CA   2 787 303   7/2011
(Continued)

OTHER PUBLICATIONS

US 10,113,914 B2, 10/2018, Kester et al. (withdrawn)
(Continued)

*Primary Examiner* — David P Porta
*Assistant Examiner* — Fani Boosalis
(74) *Attorney, Agent, or Firm* — Knobbe, Martens, Olson & Bear, LLP

(57) ABSTRACT

An infrared (IR) imaging system for determining a concentration of a target species in an object is disclosed. The imaging system can include an optical system including a focal plane array (FPA) unit behind an optical window. The optical system can have components defining at least two optical channels thereof, said at least two optical channels being spatially and spectrally different from one another. Each of the at least two optical channels can be positioned to transfer IR radiation incident on the optical system towards the optical FPA. The system can include a processing unit containing a processor that can be configured to acquire multispectral optical data representing said target species from the IR radiation received at the optical FPA. One or more of the optical channels may be used in detecting objects on or near the optical window, to avoid false detections of said target species.

19 Claims, 36 Drawing Sheets

(51) Int. Cl.
*G01J 5/08* (2006.01)
*G01N 21/31* (2006.01)

(56) References Cited

U.S. PATENT DOCUMENTS

| | | |
|---|---|---|
| 4,134,683 A | 1/1979 | Goetz et al. |
| 4,390,785 A | 6/1983 | Faulhaber et al. |
| 4,464,789 A | 8/1984 | Sternberg |
| 4,933,555 A | 6/1990 | Smith |
| 4,963,963 A | 10/1990 | Dorman |
| 4,965,448 A | 10/1990 | Morse et al. |
| 5,127,742 A | 7/1992 | Fraden |
| 5,136,421 A | 8/1992 | Sagan |
| 5,157,258 A | 10/1992 | Gunning, III et al. |
| 5,354,987 A | 10/1994 | MacPherson |
| 5,550,373 A | 8/1996 | Cole et al. |
| 5,559,336 A | 9/1996 | Kosai et al. |
| 5,604,346 A | 2/1997 | Hamrelius et al. |
| 5,822,222 A | 10/1998 | Kaplinsky et al. |
| 5,877,500 A | 3/1999 | Braig et al. |
| 5,920,066 A | 7/1999 | DiRenzo et al. |
| 5,926,283 A | 7/1999 | Hopkins |
| 5,973,844 A | 10/1999 | Burger |
| 5,994,701 A | 11/1999 | Tsuchimoto et al. |
| 6,023,061 A | 2/2000 | Bodkin |
| 6,097,034 A * | 8/2000 | Weckstrom .......... A61B 5/0836 250/343 |
| 6,184,529 B1 | 2/2001 | Contini |
| 6,268,883 B1 | 7/2001 | Zehnder et al. |
| 6,456,261 B1 | 9/2002 | Zhang |
| 6,465,785 B1 | 10/2002 | McManus |
| 6,556,853 B1 | 4/2003 | Cabib et al. |
| 6,680,778 B2 | 1/2004 | Hinnrichs et al. |
| 6,700,527 B1 | 3/2004 | Martin et al. |
| 7,109,488 B2 | 9/2006 | Milton |
| 7,119,337 B1 | 10/2006 | Johnson et al. |
| 7,242,478 B1 | 7/2007 | Dombrowski et al. |
| 7,315,377 B2 | 1/2008 | Holland et al. |
| 7,321,119 B2 | 1/2008 | King |
| 7,364,697 B2 | 4/2008 | McFarland et al. |
| 7,433,042 B1 | 10/2008 | Cavanaugh et al. |
| 7,606,484 B1 | 10/2009 | Richards et al. |
| 7,634,157 B1 | 12/2009 | Richards et al. |
| 7,750,802 B1 | 7/2010 | Parish et al. |
| 7,835,002 B2 | 11/2010 | Muhammed et al. |
| 7,888,624 B1 | 2/2011 | Murguia et al. |
| 8,027,041 B1 | 9/2011 | Mitchell et al. |
| 8,153,980 B1 | 4/2012 | Brady et al. |
| 8,159,568 B2 | 4/2012 | Ahdoot |
| 8,212,213 B2 | 7/2012 | Myrick et al. |
| 8,373,757 B1 | 2/2013 | Nguyen |
| 8,629,930 B2 | 1/2014 | Brueckner et al. |
| 8,653,461 B1 | 2/2014 | Benson et al. |
| 8,654,328 B2 | 2/2014 | Tkaczyk et al. |
| 8,686,364 B1 | 4/2014 | Little et al. |
| 9,225,913 B2 | 12/2015 | Ekdahl |
| 9,395,516 B2 | 7/2016 | Katsunuma et al. |
| 9,562,849 B2 | 2/2017 | Kester et al. |
| 9,599,508 B2 | 3/2017 | Kester et al. |
| 9,625,318 B2 | 4/2017 | Kester et al. |
| 9,641,772 B2 | 5/2017 | Yujiri |
| 9,644,562 B2 | 5/2017 | Fujita |
| 9,756,263 B2 | 9/2017 | Kester et al. |
| 9,823,231 B1 | 11/2017 | Steele et al. |
| 10,084,975 B2 | 9/2018 | Kester et al. |
| 10,254,166 B2 | 4/2019 | Kester et al. |
| 10,267,686 B2 | 4/2019 | Kester et al. |
| 10,375,327 B2 | 8/2019 | Kester |
| 10,444,070 B2 | 10/2019 | Kester et al. |
| 10,458,905 B2 | 10/2019 | Kester et al. |
| 2001/0040216 A1 | 11/2001 | Knauth et al. |
| 2002/0015151 A1 | 2/2002 | Gorin |
| 2002/0121370 A1 | 9/2002 | Kurigian et al. |
| 2002/0159101 A1 | 10/2002 | Alderson et al. |
| 2003/0102435 A1 | 6/2003 | Myers et al. |
| 2003/0134426 A1 | 7/2003 | Jiang et al. |
| 2003/0183756 A1 | 10/2003 | Huniu |
| 2004/0093167 A1 | 5/2004 | Braig et al. |
| 2004/0111232 A1 | 6/2004 | Butler et al. |
| 2004/0252300 A1 | 12/2004 | Slater |
| 2005/0029453 A1 | 2/2005 | Allen et al. |
| 2005/0057366 A1 | 3/2005 | Kadwell et al. |
| 2005/0103989 A1 | 5/2005 | Watson et al. |
| 2006/0044562 A1 | 3/2006 | Hagene et al. |
| 2006/0183241 A1 | 8/2006 | Lehmann et al. |
| 2006/0203248 A1 | 9/2006 | Reichardt et al. |
| 2006/0232675 A1 | 10/2006 | Chamberlain et al. |
| 2006/0279632 A1 | 12/2006 | Anderson |
| 2007/0018105 A1 | 1/2007 | Grimberg |
| 2007/0075888 A1 | 4/2007 | Kelly et al. |
| 2007/0108385 A1 | 5/2007 | Mantese et al. |
| 2007/0170359 A1 | 7/2007 | Syllaios et al. |
| 2007/0170363 A1 | 7/2007 | Schimert et al. |
| 2008/0170140 A1 | 7/2008 | Silver et al. |
| 2008/0204744 A1 | 8/2008 | Mir et al. |
| 2008/0231719 A1 | 9/2008 | Benson et al. |
| 2008/0251724 A1 | 10/2008 | Baliga et al. |
| 2009/0015824 A1 | 1/2009 | Shubinsky et al. |
| 2009/0252650 A1 | 10/2009 | Lakshmanan |
| 2010/0162206 A1 | 6/2010 | Roth et al. |
| 2010/0171866 A1 | 7/2010 | Brady et al. |
| 2010/0211333 A1 | 8/2010 | Pruet et al. |
| 2010/0309467 A1 | 12/2010 | Fox et al. |
| 2011/0176577 A1 | 7/2011 | Bandara et al. |
| 2011/0185048 A1 | 7/2011 | Yew et al. |
| 2011/0261321 A1 | 10/2011 | Ramella-Roman et al. |
| 2011/0271738 A1 | 11/2011 | McGill et al. |
| 2012/0273680 A1 | 11/2012 | Furry |
| 2013/0181836 A1 | 7/2013 | Cardoso et al. |
| 2013/0206990 A1 | 8/2013 | Hsu et al. |
| 2013/0228887 A1 | 9/2013 | Wehner et al. |
| 2013/0235256 A1 | 9/2013 | Kodama |
| 2013/0250124 A1 | 9/2013 | Furry |
| 2013/0307991 A1 | 11/2013 | Olsen et al. |
| 2013/0321806 A1 | 12/2013 | Kester et al. |
| 2013/0341509 A1 | 12/2013 | Nelson et al. |
| 2013/0342680 A1 | 12/2013 | Zeng et al. |
| 2014/0002639 A1 | 1/2014 | Cheben et al. |
| 2014/0139643 A1* | 5/2014 | Hogasten .......... H01L 27/14609 348/48 |
| 2014/0320843 A1 | 10/2014 | Streuber et al. |
| 2015/0138534 A1 | 5/2015 | Tidhar |
| 2015/0144770 A1 | 5/2015 | Choi |
| 2015/0226613 A1 | 8/2015 | Bauer et al. |
| 2015/0288894 A1 | 10/2015 | Geelen et al. |
| 2015/0292948 A1* | 10/2015 | Goldring .............. G01N 21/255 356/326 |
| 2015/0316473 A1 | 11/2015 | Kester et al. |
| 2016/0037089 A1 | 2/2016 | Silny et al. |
| 2016/0041095 A1 | 2/2016 | Rothberg et al. |
| 2016/0097713 A1 | 4/2016 | Kester et al. |
| 2016/0097714 A1 | 4/2016 | Zeng et al. |
| 2016/0238454 A1 | 8/2016 | Pillans |
| 2016/0245698 A1 | 8/2016 | Pau et al. |
| 2016/0313181 A1 | 10/2016 | Golub et al. |
| 2016/0349228 A1 | 12/2016 | Kester et al. |
| 2016/0356702 A1 | 12/2016 | Hinnrichs |
| 2016/0380014 A1 | 12/2016 | Ganapathi et al. |
| 2017/0026588 A1 | 1/2017 | Kester et al. |
| 2017/0089761 A1 | 3/2017 | McQuilkin et al. |
| 2017/0138918 A1 | 5/2017 | Bardoni |
| 2017/0234761 A1 | 8/2017 | Augusto |
| 2017/0248517 A1 | 8/2017 | Scherer et al. |
| 2017/0347037 A1 | 11/2017 | Hall et al. |
| 2017/0350758 A1 | 12/2017 | Kester et al. |
| 2017/0356802 A1 | 12/2017 | Kester et al. |
| 2018/0039885 A1 | 2/2018 | Albrecht et al. |
| 2018/0188163 A1 | 7/2018 | Kester et al. |
| 2018/0191967 A1 | 7/2018 | Kester |
| 2019/0003984 A1 | 1/2019 | Kester et al. |

(56) References Cited

U.S. PATENT DOCUMENTS

| | | |
|---|---|---|
| 2019/0273875 A1 | 9/2019 | Kester et al. |
| 2019/0373185 A1 | 12/2019 | Kester |

FOREIGN PATENT DOCUMENTS

| | | |
|---|---|---|
| EP | 0 837 600 | 4/1998 |
| EP | 2 871 452 | 5/2015 |
| EP | 2 955 496 | 12/2015 |
| EP | 3 040 706 | 7/2016 |
| GB | 1014769 | 12/1965 |
| GB | 2518224 | 3/2015 |
| JP | 2013-128185 | 6/2013 |
| WO | WO 2004/097389 | 11/2004 |
| WO | WO 2007/008826 | 1/2007 |
| WO | WO 2008/109183 | 9/2008 |
| WO | WO 2009/094782 | 8/2009 |
| WO | WO 2010/053979 | 5/2010 |
| WO | WO 2012/078417 | 6/2012 |
| WO | WO 2012/082366 | 6/2012 |
| WO | WO 2013/173541 | 11/2013 |
| WO | WO 2015/108236 | 7/2015 |
| WO | WO 2016/196224 | 12/2016 |
| WO | WO 2017/201194 | 11/2017 |
| WO | WO 2018/075957 | 4/2018 |
| WO | WO 2018/075964 | 4/2018 |
| WO | WO 2018/156795 | 8/2018 |
| WO | WO 2019/094639 | 5/2019 |

OTHER PUBLICATIONS

Adams, et al., "Advances in Detectors: Hot IR sensors improve IR camera size, weight, and power", Laser Focus World, vol. 50, Issue 01, Jan. 17, 2014, 6 pages. Also available at http://www.ircameras.com/articles/advances-detectors-hot-ir-sensors-improve-ir-camera-size-weight-power/.
Allen et al., "Measurements of Methane Emissions at Natural Gas Production Sites in the United States", PNAS, Oct. 29, 2013, vol. 110, No. 44, pp. 7.
Alvarez et al., "Greater Focus Needed on Methane Leakage from Natural Gas Infrastructure", PNAS, Apr. 24, 2012, vol. 109, No. 17, pp. 12.
Bedard et al., "Image Mapping Spectrometry: Calibration and Characterization", Optical Engineering, Nov. 2012, vol. 51, No. 11, pp. 111711-1-111711-13.
Ben-David et al., "Probability Theory for 3-Layer Remote Sensing Radiative Transfer Model: Univariate Case," Optics Express, Apr. 2012, vol. 20, No. 9, pp. 10004-10033.
Ben-David et al., "Probability Theory for 3-Layer Remote Sensing Radiative Transfer Model: Errata," Optics Express, May 20, 2013, vol. 21, No. 10, pp. 11852.
Brady et al., "Multiscale Lens Design", Optics Express, Jun. 22, 2009, vol. 17, No. 13, pp. 10659-10674.
Brochure provided by Lofty Designs to Rebellion Photonics on Oct. 31, 2012 as noted from the email. Subsequent to that date brochure was used in connection with potential customers.
Caulton et al., "Toward a Better Understanding and Quantification of Methane Emissions from Shale Gas Development", PNAS, Apr. 29, 2014, vol. 111, No. 17, pp. 7.
Chen et al., "Quantitative Sectioning and Noise Analysis for Structured Illumination Microscopy: Erratum", Optics Express, Oct. 19, 2015, vol. 23, No. 21, pp. 27633-27634.
Chidley et al., "Flow-Induced Birefringence: The Hidden PSF Killer in High Performance Injection-Molded Plastic Optics", Endoscopic Microscopy, Proceedings of SPIE vol. 6082, 2006, pp. 11.
Chu et al., The NIST Quantitative Infrared Database, Journal of Research of the National Institute of Standards and Technology, Jan.-Feb. 1999, vol. 104, No. 1, pp. 59-81.
Cossel et al., "Analysis of Trace Impurities in Semiconductor Gas via Cavity-Enhanced Direct Frequency Comb Spectroscopy", Applied Physics B, Sep. 2010, vol. 100, No. 4, pp. 917-924.

DiPietro et al., "Hyperspectral Matched Filter with False-Alarm Mitigation", Optical Engineering, Jan. 2012, vol. 51, No. 1, pp. 016202-1-016202-7.
"Directed Inspection and Maintenance at Gas Processing Plants and Booster Stations," United States Environmental Protection Agency Air and Radiation (6202J), EPA430-B-03-018, Oct. 2003 available at https://www3.epa.gov/gasstar/documents/ll_dimgasproc.pdf.
Eriksson et al., "Radiative Cooling Computed for Model Atmospheres", Applied Optics, Dec. 1, 1982, vol. 21, No. 23, pp. 4381-4388.
Flanigan, "Detection of Organic Vapors with Active and Passive Sensors: A Comparison," Applied Optics, 1986, vol. 25, No. 23, pp. 4253-4260.
Gålfalk et al., "Making Methane Visible", Nature Climate Change, Apr. 2016, vol. 6, pp. 426-430.
Gålfalk et al., "Making Methane Visible", Supplementary Information, Nature Climate Change, 2015, pp. 1-14.
Gallagher et al., "Error Analysis for Estimation of Trace Vapor Concentration Pathlength in Stack Plumes", Applied Spectroscopy, 2003, vol. 57, No. 6, pp. 614-621.
Gallagher et al., "Estimation of Trace Vapor Concentration-Pathlength in Plumes for Remote Sensing Applications from Hyperspectral Images", Analytica Chimica Acta, 2003, vol. 490, pp. 139-152.
Gao et al., "Compact Image Slicing Spectrometer (ISS) for Hyperspectral Fluorescence Microscopy", Optics Express, Jul. 20, 2009, vol. 17, No. 15, pp. 12293-12308.
Gao et al., "Depth-Resolved Image Mapping Spectrometer (IMS) with Structured Illumination", Optics Express, Aug. 29, 2011, vol. 19, No. 18, pp. 17439-17452.
Gao et al., "Optical Design of a Snapshot High-Sampling Image Mapping Spectrometer (IMS) for Hyperspectral Microscopy", Three-Dimensional and Multidimensional Microscopy: Image Acquisition and Processing XVII, Proceedings of SPIE vol. 7570, 2010, pp. 1-7.
Gao et al., "Quantitative Comparison Between Full-Spectrum and Filter-Based Imaging in Hyperspectral Fluorescence Microscopy", Journal of Microscopy, 2012, vol. 246, No. 2, pp. 113-123.
Gao et al., "Snapshot Image-Mapping Spectrometer for Hyperspectral Fluorescence Microscopy", Optics and Photonics News, Nov. 2010, vol. 21, No. 12, p. 50.
Gao et al., "Snapshot Image Mapping Spectrometer (IMS) with High Sampling Density for Hyperspectral Microscopy", Optics Express, Jul. 5, 2010, vol. 18, No. 4, pp. 14330-14344.
Gerhart et al., "Detection and Tracking of Gas Plumes in LWIR Hyperspectral Video Sequence Data," Algorithms and Technologies for Multispectral, Hyperspectral, and Ultraspectral Imagery XIX, 2013, SPIE Proceedings vol. 8743, pp. 1-14.
Gittins, Christopher M., "Detection and Characterization of Chemical Vapor Fugitive Emissions by Nonlinear Optimal Estimation: Theory and Simulation", Applied Optics, Aug. 10, 2009, vol. 48, No. 23, pp. 4545-4561.
Goldberg et al., "Dual Band MWIR/LWIR Focal Plane Array Test Results," Army Research Lab, Adelphi, MD, Aug. 1999, pp. 18.
Golowich et al., "Performance Limits of LWIR Gaseous Plume Quantification", Algorithms and Technologies for Multispectral, Hyperspectral, and Ultraspectral Imagery XVII, 2011, Proceedings of SPIE vol. 8048, pp. 1-12.
Griffin et al., "The Herschel—SPIRE 1-15 Instrument and its In-Flight Performance," Astronomy and Astrophysics, Jul. 1, 2010, vol. 518, pp. 7.
Gross et al., "Remote Identification and Quantification of Industrial Smokestack Effluents via Imaging Fourier-Transform Spectroscopy", Environmental Science & Technology, 2010, vol. 44, No. 24, pp. 9390-9397.
Gupta et al., "Miniature Snapshot Multispectral Imager," Optical Engineering, 2011, vol. 50, pp. 033203-1-033203-9.
Hadlington, Simon, "New Camera Makes Methane Visible", Chemistry World, http://web.archive.org/web/20160305234907/http://www.rsc.org/chemistryworld/2015/12/methane-camera-infrared-greenhouse-gas, Dec. 14, 2015, pp. 2.
Hagen et al., "Analysis of Computed Tomographic Imaging Spectrometers. I. Spatial and Spectral Resolution", Applied Optics, Oct. 1, 2008, vol. 47, No. 28, pp. F85-F95.

(56) References Cited

OTHER PUBLICATIONS

Hagen et al., "Coded Aperture DUV Spectrometer for Standoff Raman Spectroscopy", Next-Generation Spectroscopic Technologies II, Proceedings of SPIE vol. 7319, 2009, pp. 1-10.
Hagen et al., "Compound Prism Design Principles, I", Applied Optics, Sep. 1, 2011, vol. 50, No. 25, pp. 4998-5011.
Hagen et al., "Compound Prism Design Principles, II: Triplet and Janssen Prisms", Applied Optics, Sep. 1, 2011, vol. 50, No. 25, pp. 5012-5022.
Hagen et al., "Compound Prism Design Principles, III: Linear-in-Wavenumber and Optical Coherence Tomography Prisms", Applied Optics, Sep. 1, 2011, vol. 50, No. 25, pp. 5023-5030.
Hagen et al., "Fourier Methods of Improving Reconstruction Speed for CTIS Imaging Spectrometers", Imaging Spectrometry XII, Proceedings of SPIE vol. 6661, 2007, pp. 11.
Hagen et al., "Foveated Endoscopic Lens", Journal of Biomedical Optics, Feb. 2012, vol. 17, No. 2, pp. 021104-1-021104-6.
Hagen et al., "Gaussian Profile Estimation in One Dimension", Applied Optics, Aug. 1, 2007, vol. 46, No. 22, pp. 5374-5383.
Hagen et al., "Gaussian Profile Estimation in Two Dimensions", Applied Optics, Dec. 20, 2008, vol. 47, No. 36, pp. 6842-6851.
Hagen et al., "Quantitative Sectioning and Noise Analysis for Structured Illumination Microscopy", Optics Express, Jan. 2, 2012, vol. 20, No. 1, pp. 403-413.
Hagen et al., "Quantitative Sectioning and Noise Analysis for Structured Illumination Microscopy: Errata", Optics Express, Feb. 27, 2012, vol. 20, No. 5, pp. 5343.
Hagen et al., "Real-Time Quantitative Hydrocarbon Gas Imaging with the Gas Cloud Imager (GCI)", Proceedings of SPIE, vol. 8358, Chemical, Biological, Radiological, Nuclear, and Explosives (CBRNE) Sensing XIII, May 1, 2012, pp. 7.
Hagen et al., "Review of Snapshot Spectral Imaging Technologies", Optical Engineering, Sep. 2013, vol. 52, No. 9, pp. 090901-1-090901-23.
Hagen et al., "Snapshot Advantage: A Review of the Light Collection Improvement for Parallel High-Dimensional Measurement Systems," Optical Engineering, Jun. 13, 2012, vol. 51, No. 11, p. 111702-1-111702-7.
Hagen et al., "Snapshot Mueller Matrix Spectropolarimeter" Optics Letters, Aug. 1, 2007, vol. 32, No. 15, pp. 2100-2102.
Hagen et al., "Spectrally-Resolved Imaging of Dynamic Turbid Media", Multimodal Biomedical Imaging VI, Proceedings of SPIE vol. 7892, 2011, pp. 1-7.
Hagen et al., "Video-Rate Spectral Imaging of Gas Leaks in the Longwave Infrared," Chemical, Biological, Radiological, Nuclear, and Explosives (CBRNE) Sensing XIV, May 29, 2013, SPIE Proceedings vol. 8710, pp. 7.
Harley et al., "Remote Quantification of Smokestack Effluent Mass Flow Rates Using Imaging Fourier Transform Spectrometry," Chemical, Biological, Radiological, Nuclear, and Explosives (CBRNE) Sensing XII, Apr. 25-29, 2011, SPIE Proceedings vol. 8018, pp. 1-13.
Hayden et al., "Determination of Trace-Gas Amounts in Plumes by the Use of Orthogonal Digital Filtering of Thermal-Emission Spectra", Applied Optics, Jun. 1, 1996, vol. 35, No. 16, pp. 2802-2809.
Hirsch et al., "Detection of Gaseous Plumes in IR Hyperspectral Images Using Hierarchical Clustering", Applied Optics, Sep. 1, 2007, vol. 46, No. 25, pp. 6368-6374.
Johnston et al., "A Real-Time FPGA Implementation of a Barrel Distortion Correction Algorithm", Projects, 2003, vol. 10, pp. 91-96.
Karion et al., "Methane Emissions Estimate from Airborne Measurements Over a Western United States Natural Gas Field", Geophysical Research Letters, 2013, vol. 40, pp. 4393-4397.
Keshava et al., "A Survey of Spectral Unmixing Algorithms", Lincoln Laboratory Journal, 2003, vol. 14, No. 1, pp. 55-78.
Kester et al., "A Real-Time Gas Cloud Imaging Camera for Fugitive Emission Detection and Monitoring", Imaging and Applied Optics Technical Digest, 2012, pp. 3.
Kester et al., "Development of Image Mappers for Hyperspectral Biomedical Imaging Applications", Applied Optics, Apr. 1, 2010, vol. 49, No. 10, pp. 1886-1899.
Kester et al., "High Numerical Aperture Microendoscope Objective for a Fiber Confocal Reflectance Microscope", Optics Express, Mar. 5, 2007, vol. 15. No. 5, pp. 2409-2420.
Kester et al., "Low Cost, High Performance, Self-Aligning Miniature Optical Systems", Applied Optics, Jun. 20, 2009, vol. 48, No. 18, pp. 3375-3384.
Kester et al., "Real-Time Snapshot Hyperspectral Imaging Endoscope", Journal of Biomedical Optics, May 2011, vol. 16, No. 5, pp. 056005-1-056005-12.
Kudenov et al., "Fourier Transform Channeled Spectropolarimetry in the MWIR", Optics Express, Oct. 1, 2007, vol. 15, No. 20, pp. 12792-12805.
Kudenov et al., "Snapshot Imaging Mueller Matrix Polarimeter Using Polarization Gratings", Optics Letters, Apr. 15, 2012, vol. 37, No. 8, pp. 1367-1369.
Landau et al., "Design and Evaluation of an Ultra-Slim Objective for in-vivo Deep Optical Biopsy", Optics Express, Mar. 1, 2010, vol. 18, No. 5, pp. 4758-4775.
Levi, Michael A., "Comment on 'Hydrocarbon Emissions Characterization in the Colorado Front Range: A Pilot Study' by Gabrielle Pétron et al.", Journal of Geophysical Research, 2012, vol. 117, No. D21203, pp. 1-5.
Levi, Michael A., "Reply to '"Reply to 'Comment on 'Hydrocarbon Emissions Characterization in the Colorado Front Range—A Pilot Study' by Michael A. Levi" by Gabrielle Pétron et al.", Journal of Geophysical Research: Atmospheres, 2013, vol. 118, pp. 3044-3046.
Low et al., "Remote Sensing and Characterization of Stack Gases by Infrared Spectroscopy. An Approach by Using Multiple-Scan Interferometry", Environmental Science & Technology, Jan. 1967, vol. 1, No. 1, pp. 73-74.
Luo et al., "Fast Processing of Imaging Spectrometer Data Cube Based on FPGA Design", MIPPR 2007: Multispectral Image Processing, Proceedings of SPIE vol. 6787, pp. 7.
Manolakis et al., "Long-Wave Infrared Hyperspectral Remote Sensing of Chemical Clouds", IEEE Signal Processing Magazine, Jul. 2014, vol. 31, No. 4, pp. 120-141.
Mathews, "Design and Fabrication of a Low-Cost, Multispectral Imaging System," Applied Optics, 2008, pp. F71-F76, vol. 47.
Naranjo et al., "IR Gas Imaging in an Industrial Setting," Thermosense XXXII, Published in SPIE Proceedings vol. 7661, May 4, 2010, pp. 1-8.
Nguyen et al., "Snapshot 3D Optical Coherence Tomography System using Image Mapping Spectrometer", Biomedical Optics and 3D Imaging OSA, 2012, pp. 3.
Niu et al., "New Approach to Remote Gas-Phase Chemical Quantification: Selected-Band Algorithm", Optical Engineering, Feb. 2014, vol. 53, No. 2, pp. 021111-1-021111-10.
"Oil and Natural Gas Sector Leaks", U.S. EPA Office of Air Quality Planning and Standards (OAQPS), Review Panel, Apr. 2014, pp. 63.
Pétron et al., "Hydrocarbon Emissions Characterization in the Colorado Front Range: A Pilot Study", Journal of Geophysical Research, 2012, vol. 117, No. D04304, pp. 1-19.
Pétron et al., "Reply to Comment on 'Hydrocarbon Emissions Characterization in the Colorado Front Range—A Pilot Study' by Michael A. Levi", Journal of Geophysical Research: Atmospheres, 2013, vol. 118, pp. 236-242.
Pisano et al., "Thermal Illuminators for Far-Infrared and Submillimeter Astronomical Instruments," Applied Optics, Jun. 1, 2005, vol. 44, No. 16, pp. 3208-3217.
Polak et al., "Passive Fourier—Transform Infrared Spectroscopy of Chemical Plumes: An Algorithm for Quantitative Interpretation and Real-Time Background Removal", Applied Optics, Aug. 20, 1995, vol. 34, No. 24, pp. 5406-5412.
Rebellion Photonics, "Gas Cloud Imaging Camera: A Breakthrough in Leak Monitoring for the Rig & Refinery Safety Market", Presentation at SPIE Defense Security and Sensing, 28 pages, Apr. 29-May 3, 2013.

(56) References Cited

OTHER PUBLICATIONS

Sandsten et al., "Development of Infrared Spectroscopy Techniques for Environmental Monitoring", Doctoral Thesis, Aug. 2000, pp. 123.
Sandsten et al., "Real-Time Gas-Correlation Imaging Employing Thermal Background Radiation", Optics Express, Feb. 14, 2000, vol. 6, No. 4, pp. 92-103.
Sandsten et al., "Volume Flow Calculations on Gas Leaks Imaged with Infrared Gas-Correlation," Optics Express, 2012, vol. 20, No. 18, pp. 20318-20329.
Shogenji et al., "Multispectral Imaging Using Compact Compound Optics," Optics Express, Apr. 19, 2004, vol. 12, No. 8, pp. 1643-1655.
Telops, "Hyper-Cam", http://web.archive.org/web/20160608180941/http://www.telops.com/en/hyperspectral-cameras/hyper-cam as archived Jun. 8, 2016 in 2 pages.
Telops, "Innovative Infrared Imaging", http://web.archive.org/web/20160603212729/http://www.telops.com/en/ as archived Jun. 3, 2016 in 2 pages.
Walter Jr., et al., "Detection of Atmospheric Pollutants: a Correlation Technique", Applied Optics, Jun. 1975, vol. 14, No. 6, pp. 1423-1428.
Wikipedia entry https://en.wikipedia.org/wiki/Mobile_computing last modified on Dec. 30, 2016; retrieved from the internet on Feb. 2, 2017 in 6 pages.
Williams et al., "Dual-Band MWIR/LWIR Radiometer for Absolute Temperature Measurements," SPIE Thermosense Conference XXVIII—Manuscript 6205-23, Apr. 18, 2006, pp. 13.
Young et al., "An In-Scene Method for Atmospheric Compensation of Thermal Hyperspectral Data", Journal of Geophysical Research, 2002, vol. 107, No. D24, pp. 14-1-14-20.
Zheng et al., "A Static Multiplex Fabry-Perot Spectrometer", Sensors, Cameras, and Systems for Industrial/Scientific Applications X, Proceedings of SPIE-IS&T Electronic Imaging, SPIE vol. 7249, 2009, pp. 8.
Zheng et al., "Analytic-Domain Lens Design with Proximate Ray Tracing", Journal of the Optical Society of America A, Aug. 2010, vol. 27, No. 8, pp. 1791-1802.
Preliminary Amendment as filed in U.S. Appl. No. 14/538,827 dated Jan. 28, 2015 in 6 pages.
Official Communication received in U.S. Appl. No. 14/538,827 dated Jun. 30, 2015 in 8 pages.
Non-Final Office Action Response as filed in U.S. Appl. No. 14/538,827 dated Dec. 28, 2015 in 11 pages.
Notice of Allowance received in U.S. Appl. No. 14/538,827 dated Feb. 1, 2016 in 18 pages.
Corrected Notice of Allowance received in U.S. Appl. No. 14/538,827 dated Feb. 10, 2016 in 4 pages.
Corrected Notice of Allowance received in U.S. Appl. No. 14/538,827 dated Feb. 22, 2016 in 4 pages.
Request for Continued Examination and Response to Correct Application Papers as filed in U.S. Appl. No. 14/538,827 dated Apr. 29, 2016 in 14 pages.
Notice of Allowance received in U.S. Appl. No. 14/538,827 dated May 26, 2016 in 9 pages.
Notice of Allowance received in U.S. Appl. No. 14/538,827 dated Sep. 19, 2016 in 9 pages.
Amendment as filed in U.S. Appl. No. 14/538,827 dated Dec. 16, 2016 in 9 pages.
Official Communication received in U.S. Appl. No. 15/418,532 dated Jun. 23, 2017 in 7 pages.
Amendment as filed in U.S. Appl. No. 15/418,532 dated Nov. 22, 2017 in 8 pages.
Official Communication received in U.S. Appl. No. 15/418,532 dated Dec. 11, 2017 in 21 pages.
Notice of Allowance received in U.S. Appl. No. 15/418,532 dated Jun. 15, 2018 in 12 pages.
Corrected Notice of Allowance received in U.S. Appl. No. 15/418,532 dated Jul. 6, 2018 in 3 pages.
Amendment after Allowance as filed in U.S. Appl. No. 15/418,532 dated Sep. 14, 2018 in 6 pages.
Notice of Allowance received in U.S. Appl. No. 15/418,532 dated Dec. 5, 2018 in 11 pages.
Official Communication received in U.S. Appl. No. 14/543,692 dated Nov. 3, 2015 in 7 pages.
Interview Summary received in U.S. Appl. No. 14/543,692 dated Feb. 17, 2016 in 5 pages.
Response to Office Action as filed in U.S. Appl. No. 14/543,692 dated May 2, 2016 in 9 pages.
Official Communication received in U.S. Appl. No. 14/543,692 dated Jun. 1, 2016 in 18 pages.
Response to Final Action as filed in U.S. Appl. No. 14/543,692 dated Nov. 30, 2016 in 12 pages.
Notice of Allowance received in U.S. Appl. No. 14/543,692 dated Dec. 9, 2016 in 12 pages.
Amendment after Allowance as filed in U.S. Appl. No. 14/543,692 dated Mar. 3, 2017 in 6 pages.
Notice of Allowance received in U.S. Appl. No. 14/543,692 dated Mar. 17, 2017 in 4 pages.
Preliminary Amendment as filed in U.S. Appl. No. 15/471,398 dated Oct. 6, 2017 in 6 pages.
Notice of Allowance received in U.S. Appl. No. 14/571,398 dated Oct. 18, 2017 in 8 pages.
Notice of Allowance received in U.S. Appl. No. 14/571,398 dated Feb. 7, 2018 in 20 pages.
Notice of Allowance received in U.S. Appl. No. 14/571,398 dated Jul. 2, 2018 in 8 pages.
Notice of Allowance received in U.S. Appl. No. 14/571,398 dated Oct. 24, 2018 in 7 pages.
Official Communication received in U.S. Appl. No. 14/539,899 dated Mar. 26, 2015 in 6 pages.
Non-Final Office Action Response as filed in U.S. Appl. No. 14/539,899 dated Aug. 26, 2015 in 8 pages.
Official Communication received in U.S. Appl. No. 14/539,899 dated Dec. 11, 2015 in 9 pages.
Amendment as filed in U.S. Appl. No. 14/539,899 dated Jun. 9, 2016 in 6 pages.
Notice of Allowance received in U.S. Appl. No. 14/539,899 dated Jun. 21, 2016 in 17 pages.
Notice of Allowance received in U.S. Appl. No. 14/539,899 dated Oct. 31, 2016 in 10 pages.
Amendment as filed in U.S. Appl. No. 14/539,899 dated Jan. 27, 2017 in 5 pages.
Official Communication received in U.S. Appl. No. 15/462,352 dated Sep. 28, 2017 in 6 pages.
Amendment as filed in U.S. Appl. No. 15/462,352 dated Feb. 28, 2018 in 5 pages.
Notice of Allowance received in U.S. Appl. No. 15/462,352 dated Jul. 17, 2018 in 25 pages.
Notice to File Corrected Application Papers received in U.S. Appl. No. 15/462,352 dated Aug. 8, 2018 in 3 pages.
Response to Notice to File Corrected Application Papers filed in U.S. Appl. No. 15/462,352 dated Oct. 8, 2018 in 3 pages.
Notice of Allowance received in U.S. Appl. No. 15/462,352 dated Oct. 31, 2018 in 9 pages.
Notice of Allowance received in U.S. Appl. No. 15/462,352 dated Feb. 12, 2019 in 9 pages.
Official Communication received in European Application No. 13732285.5 dated Jul. 26, 2018 in 6 pages.
Extended European Search Report received in European Application No. 14192862.2 dated Mar. 30, 2015 in 10 pages.
Official Communication received in European Application No. 14192862.2 dated Apr. 19, 2016 in 6 pages.
Official Communication received in European Application No. 14192862.2 dated May 2, 2018 in 3 pages.
International Search Report in PCT Application No. PCT/US2013/041278 dated Aug. 27, 2013 in 4 pages.
International Preliminary Report on Patentability in PCT Application No. PCT/US2013/041278 dated Nov. 27, 2014 in 10 pages.
Preliminary Amendment as filed in U.S. Appl. No. 14/700,791 dated Jul. 13, 2015 in 8 pages.

(56) References Cited

OTHER PUBLICATIONS

Notice of Allowance received in U.S. Appl. No. 14/700,791 dated Jun. 9, 2016 in 11 pages.
Notice of Allowance received in U.S. Appl. No. 14/700,791 dated Sep. 30, 2016 in 19 pages.
Notice of Allowance received in U.S. Appl. No. 14/700,791 dated Feb. 21, 2017 in 20 pages.
Comments on Allowance filed in U.S. Appl. No. 14/700,791 dated May 19, 2017 in 2 pages.
Notice of Allowance received in U.S. Appl. No. 14/700,791 dated Jul. 10, 2017 in 24 pages.
Preliminary Amendment as filed in U.S. Appl. No. 15/623,942 dated Dec. 7, 2017 in 6 pages.
Notice of Allowance received in U.S. Appl. No. 15/623,942 dated Jan. 24, 2018 in 22 pages.
Notice of Allowance received in U.S. Appl. No. 15/623,942 dated May 24, 2018 in 23 pages.
Comments on Allowance filed in U.S. Appl. No. 15/623,942 dated Aug. 23, 2018 in 2 pages.
Extended European Search Report received in European Application No. 15165877.0 dated Oct. 8, 2015 in 12 pages.
Official Communication received in European Application No. 15165877.0 dated Jan. 3, 2017 in 9 pages.
Preliminary Amendment as filed in U.S. Appl. No. 14/700,567 dated Jul. 10, 2015 in 6 pages.
Publication Request as filed in U.S. Appl. No. 14/700,567 dated Aug. 24, 2016 in 237 pages.
Official Communication received in U.S. Appl. No. 14/700,567 dated Jun. 14, 2017 in 29 pages.
Amendment as filed in U.S. Appl. No. 14/700,567 dated Dec. 13, 2017 in 12 pages.
Official Communication received in U.S. Appl. No. 14/700,567 dated Mar. 5, 2018 in 38 pages.
Amendment as filed in U.S. Appl. No. 14/700,567 dated Jul. 5, 2018 in 10 pages.
Office Action as filed in U.S. Appl. No. 14/700,567 dated Aug. 27, 2018 in 36 pages.
Extended European Search Report received in European Application No. EP 15165880.4 dated Nov. 24, 2015 in 8 pages.
Preliminary Amendment as filed in U.S. Appl. No. 14/792,477 dated Dec. 21, 2015 in 7 pages.
Official Communication received in U.S. Appl. No. 14/792,477 dated Jan. 27, 2017 in 10 pages.
Response to Restriction Requirement submitted in U.S. Appl. No. 14/792,477 dated May 8, 2017 in 6 pages.
Official Communication received in U.S. Appl. No. 14/792,477 dated Jul. 19, 2017 in 20 pages.
Amendment as filed in U.S. Appl. No. 14/792,477 dated Jan. 18, 2018 in 10 pages.
Notice of Allowance received in U.S. Appl. No. 14/792,477 dated Apr. 19, 2018 in 13 pages.
Notice of Allowance received in U.S. Appl. No. 14/792,477 dated Sep. 20, 2018 in 14 pages.
Notice of Allowance received in U.S. Appl. No. 14/792,477 dated Jan. 30, 2019 in 11 pages.
Preliminary Amendment as filed in U.S. Appl. No. 15/166,092 dated Aug. 15, 2016 in 7 pages.
Official Communication received in U.S. Appl. No. 15/166,092 dated May 15, 2018 in 30 pages.
Amendment as filed in U.S. Appl. No. 15/166,092 dated Nov. 15, 2018 in 11 pages.
International Search Report in PCT Application No. PCT/US2016/034455 dated Oct. 24, 2016 in 12 pages.
International Preliminary Report on Patentability in PCT Application No. PCT/US2016/034455 dated Dec. 5, 2017 in 8 pages.
Preliminary Amendment as filed in U.S. Appl. No. 15/789,811 dated Mar. 20, 2018 in 6 pages.
Official Communication received in U.S. Appl. No. 15/789,811 dated Jul. 27, 2018 in 22 pages.
Interview Summary received in U.S. Appl. No. 15/789,811 dated Nov. 20, 2018 in 3 pages.
Invitation to Pay Additional Fees in PCT Application No. PCT/US2017/057725 dated Dec. 14, 2017 in 3 pages.
International Search Report in PCT Application No. PCT/US2017/057725 dated Feb. 14, 2018 in 14 pages.
Preliminary Amendment as filed in U.S. Appl. No. 15/789,829 dated Mar. 20, 2018 in 8 pages.
Official Communication received in U.S. Appl. No. 15/789,829 dated Jun. 5, 2018 in 16 pages.
Amendment as filed in U.S. Appl. No. 15/789,829 dated Dec. 4, 2018 in 9 pages.
Invitation to Pay Additional Fees in PCT Application No. PCT/US2017/057712 dated Jan. 10, 2018 in 2 pages.
International Search Report in PCT Application No. PCT/US2017/057712 dated Mar. 6, 2018 in 12 pages.
Preliminary Amendment as filed in U.S. Appl. No. 15/902,336 dated Sep. 20, 2018 in 9 pages.
International Search Report in PCT Application No. PCT/US2018/019271 dated Jun. 27, 2018 in 15 pages.
International Search Report in PCT Application No. PCT/US2018/059890 dated Jan. 23, 2019 in 10 pages.
ARPA-E, "Portable Methane Detection System", dated Dec. 16, 2014 (including innovation update from May 2018) in 2 pages https://arpa-e.energy.gov/?q=slick-sheet-project/portable-methane-detection-system.
ARPA-E, "Wearable, Continuously Monitoring Methane Imagers", as updated Jan. 15, 2018 in 2 pages https://arpa-e.energy.gov/sites/default/files/Rebellion-MONITOR-May1.pdf.
Weldon et al., "H2S and CO2 gas sensing using DFB laser diodes emitting at 1.57 μm", Sensors and Actuators B: Chemical, Oct. 1995, vol. 29, Issues 1-3, pp. 101-107.
Amendment After Allowance as filed in U.S. Appl. No. 15/471,398 dated Jan. 24, 2019 in 5 pages.
Notice of Allowance received in U.S. Appl. No. 14/571,398 dated Feb. 27, 2019 in 14 pages.
Notice of Allowance received in U.S. Appl. No. 14/571,398 dated Mar. 6, 2019 in 5 pages.
Amendment as filed in U.S. Appl. No. 15/462,352 dated Apr. 30, 2019 in 5 pages.
Notice of Allowance received in U.S. Appl. No. 15/462,352 dated May 23, 2019, 2019 in 10 pages.
Official Communication received in Canadian Application No. 2,873,989 dated Mar. 21, 2019 in 6 pages.
Preliminary Amendment as filed in U.S. Appl. No. 16/138,823 dated May 23, 2019 in 5 pages.
Notice of Allowance received in U.S. Appl. No. 16/138,823 dated Jun. 14, 2019 in 10 pages.
Notice of Allowance received in U.S. Appl. No. 14/792,477 dated Jun. 21, 2019 in 10 pages.
Official Communication received in U.S. Appl. No. 15/166,092 dated Dec. 20, 2018 in 28 pages.
Extended European Search Report received in European Application No. EP 16804077.2 dated Jan. 8, 2019 in 8 pages.
Amendment as filed in U.S. Appl. No. 15/789,811 dated Jan. 25, 2019 in 7 pages.
Notice of Allowance received in U.S. Appl. No. 15/789,811 dated Mar. 27, 2019 in 9 pages.
International Preliminary Report on Patentability in PCT Application No. PCT/US2017/057725 dated May 2, 2019 in 10 pages.
Notice of Allowance received in U.S. Appl. No. 15/789,829 dated Feb. 25, 2019 in 28 pages.
Amendment as filed in U.S. Appl. No. 15/789,829 dated May 24, 2019 in 7 pages.
International Preliminary Report on Patentability in PCT Application No. PCT/US2017/057712 dated May 2, 2019 in 9 pages.
International Preliminary Report on Patentability in PCT Application No. PCT/US2018/019271, dated Sep. 6, 2019 in 11 pages.
Notice of Allowance received in U.S. Appl. No. 15/789,829, dated Jul. 19, 2019 in 14 pages.
Amendment as filed in U.S. Appl. No. 15/166,092, dated Jun. 20, 2019 in 10 pages.

(56) References Cited

OTHER PUBLICATIONS

Amendment as filed in U.S. Appl. No. 15/462,352, dated Aug. 21, 2019 in 5 pages.
Amendment as filed in U.S. Appl. No. 16/138,823, dated Nov. 14, 2019 in 6 pages.
Amendment as filed in U.S. Appl. No. 16/664,615, dated Jan. 16, 2020 in 5 pages.
Catanzaro, et al., "Design of Dual-Band SWIR/MWIR and MWIR/LWIR Imagers", Proceedings of SPIE 5406, Infrared Technology and Applications XXX, Aug. 30, 2004, pp. 829-835.
Extended European Search Report received in European Application No. 19170836.1, dated Aug. 16, 2019 in 12 pages.
King et al., "Airborne Scanning Spectrometer for Remote Sensing of Cloud, Aerosol, Water Vapor, and Surface Properties", Journal of Atmospheric and Oceanic Technology, Aug. 1996, vol. 13, No. 4, pp. 777-794.
Notice of Allowance received in U.S. Appl. No. 15/166,092, dated Oct. 18, 2019 in 19 pages.
Official Communication received in U.S. Appl. No. 15/789,829, dated Nov. 6, 2019 in 23 pages.
Preliminary Amendment as filed in U.S. Appl. No. 16/377,678, dated Nov. 21, 2019 in 4 pages.

\* cited by examiner

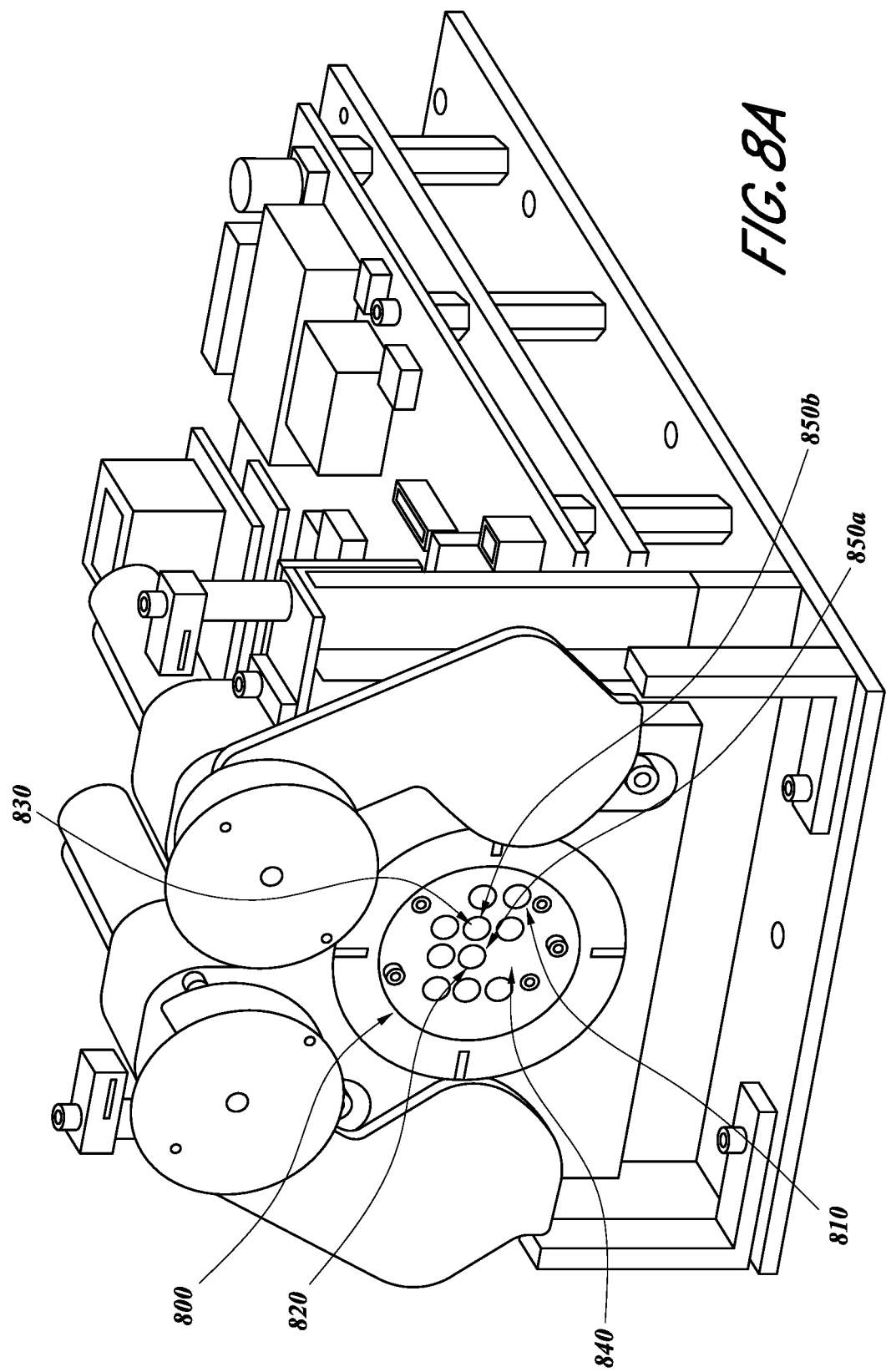

WINDOW OBSCURATION SENSORS FOR MOBILE GAS AND CHEMICAL IMAGING CAMERAS

INCORPORATION BY REFERENCE TO ANY PRIORITY APPLICATIONS

This application claims priority to U.S. Provisional Patent Application No. 62/584,076, filed Nov. 9, 2017, entitled "WINDOW OBSCURATION SENSORS FOR MOBILE GAS AND CHEMICAL IMAGING CAMERAS;" and U.S. Provisional Patent Application No. 62/584,684, filed Nov. 10, 2017, entitled "WINDOW OBSCURATION SENSORS FOR MOBILE GAS AND CHEMICAL IMAGING CAMERAS;" the entire contents of each of which are hereby incorporated by reference herein in their entirety and for all purposes.

STATEMENT REGARDING FEDERALLY SPONSORED R&D

Funding for some portions of the technology disclosed in this application was provided by the Advanced Research Projects Agency—Energy (ARPA-E) under Contract Number DE-AR0000541. The government may have certain rights in these portions of the technology.

FIELD OF THE INVENTION

The present invention generally relates to a system and method for gas cloud detection and, in particular, to a system and method of detecting obscuration of a camera window in gas and chemical imaging cameras.

DESCRIPTION OF THE RELATED TECHNOLOGY

Spectral imaging systems and methods have applications in a variety of fields. Spectral imaging systems and methods obtain a spectral image of a scene in one or more regions of the electromagnetic spectrum to detect phenomena, identify material compositions or characterize processes. The spectral image of the scene can be represented as a three-dimensional data cube where two axes of the cube represent two spatial dimensions of the scene and a third axis of the data cube represents spectral information of the scene in different wavelength regions. The data cube can be processed using mathematical methods to obtain information about the scene. Some of the existing spectral imaging systems generate the data cube by scanning the scene in the spatial domain (e.g., by moving a slit across the horizontal dimensions of the scene) and/or spectral domain (e.g., by scanning a wavelength dispersive element to obtain images of the scene in different spectral regions). Such scanning approaches acquire only a portion of the full data cube at a time. These portions of the full data cube are stored and then later processed to generate a full data cube.

SUMMARY

The systems, methods and devices of this disclosure each have several innovative aspects, no single one of which is solely responsible for the desirable attributes disclosed herein.

Various examples of imaging systems comprising an optical window and with capabilities to determine if the optical window is obscured (e.g., to detect objects on or in front of the window that may introduce obscuration that may degrade operation of the system) are described herein such as the examples enumerated below:

Example 1

An example of an infrared (IR) imaging system comprising:
  a housing;
  an optical window disposed on the housing;
  an optical detector system disposed within the housing; and
  a plurality of spatially and spectrally distinct optical channels that transfer incident IR radiation from the optical window to the optical detector system, wherein a first optical channel out of the plurality of optical channels has a focus distance that is closer to the optical window than at least some of the other optical channels of the plurality of optical channels to detect whether the optical window is obscured.

Example 2

The IR imaging system of Example 1, wherein the first optical channel out of the plurality of optical channels has a focus less than 2 meters and other optical channels of the plurality of optical channels have a focus of greater than 10 meters.

Example 3

The IR imaging system of any one of Examples 1 to 2, wherein the first optical channel out of the plurality of optical channels has a focus less than 2 meters and other optical channels of the plurality of optical channels have a focus of greater than 20 meters.

Example 4

The IR imaging system of any one of Examples 1 to 3, wherein the first optical channel out of the plurality of optical channels has a focus less than 2 meters and other optical channels of the plurality of optical channels have a focus of greater than 30 meters.

Example 5

The IR imaging system of any one of Examples 1 to 4, wherein the first optical channel out of the plurality of optical channels has a focus of 1 meter or less and other optical channels of the plurality of optical channels have a focus of greater than 10 meters.

Example 6

The IR imaging system of any one of Examples 1 to 5, wherein the first optical channel out of the plurality of optical channels has a focus of 1 meter or less and other optical channels of the plurality of optical channels have a focus of greater than 20 meters.

Example 7

The IR imaging system of any one of Examples 1 to 6, wherein the first optical channel out of the plurality of optical channels has a focus of 1 meter or less and other optical channels of the plurality of optical channels have a focus of greater than 30 meters.

Example 8

The IR imaging system of any one of Examples 1 to 7, wherein at least some of the other optical channels of the plurality of optical channels have focus distances at least 5 meters greater than the focus distance of the first optical channel.

Example 9

The IR imaging system of any one of Examples 1 to 8, wherein at least some of the other optical channels of the plurality of optical channels have focus distances at least 10 meters greater than the focus distance of the first optical channel.

Example 10

The IR imaging system of any one of Examples 1 to 9, wherein at least some of the other optical channels of the plurality of optical channels have focus distances at least 20 meters greater than the focus distance of the first optical channel.

Example 11

The IR imaging system of any one of Examples 1 to 10, wherein the first optical channel out of the plurality of optical channels has a focus distance of 1 meter or less.

Example 12

The IR imaging system of any one of Examples 1 to 11, wherein the first optical channel out of the plurality of optical channels has a focus distance of 2 meter or less.

Example 13

The IR imaging system of any one of Examples 1 to 12, wherein the first optical channel and the other optical channels include imaging lenses for imaging objects onto the optical detector system, said imaging lenses having focal lengths.

Example 14

The IR imaging system of any one of Examples 1 to 13, wherein the focal lengths for lenses in the other optical channels exceed the focal length for the first optical channel.

Example 15

The IR imaging system of any one of Examples 1 to 14, wherein the focal lengths for lenses in the other optical channels exceed the focal length for the first optical channel by at least 2×.

Example 16

The IR imaging system of any one of Examples 1 to 15, wherein the focal lengths for lenses in the other optical channels exceed the focal length for the first optical channel by at least 5×.

Example 17

The IR imaging system of any one of Examples 1 to 16, wherein the first optical channel is in focus at the optical window to detect whether the optical window is obscured.

Example 18

The IR imaging system of any one of Examples 1 to 17, wherein the first optical channel has a depth of field over which the optical channel is substantially in focus and wherein the depth of field of the first optical channel extends between a depth of the optical window and approximately 1 meter beyond the optical window.

Example 19

The IR imaging system of any one of Examples 1 to 18, wherein the first optical channel has a depth of field over which the optical channel is substantially in focus and wherein the depth of field of the first optical channel extends between a depth of the optical window and approximately 50 cm beyond the optical window.

Example 20

The IR imaging system of any one of Examples 1 to 19, wherein the first optical channel has a depth of field over which the optical channel is substantially in focus and wherein the depth of field of the first optical channel extends between a depth of the optical window and approximately 20 cm beyond the optical window.

Example 21

The IR imaging system of any one of Examples 1 to 20, wherein the first optical channel has a depth of field over which the optical channel is substantially in focus and wherein the depth of field of the first optical channel extends between a depth of the optical window and approximately 10 cm beyond the optical window.

Example 22

The IR imaging system of any one of Examples 1 to 21, further comprising:
a processing unit comprising processing electronics configured to process image data from the first optical channel to detect whether the optical window is obscured.

Example 23

The IR imaging system of any one of Examples 1 to 22, wherein the processing unit is configured to evaluate how much of the image data is in focus to detect whether the optical window is obscured.

Example 24

The IR imaging system of any one of Examples 1 to 23, wherein the processing unit is configured to evaluate the contrast of the image data to detect whether the optical window is obscured.

Example 25

The IR imaging system of any one of Examples 1 to 24, wherein the processing unit is configured to perform edge enhancement of the image data.

Example 26

The IR imaging system of any one of Examples 1 to 25, wherein the processing unit is configured to perform edge detection of the image data.

Example 27

The IR imaging system of any one of Examples 1 to 26, wherein the processing unit is configured to perform normalization of the image data.

Example 28

The IR imaging system of any one of Examples 1 to 27, wherein the normalization of the image data comprises scaling the image data.

Example 29

The IR imaging system of any one of Examples 1 to 28, wherein the normalization of the image data comprises subtracting from the image data.

Example 30

The IR imaging system of any one of Examples 1 to 29, wherein the processing unit is configured to evaluate whether image data exceeds a threshold to determine whether the optical window is obscured.

Example 31

The IR imaging system of any one of Examples 1 to 30, wherein a second optical channel out of the plurality of optical channels has a focus distance that is closer to the optical window than at least some of the other optical channels of the plurality of optical channels to detect whether the optical window is obscured.

Example 32

The IR imaging system of Example 31, wherein the second optical channel out of the plurality of optical channels has a focus less than 2 meters and other optical channels of the plurality of optical channels have a focus of greater than 10 meters.

Example 33

The IR imaging system of any one of Examples 1 to 32, wherein the second optical channel out of the plurality of optical channels has a focus less than 2 meters and other optical channels of the plurality of optical channels have a focus of greater than 20 meters.

Example 34

The IR imaging system of any one of Examples 1 to 33, wherein the second optical channel out of the plurality of optical channels has a focus less than 2 meters and other optical channels of the plurality of optical channels have a focus of greater than 30 meters.

Example 35

The IR imaging system of any one of Examples 1 to 34, wherein the second optical channel out of the plurality of optical channels has a focus of 1 meter or less and other optical channels of the plurality of optical channels have a focus of greater than 10 meters.

Example 36

The IR imaging system of any one of Examples 1 to 35, wherein the second optical channel out of the plurality of optical channels has a focus of 1 meter or less and other optical channels of the plurality of optical channels have a focus of greater than 20 meters.

Example 37

The IR imaging system of any one of Examples 1 to 36, wherein the second optical channel out of the plurality of optical channels has a focus of 1 meter or less and other optical channels of the plurality of optical channels have a focus of greater than 30 meters.

Example 38

The IR imaging system of any one of Examples 1 to 37, wherein at least some of the other optical channels of the plurality of optical channels have focus distances at least 5 meters greater than the focus distance of the second optical channel.

Example 39

The IR imaging system of any one of Examples 1 to 38, wherein at least some of the other optical channels of the plurality of optical channels have focus distances at least 10 meters greater than the focus distance of the second optical channel.

Example 40

The IR imaging system of any one of Examples 1 to 39, wherein at least some of the other optical channels of the plurality of optical channels have focus distances at least 20 meters greater than the focus distance of the second optical channel.

Example 41

The IR imaging system of any one of Examples 1 to 40, wherein the second optical channel out of the plurality of optical channels has a focus distance of 1 meter or less.

Example 42

The IR imaging system of any one of Examples 1 to 41, wherein the second optical channel out of the plurality of optical channels has a focus distance of 2 meter or less.

Example 43

The IR imaging system of any one of Examples 1 to 42, wherein the second optical channel and the other optical channels include imaging lenses for imaging objects onto the optical detector system, said imaging lenses having focal lengths.

Example 44

The IR imaging system of any one of Examples 1 to 43, wherein the focal lengths for lenses in the other optical channels exceed the focal length for the second optical channel.

Example 45

The IR imaging system of any one of Examples 1 to 44, wherein the focal lengths for lenses in the other optical channels exceed the focal length for the second optical channel by at least 2×.

Example 46

The IR imaging system of any one of Examples 1 to 45, wherein the focal lengths for lenses in the other optical channels exceed the focal length for the second optical channel by at least 5×.

Example 47

The IR imaging system of any one of Examples 1 to 46, wherein a second optical channel out of the plurality of optical channels is in focus at the optical window to detect whether the optical window is obscured.

Example 48

The IR imaging system of any one of Examples 1 to 47, wherein the second optical channel has a depth of field over which the optical channel is substantially in focus and wherein the depth of field of the second optical channel extends between a depth of the optical window and approximately 1 meter beyond the optical window.

Example 49

The IR imaging system of any one of Examples 1 to 48, wherein the second optical channel has a depth of field over which the optical channel is substantially in focus and wherein the depth of field of the second optical channel extends between a depth of the optical window and approximately 50 cm beyond the optical window.

Example 50

The IR imaging system of any one of Examples 1 to 49, wherein the second optical channel has a depth of field over which the optical channel is substantially in focus and wherein the depth of field of the second optical channel extends between a depth of the optical window and approximately 20 cm beyond the optical window.

Example 51

The IR imaging system of any one of Examples 1 to 50, wherein the second optical channel has a depth of field over which the optical channel is substantially in focus and wherein the depth of field of the second optical channel extends between a depth of the optical window and approximately 10 cm beyond the optical window.

Example 52

The IR imaging system of any one of Examples 1 to 51, wherein the processing unit is configured to process image data from the second optical channel to detect whether the optical window is obscured.

Example 53

The IR imaging system of any one of Examples 1 to 52, wherein the processing unit is configured to evaluate how much of the image data from the second optical channel is in focus to detect whether the optical window is obscured.

Example 54

The IR imaging system of any one of Examples 1 to 53, wherein the processing unit is configured to evaluate the contrast of the image data from the second optical channel to detect whether the optical window is obscured.

Example 55

The IR imaging system of any one of Examples 1 to 54, wherein the processing unit is configured to perform edge enhancement of the image data from the second optical channel.

Example 56

The IR imaging system of any one of Examples 1 to 55, wherein the processing unit is configured to perform edge detection of the image data from the second optical channel.

Example 57

The IR imaging system of any one of Examples 1 to 56, wherein the processing unit is configured to perform normalization of the image data from the second optical channel.

Example 58

The IR imaging system of any one of Examples 1 to 57, wherein the normalization of the image data comprises scaling the image data from the second optical channel.

Example 59

The IR imaging system of any one of Examples 1 to 58, wherein the normalization of the image data comprises subtracting from the image data from the second optical channel.

Example 60

The IR imaging system of any one of Examples 1 to 59, wherein the processing unit is configured to evaluate whether image data from the second optical channel exceeds a threshold to determine whether the optical window is obscured.

Example 61

The IR imaging system of any one of Examples 1 to 60, wherein a plurality of the optical channels are in focus at optical infinity to detect a target species.

Example 62

The IR imaging system of any one of Examples 1 to 61, wherein a plurality of the optical channels are in focus at a distance of at least 10 meters to detect a target species.

Example 63

The IR imaging system of any one of Examples 1 to 62, wherein a plurality of the optical channels are in focus at a distance of at least 20 meters to detect a target species.

Example 64

The IR imaging system of any one of Examples 1 to 63, wherein the processing unit is further configured to process image data from the plurality of optical channels to detect the target species.

Example 65

The IR imaging system of any one of Examples 1 to 64, wherein the optical detector system comprises a plurality of optical detectors, each of which is associated with a respective one of the optical channels.

Example 66

The IR imaging system of any one of Examples 1 to 65, wherein the optical detector system comprises at least one optical detector having a plurality of regions, each of the regions being associated with a respective one of the optical channels.

Example 67

The IR imaging system of any one of Examples 1 to 66, wherein:
  a second optical channel out of the plurality of optical channels is in focus at the optical window; and
  the processing unit is configured to process image data from the first and second optical channels to detect whether the optical window is obscured.

Example 68

The IR imaging system of any one of Examples 1 to 67, wherein the processing unit is configured to:
  compare image data from the first and second optical channels to detect whether the optical window is obscured.

Example 69

The IR imaging system of any one of Examples 1 to 68, wherein comparing the first and second images comprises comparing the first and second images and using differences between the first and second images caused by parallax to determine whether the optical window is obscured.

Example 70

The IR imaging system of any one of Examples 1 to 69, wherein comparing the first and second images comprises performing a correlation of the first and second images.

Example 71

The IR imaging system of any one of Examples 1 to 70, wherein the first and second optical channels are spatially distinct in a given direction and wherein processing unit is configured to:
  comparing image data from the first and second optical channels at a plurality of offsets along the given direction to detect whether the optical window is obscured.

Example 72

The IR imaging system of any one of Examples 1 to 71, wherein the processing unit is configured to enhance edges in the image data from the two optical channels.

Example 73

The IR imaging system of any one of Examples 1 to 72, wherein the processing unit is configured to apply an unsharp mask to the image data from the two optical channels.

Example 74

The IR imaging system of any one of Examples 1 to 73, wherein the processing unit is configured to subtract at least one reference image from the image data from the two optical channels.

Example 75

The IR imaging system of any one of Examples 1 to 74, wherein the processing unit is configured to detect edges in the image data from the two optical channels.

Example 76

The IR imaging system of any one of Examples 1 to 75, wherein the processing unit is configured to apply an edge detection mask to the image data from the two optical channels.

Example 77

The IR imaging system of any one of Examples 1 to 76, wherein the processing unit is configured to apply Sobel filter to the image data from the two optical channels.

Example 78

The IR imaging system of any one of Examples 1 to 77, wherein the processing unit is configured to apply Sobel filter to the image data from the two optical channels to create first and second gradient images.

Example 79

The IR imaging system of any one of Examples 1 to 78, wherein the processing unit is configured to normalize the first and second gradient images.

Example 80

The IR imaging system of any one of Examples 1 to 79, wherein the processing unit is configured to cross-correlate the first and second gradient images to detect whether the optical window is obscured.

Example 81

The IR imaging system of any one of Examples 1 to 80, wherein the window is embedded in the housing or is in an opening in the housing.

Example 82

The IR imaging system of any one of Examples 1 to 81, wherein the IR imaging system is configured to compensate for effects of attenuation due to the window being obscured.

Example 83

The IR imaging system of any one of Examples 1 to 82, wherein said IR imaging system is configured to perform spectral analysis on images to detect target species and is configured to compensate for effects of attenuation due to the window being obscured on said spectral analysis.

Example 84

The IR imaging system of any one of Examples 1 to 83, wherein said IR imaging system is configured to perform spectral analysis on images to detect target species and is configured to deemphasize one or more frames of infrared image data from the other optical channels of the plurality of optical channels in the determination of the presence of a target species.

Example 85

An example of an infrared (IR) imaging system for imaging a target species in a scene, the IR imaging system comprising:
an optical window;
a first camera system configured to acquire infrared image data of the scene through the optical window;
a second camera system focused closer to the optical window than the first camera system; and
a processing unit containing a processor configured to:
analyze the infrared image data from the first camera system to detect the target species based on the infrared image data; and
analyze image data from the second camera system to determine that the optical window is obscured based on the image data from the second camera system.

Example 86

The IR imaging system of Example 85, wherein the first and second camera system comprise first and second optical channels that are spatially and spectrally distinct.

Example 87

The IR imaging system of any one of Examples 85 to 86, wherein said processing unit is configured to provide a window obscuration alert after determining that the optical window is obscured.

Example 88

The IR imaging system of any one of Examples 85 to 87, wherein the processing unit is configured to receive the window obscuration alert and, in response, to adjust the infrared image data from the first camera system in compensation for the obscuration of the optical window.

Example 89

The IR imaging system of any one of Examples 85 to 88, wherein the processing unit is configured to receive the window obscuration alert and, in response, to disable analysis of the infrared image data from the first camera system.

Example 90

The IR imaging system of any one of Examples 85 to 89, wherein the processing unit is configured to receive the window obscuration alert and, in response, deemphasize one or more frames of infrared image data from the first camera system in the determination of the presence of a target species.

Example 91

The IR imaging system of any one of Examples 85 to 90, wherein the IR imaging system is configured to compensate for effects of attenuation due to the window being obscured.

Example 92

The IR imaging system of any one of Examples 85 to 91, wherein said IR imaging system is configured to perform spectral analysis on images to detect target species and is configured to compensate for effects of attenuation due to the window being obscured on said spectral analysis.

Example 93

The IR imaging system of any one of Examples 85 to 92, wherein the processing unit is configured to provide the window obscuration alert to a user.

Example 94

The IR imaging system of any one of Examples 85 to 93, wherein the IR imaging system further comprises:
an optical focal plane array (FPA) divided into portions; and
a plurality of lens assemblies, each lens assembly configured to focus light from the scene onto a different one of the portions of the FPA.

Example 95

The IR imaging system of any one of Examples 85 to 94, wherein:
the first camera system is formed from a plurality of the lens assemblies and a plurality of the portions of the FPA; and
the second camera system is formed from one of the lens assemblies and one of the portions of the FPA.

Example 96

The IR imaging system of any one of Examples 85 to 95, wherein:
the first camera system is formed from a plurality of the lens assemblies and a plurality of the portions of the FPA; and
the second camera system is formed from two of the lens assemblies and two of the portions of the FPA.

Example 97

The IR imaging system of any one of Examples 85 to 96, wherein:
the first camera system is formed from a plurality of the lens assemblies and a plurality of the portions of the FPA; and
the second camera system is formed from two of the lens assemblies and two of the portions of the FPA, wherein the two lens assemblies and the two portions of the FPA that form the second camera system comprise adjacent lens assemblies and adjacent portions of the FPA.

Example 98

The IR imaging system of any one of Examples 85 to 97, wherein the IR imaging system further comprises:
a plurality of optical focal plane arrays (FPA); and
a plurality of lenses, different lenses configured to focus light from the scene onto a different ones of FPAs.

Example 99

The IR imaging system of any one of Examples 85 to 98, wherein the IR imaging system further comprises:
a plurality of optical focal plane arrays (FPA); and
a plurality of lens assemblies, different lens assemblies configured to focus light from the scene onto a different ones of FPAs.

Example 100

The IR imaging system of any one of Examples 85 to 99, wherein the processing unit is configured to evaluate how much of the image data is in focus to detect whether the optical window is obscured.

Example 101

The IR imaging system of any one of Examples 85 to 100, wherein the processing unit is configured to evaluate the contrast of the image data to detect whether the optical window is obscured.

Example 102

The IR imaging system of any one of Examples 85 to 101, wherein the processing unit is configured to perform edge enhancement of the image data.

Example 103

The IR imaging system of any one of Examples 85 to 102, wherein the processing unit is configured to perform edge detection of the image data.

Example 104

The IR imaging system of any one of Examples 85 to 103, wherein the processing unit is configured to perform normalization of the image data.

Example 105

The IR imaging system of any one of Examples 85 to 104, wherein the normalization of the image data comprises scaling the image data.

Example 106

The IR imaging system of any one of Examples 85 to 105, wherein the normalization of the image data comprises subtracting from the image data.

Example 107

The IR imaging system of any one of Examples 85 to 106, wherein the processing unit is configured to evaluate whether image data exceeds a threshold to determine whether the optical window is obscured.

Example 108

The IR imaging system of any one of Examples 85 to 107, wherein analyzing image data from the second camera system comprises:
analyzing image data from first and second optical channels of the second camera system to detect whether the optical window is obscured.

Example 109

The IR imaging system of any one of Examples 85 to 108, wherein the processing unit is configured to:
compare image data from the first and second optical channels to detect whether the optical window is obscured.

Example 110

The IR imaging system of any one of Examples 85 to 109, wherein comparing the first and second images comprises comparing the first and second images and using differences between the first and second images caused by parallax to determine whether the optical window is obscured.

Example 111

The IR imaging system of any one of Examples 85 to 110, wherein comparing the first and second images comprises performing a correlation of the first and second images.

Example 112

The IR imaging system of any one of Examples 85 to 111, wherein the first and second optical channels are spatially distinct in a given direction and wherein processing unit is configured to:
comparing image data from the first and second optical channels at a plurality of offsets along the given direction to detect whether the optical window is obscured.

Example 113

The IR imaging system of any one of Examples 85 to 112, wherein the processing unit is configured to enhance edges in the image data from the first and second optical channels.

Example 114

The IR imaging system of any one of Examples 85 to 113, wherein the processing unit is configured to subtract at least one reference image from the image data from the first and second optical channels.

Example 115

The IR imaging system of any one of Examples 85 to 114, wherein the processing unit is configured to detect edges in the image data from the first and second optical channels.

Example 116

The IR imaging system of any one of Examples 85 to 115, wherein the processing unit is configured to apply an edge detection mask to the image data from the first and second optical channels.

Example 117

The IR imaging system of any one of Examples 85 to 116, wherein the processing unit containing the processor is configured to determine that the optical window is obscured based on the image data from the second camera system by:
receiving a first image from a first portion of the FPA;
receiving a second image from a second portion of the FPA;
transforming the first and second images into respective first and second gradient images;
determining that the gradient images have gradient values that exceed a first predetermined threshold;
providing the window obscuration alert after determining that the gradient values exceed the first predetermined threshold.

Example 118

The IR imaging system of any one of Examples 85 to 117, wherein the processing unit containing the processor is configured to determine that the optical window is obscured based on the image data from the second camera system by:
receiving a first image from a first portion of the FPA;
receiving a second image from a second portion of the FPA;
transforming the first and second images into respective first and second gradient images;
determining that the first and second gradient images have a cross-correlation value that exceeds a first predetermined threshold; and
providing the window obscuration alert after determining that the cross-correlation value exceeds the first predetermined threshold.

Example 119

The IR imaging system of any one of Examples 85 to 118, wherein the processing unit containing the processor is configured to determine that the optical window is obscured based on the image data from the second camera system by:
receiving a first image from a first portion of the FPA;
receiving a second image from a second portion of the FPA;
transforming the first and second images into respective first and second gradient images;
determining that the gradient images have gradient values that exceed a first predetermined threshold;
cross-correlating the first and second gradient images;
determining that the first and second gradient images have a cross-correlation value that exceeds a second predetermined threshold; and
providing the window obscuration alert after determining that the gradient values exceed the first predetermined threshold and the cross-correlation value exceeds the second predetermined threshold.

Example 120

The IR imaging system of any one of Examples 85 to 119, wherein:
determining that the first and second gradient images have a cross-correlation value that exceeds a second predetermined threshold comprises:
determining a plurality of cross-correlation values, each being associated with a different alignment of the first and second gradient images; and
determining that at least one cross-correlation value in the plurality of cross-correlation values exceeds the second predetermined threshold.

Example 121

The IR imaging system of any one of Examples 85 to 120, wherein:
determining that the first and second gradient images have a cross-correlation value that exceeds a second predetermined threshold comprises:
determining a plurality of cross-correlation values, each being associated with a different alignment of the first and second gradient images;
identifying a first cross-correlation value in the plurality of cross-correlation values;
subtracting the first cross-correlation value from each of the cross-correlation values in the plurality of cross-correlation values;
after subtracting the first cross-correlation value, identifying a second cross-correlation value in the plurality of cross-correlation values; and
determining that the second cross-correlation value exceeds the second predetermined threshold.

Example 122

The IR imaging system of any one of Examples 85 to 121, wherein transforming the first and second images into respective first and second gradient images comprises applying a Sobel filter to the first and second images.

Example 123

The IR imaging system of any one of Examples 85 to 122, wherein transforming the first and second images into respective first and second gradient images comprises applying a Sobel filter to the first and second images and removing values from the gradient images that fall below a predetermined threshold.

Example 124

The IR imaging system of any one of Examples 85 to 123, wherein, prior to cross-correlating the first and second gradient images, the processing unit is configured to normalize each of the gradient images.

Example 125

The IR imaging system of any one of Examples 85 to 124, wherein, prior to cross-correlating the first and second gradient images, the processing unit is configured to normalize each of the gradient images by, for each gradient image, subtracting a median value from each gradient image and dividing each gradient image by a standard deviation value.

Example 126

The IR imaging system of any one of Examples 85 to 125, wherein, prior to cross-correlating the first and second gradient images, the processing unit is configured to normalize each of the gradient images.

Example 127

The IR imaging system of any one of Examples 85 to 126, wherein, prior to transforming the first and second images into respective first and second gradient images, the processing unit is configured to subtract a first reference image from the first image and subtract a second reference image from the second image.

Example 128

The IR imaging system of any one of Examples 85 to 127, wherein the second camera system is focused within 1 meter of the optical window.

Example 129

The IR imaging system of any one of Examples 85 to 128, wherein the second camera system is focused within 2 meters of the optical window.

Example 130

The IR imaging system of any one of Examples 85 to 129, wherein the second camera system is focused on the optical window.

Example 131

The IR imaging system of any one of Examples 85 to 130, wherein the first camera system is focused at a distance of at least 10 meters.

Example 132

The IR imaging system of any one of Examples 85 to 131, wherein the first camera system is focused at a distance of at least 20 meters.

Example 133

The IR imaging system of any one of Examples 85 to 132, wherein the first camera system is focused at a distance of at least 25 meters.

Example 134

The IR imaging system of any one of Examples 85 to 133, wherein the first and second camera systems have respective imaging lenses having respective focal lengths, and the focal length for the first camera is 2 times as large as the focal length for the second camera.

Example 135

The IR imaging system of any one of Examples 85 to 134, wherein the first and second camera systems have respective imaging lenses having respective focal lengths, and the focal length for the first camera is 5 times as large as the focal length for the second camera.

Example 136

An example of a method of detecting whether an optical window in an IR imaging system is obscured, the IR imaging system comprising processing circuitry and a plurality of spatially and spectrally distinct optical channels, each optical channel including a set of lenses that focus incident IR light on a respective portion of an optical detector system, the method comprising:
- with the processing circuitry, receiving a first image from a first optical channel in the plurality of optical channels;
- with the processing circuitry, receiving a second image from a second optical channel in the plurality of optical channels; and
- with the processing circuitry, analyzing the first and second images to detect whether the optical window is obscured.

Example 137

The method of Example 136, wherein the first and second images are in focus at the depth of the optical window.

Example 138

The method of any one of Examples 136 to 137, wherein analyzing the first and second images comprises, with the processing circuitry, comparing the first and second images to identify whether the optical window is obscured.

Example 139

The method of any one of Examples 136 to 138, wherein analyzing the first and second images comprises, with the processing circuitry, comparing the first and second images and using differences between the first and second images caused by parallax to determine whether the optical window is obscured.

Example 140

The method of any one of Examples 136 to 139, wherein analyzing the first and second images comprises evaluating how much of the images are in focus to detect whether the optical window is obscured.

Example 141

The method of any one of Examples 136 to 140, wherein analyzing the first and second images comprises evaluating the contrast of the images to detect whether the optical window is obscured.

Example 142

The method of any one of Examples 136 to 141, further comprising performing edge enhancement.

Example 143

The method of any one of Examples 136 to 142, further comprising performing edge detection.

Example 144

The method of any one of Examples 136 to 143, further comprising normalizing image data.

Example 145

The method of any one of Examples 136 to 144, wherein the normalizing comprises scaling image data.

Example 146

The method of any one of Examples 136 to 145, wherein the normalizing comprises subtracting from image data.

Example 147

The method of any one of Examples 136 to 146, wherein analyzing the first and second images comprises performing a correlation of the first and second images.

Example 148

The method of any one of Examples 136 to 147, wherein analyzing the first and second images comprises comparing image data from the first and second images at a plurality of offsets along the given direction to detect whether the optical window is obscured.

Example 149

The method of any one of Examples 136 to 148, wherein analyzing the first and second images comprises evaluating whether image data exceeds a threshold to determine whether the optical window is obscured.

Example 150

The method of any one of Examples 136 to 149, wherein analyzing the first and second images comprises, with the processing circuitry, applying an unsharp mask to the first and second images.

Example 151

The method of any one of Examples 136 to 150, further comprising:
 with the processing circuitry, subtracting a first reference image from the first image and subtracting a second reference image from the second image.

Example 152

The method of any one of Examples 136 to 151, further comprising:
 with the processing circuitry, detecting edges in the first and second images.

Example 153

The method of any one of Examples 136 to 152, further comprising:
 with the processing circuitry, applying a Sobel filter to the first and second images.

Example 154

The method of any one of Examples 136 to 153, further comprising:
 with the processing circuitry, applying a Sobel filter to the first and second images to create respective first and second gradient images.

Example 155

The method of any one of Examples 136 to 154, further comprising:
 with the processing circuitry, normalizing the first and second gradient images.

Example 156

The method of any one of Examples 136 to 155, further comprising:
 with the processing circuitry, cross-correlating the first and second gradient images.

Example 157

The method of any one of Examples 136 to 156, further comprising:
 with the processing circuitry, determining that at least one cross-correlation between the first and second gradient images exceeds a first window obscuration threshold and that the first and second gradient images exceed a second window obscuration threshold and, in response, providing an alert that the optical window is obscured.

Example 158

The method of any one of Examples 136 to 157, further comprising detecting a target species based on image data from said plurality of spatially and spectrally distinct optical channels.

Example 159

The method of any one of Examples 136 to 158, further comprising performing spectral analysis to detect said target species.

Example 160

The method of any one of Examples 136 to 159, further comprising adjusting image data from the plurality of optical channels to compensate for effects of attenuation due to the window being obscured.

Example 161

The method of any one of Examples 136 to 160, further comprising de-emphasizing one or more frames of image data from the plurality of optical channels in the determination of the presence of a target species.

Example 162

The method of any one of Examples 136 to 161, further comprising sending an alert when the window is obscured.

Any of Examples 1 to 162 can include any of the features described above (for example, any of the features in Examples 1 to 162).

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

FIG. 8A is a perspective view of an example mobile infrared imaging system in which two of the optical channels are configured as window obscuration sensors.

Like reference numbers and designations in the various drawings indicate like elements.

DETAILED DESCRIPTION

I. Overview of Various Embodiments

Figure 1:
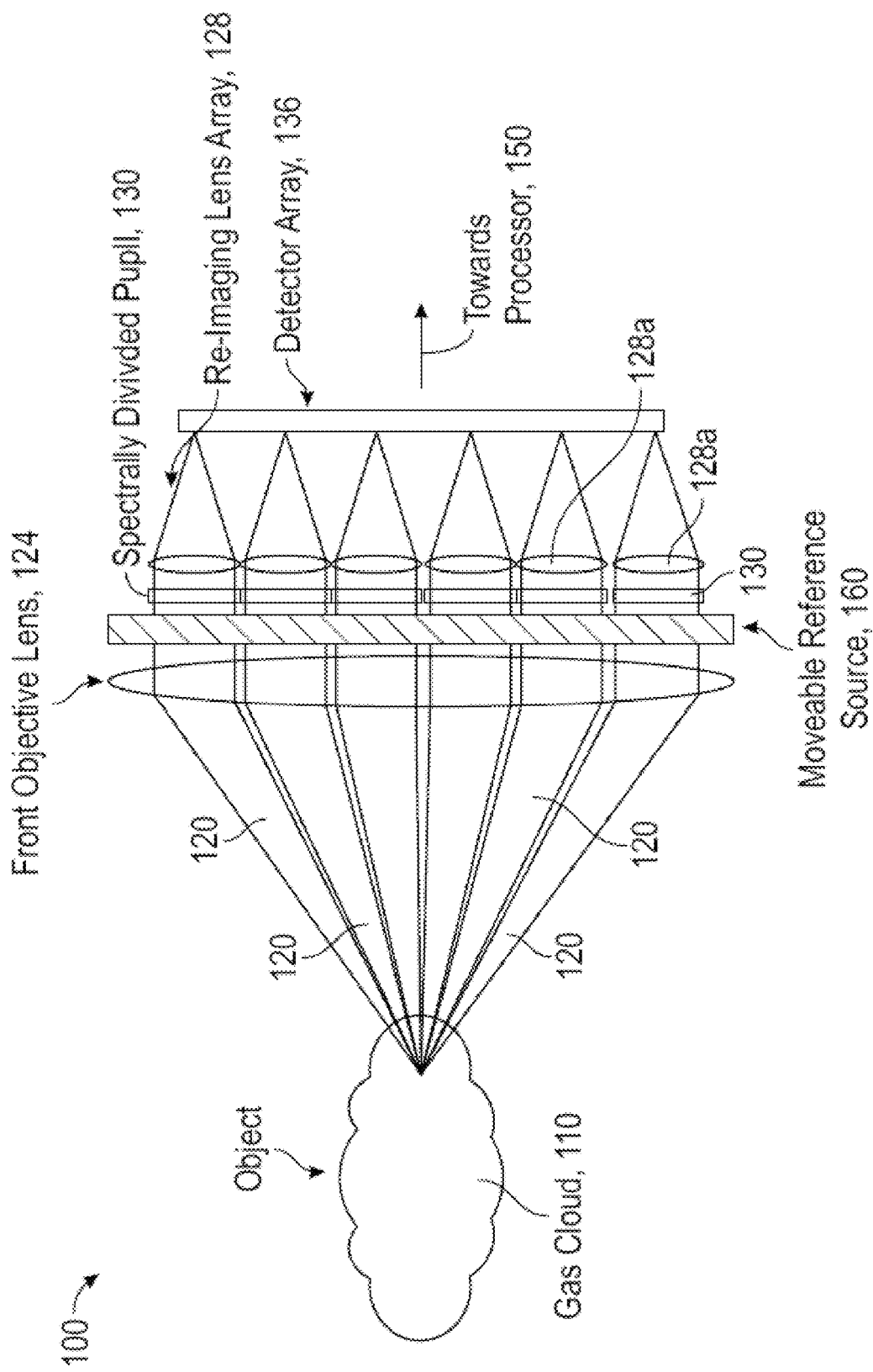
FIG. 1 shows an embodiment of an imaging system including a common front objective lens that has a pupil divided spectrally and re-imaged with a plurality of lenses onto an infrared focal plane array (FPA), sometimes referred to here as a divided-aperture infrared spectral imaging (DAISI) system.

The following description is directed to certain implementations for the purposes of describing the innovative aspects of this disclosure. However, a person having ordinary skill in the art will readily recognize that the teachings herein can be applied in a multitude of different ways. The described implementations may be implemented in any device, apparatus, or system that can be configured to operate as an imaging system such as in an infra-red imaging system. The methods and systems described herein can be included in or associated with a variety of devices such as, but not limited to devices used for visible and infrared spectroscopy, multispectral and hyperspectral imaging devices used in oil and gas exploration, refining, and transportation, agriculture, remote sensing, defense and homeland security, surveillance, astronomy, environmental monitoring, etc. The methods and systems described herein have applications in a variety of fields including but not limited to agriculture, biology, physics, chemistry, defense and homeland security, environment, oil and gas industry, etc. The teachings are not intended to be limited to the implementations depicted solely in the Figures, but instead have wide applicability as will be readily apparent to one having ordinary skill in the art.

The spectral image of the scene can be represented as a three-dimensional data cube where two axes of the cube represent two spatial dimensions of the scene and a third axis of the data cube represents spectral information of the scene in different wavelength regions. The data cube can be processed using mathematical methods to obtain information about the scene. Some of the existing spectral imaging systems generate the data cube by scanning the scene in the spatial domain (e.g., by moving a slit across the horizontal and vertical dimensions of the scene) and/or spectral domain. Such scanning approaches acquire only a portion of the full data cube at a time. These portions of the full data cube are stored and then later processed to generate a full data cube.

Various embodiments disclosed herein describe a divided-aperture infrared spectral imaging (DAISI) system that is structured and adapted to provide identification of target chemical contents of the imaged scene. The system is based on spectrally-resolved imaging and can provide such identification with a single-shot (also referred to as a snapshot) comprising a plurality of images having different wavelength compositions that are obtained generally simultaneously. Without any loss of generality, snapshot refers to a system in which most of the data elements that are collected are continuously viewing the light emitted from the scene. In contrast in scanning systems, at any given time only a minority of data elements are continuously viewing a scene, followed by a different set of data elements, and so on, until the full dataset is collected. Relatively fast operation can be achieved in a snapshot system because it does not need to use spectral or spatial scanning for the acquisition of infrared (IR) spectral signatures of the target chemical contents. Instead, IR detectors (such as, for example, infrared focal plane arrays or FPAs) associated with a plurality of different optical channels having different wavelength profiles can be used to form a spectral cube of imaging data. Although spectral data can be obtained from a single snapshot comprising multiple simultaneously acquired images corresponding to different wavelength ranges, in various embodiments, multiple snap shots may be obtained. In various embodiments, these multiple snapshots can be averaged. Similarly, in certain embodiments multiple snap shots may be obtained and a portion of these can be selected and possibly averaged. Also, in contrast to commonly used IR spectral imaging systems, the DAISI system does not require cooling. Accordingly, it can advantageously use uncooled infrared detectors. For example, in various implementations, the imaging systems disclosed herein do not include detectors configured to be cooled to a temperature below 300 Kelvin. As another example, in various implementations, the imaging systems disclosed herein do not include detectors configured to be cooled to a temperature below 273 Kelvin. As yet another example, in various implementations, the imaging systems disclosed herein do not include detectors configured to be cooled to a temperature below 250 Kelvin. As another example, in various implementations, the imaging systems disclosed herein do not include detectors configured to be cooled to a temperature below 200 Kelvin.

Implementations disclosed herein provide several advantages over existing IR spectral imaging systems, most if not all of which may require FPAs that are highly sensitive and cooled in order to compensate, during the optical detection, for the reduction of the photon flux caused by spectrum-scanning operation. The highly sensitive and cooled FPA systems are expensive and require a great deal of maintenance. Since various embodiments disclosed herein are configured to operate in single-shot acquisition mode without spatial and/or spectral scanning, the instrument can receive photons from a plurality of points (e.g., every point) of the object substantially simultaneously, during the single reading. Accordingly, the embodiments of imaging system described herein can collect a substantially greater amount of optical power from the imaged scene (for example, an order of magnitude more photons) at any given moment in time especially in comparison with spatial and/or spectral scanning systems. Consequently, various embodiments of the imaging systems disclosed herein can be operated using uncooled detectors (for example, FPA unit including an array of microbolometers) that are less sensitive to photons in the IR but are well fit for continuous monitoring applications. For example, in various implementations, the imaging systems disclosed herein do not include detectors configured to be cooled to a temperature below 300 Kelvin. As another example, in various implementations, the imaging systems disclosed herein do not include detectors configured to be cooled to a temperature below 273 Kelvin. As yet another example, in various implementations, the imaging systems disclosed herein do not include detectors configured to be cooled to a temperature below 250 Kelvin. As another example, in various implementations, the imaging systems disclosed herein do not include detectors configured to be cooled to a temperature below 200 Kelvin. Imaging systems including uncooled detectors can be capable of operating in extreme weather conditions, require less power, are capable of operation during day and night, and are less expensive. Some embodiments described herein can also be less susceptible to motion artifacts in comparison with spatially and/or spectrally scanning systems which can cause errors in either the spectral data, spatial data, or both.

In various embodiments disclosed herein, the DAISI system can be mobile. For example, the DAISI system can be configured to be worn or carried by a person, e.g., the DAISI system can be miniaturized to fit in a relatively small housing or compartment. For example, the components of the DAISI system can be sized and shaped to fit within small dimensions and can have a mass sufficiently small to enable the human user to carry or wear the system without undue exertion. As explained herein, in some embodiments, the DAISI system can be sized and shaped to fit within a volume of less than about 300 cubic inches, or in some embodiments, less than about 200 cubic inches. In still other embodiments, the DAISI system can be sized and shaped to fit within a volume less than about 100 cubic inches. For example, in some arrangements, the DAISI system can be sized and shaped to fit within a volume in a range of about 50 cubic inches to about 300 cubic inches. In other arrangements, the DAISI system can be sized and shaped to fit within a volume in a range of about 80 cubic inches to about 200 cubic inches.

Advantageously, such a portable and/or wearable DAISI system can enable the user to monitor installations in remote locations and to detect the presence of various gases (e.g., poisonous gases) in real-time. Further, the portable DAISI system can enable the user to travel to different installations to monitor the presence of gases or chemicals in multiple locations. For example, the user may travel to an oil drilling installation in which oil is pumped from the ground. The user can carry or attach the portable DAISI system to his or her clothing or body (e.g., by way of a clip, hat, etc.) and can activate the system while he or she is on-site. Optical components on board the portable DAISI system can capture one or more snapshot multispectral images of portions of the installation susceptible to gas or chemical leaks. Computing units on board the portable DAISI system can process the captured multispectral image data to detect and/or classify gases or chemicals present at the site. A communications module can notify the user of the detected gases. For example, in various embodiments, the communications module can send a notification to a user interface (such as a set of computing eyeglasses, a mobile computing device such as a mobile smartphone, a tablet computing device, a laptop computing device, or any other suitable interface), and the user interface can display information about the detected gases to the user in real-time, e.g., at the oil drilling installation.

II. Examples of Divided Aperture Infrared Spectral Imager Systems

FIG. 1 provides a diagram schematically illustrating spatial and spectral division of incoming light by an embodiment 100 of a divided aperture infrared spectral imager (DAISI) system that can image an object 110 possessing IR spectral signature(s). The system 100 includes a front objective lens 124, an array of optical filters 130, an array of reimaging lenses 128 and a detector array 136. In various embodiments, the detector array 136 can include a single FPA or an array of FPAs. Each detector in the detector array 136 can be disposed at the focus of each of the lenses in the array of reimaging lenses 128. In various embodiments, the detector array 136 can include a plurality of photo-sensitive devices. In some embodiments, the plurality of photo-sensitive devices may comprise a two-dimensional imaging sensor array that is sensitive to radiation having wavelengths between 1 µm and 20 µm (for example, in near infra-red wavelength range, mid infra-red wavelength range, or long infra-red wavelength range). In various embodiments, the plurality of photo-sensitive devices can include CCD or CMOS sensors, bolometers, microbolometers or other detectors that are sensitive to infra-red radiation.

An aperture of the system 100 associated with the front objective lens system 124 is spatially and spectrally divided by the combination of the array of optical filters 130 and the array of reimaging lenses 128. In various embodiments, the combination of the array of optical filters 130 and the array of reimaging lenses 128 can be considered to form a spectrally divided pupil that is disposed forward of the optical detector array 136. The spatial and spectral division of the aperture into distinct aperture portions forms a plurality of optical channels 120 along which light propagates. In various embodiments, the array 128 of re-imaging lenses 128a and the array of spectral filters 130 which respectively correspond to the distinct optical channels 120. The plurality of optical channels 120 can be spatially and/or spectrally distinct. The plurality of optical channels 120 can be formed in the object space and/or image space. In one implementation, the distinct channels 120 may include optical channels that are separated angularly in space. The array of spectral filters 130 may additionally include a filter-holding aperture mask (comprising, for example, IR light-blocking materials such as ceramic, metal, or plastic). Light from the object 110 (for example a cloud of gas), the optical properties of which in the IR are described by a unique absorption, reflection and/or emission spectrum, is received by the aperture of the system 100. This light propagates through each of the plurality of optical channels 120 and is further imaged onto the optical detector array 136. In various implementations, the detector array 136 can include at least one FPA. In various embodiments, each of the re-imaging lenses 128a can be spatially aligned with a respectively-corresponding spectral region. In the illustrated implementation, each filter element from the array of spectral filters 130 corresponds to a different spectral region. Each re-imaging lens 128a and the corresponding filter element of the array of spectral filter 130 can coincide with (or form) a portion of the divided aperture and therefore with respectively-corresponding spatial channel 120. Accordingly, in various embodiment an imaging lens 128a and a corresponding spectral filter can be disposed in the optical path of one of the plurality of optical channels 120. Radiation from the object 110 propagating through each of the plurality of optical channels 120 travels along the optical path of each re-imaging lens 128a and the corresponding filter element of the array of spectral filter 130 and is incident on the detector array (e.g., FPA component) 136 to form a single image (e.g., sub-image) of the object 110. The image formed by the detector array 136 generally includes a plurality of sub-images formed by each of the optical channels 120. Each of the plurality of sub-images can provide different spatial and spectral information of the object 110. The different spatial information results from some parallax because of the different spatial locations of the smaller apertures of the divided aperture. In various embodiments, adjacent sub-images can be characterized by close or substantially equal spectral signatures. The detector array (e.g., FPA component) 136 is further operably connected with a processor 150 (not shown). The processor 150 can be programmed to aggregate the data acquired with the system 100 into a spectral data cube. The data cube represents, in spatial (x, y) and spectral (λ) coordinates, an overall spectral image of the object 110 within the spectral region defined by the combination of the filter elements in the array of spectral filters 130. Additionally, in various embodiments, the processor or processing electronics 150 may be programmed to determine the unique absorption characteristic of the object 110. Also, the processor/processing electronics 150 can, alternatively or in addition, map the overall image data cube into a cube of data representing, for example, spatial distribution of concentrations, c, of targeted chemical components within the field of view associated with the object 110.

Various implementations of the embodiment 100 can include an optional moveable temperature-controlled reference source 160 including, for example, a shutter system comprising one or more reference shutters maintained at different temperatures. The reference source 160 can include a heater, a cooler or a temperature-controlled element configured to maintain the reference source 160 at a desired temperature. For example, in various implementations, the embodiment 100 can include two reference shutters maintained at different temperatures. The reference source 160 is removably and, in one implementation, periodically inserted into an optical path of light traversing the system 100 from the object 110 to the detector array (e.g., FPA component) 136 along at least one of the channels 120. The removable reference source 160 thus can block such optical path. Moreover, this reference source 160 can provide a reference IR spectrum to recalibrate various components including the detector array 136 of the system 100 in real time. The configuration of the moveable reference source 160 is further discussed below.

In the embodiment 100, the front objective lens system 124 is shown to include a single front objective lens positioned to establish a common field-of-view (FOV) for the reimaging lenses 128a and to define an aperture stop for the whole system. In this specific case, the aperture stop substantially spatially coincides with and/or is about the same size as or slightly larger than the plurality of smaller limiting apertures corresponding to different optical channels 120. As a result, the positions for spectral filters of the different optical channels 120 coincide with the position of the aperture stop of the whole system, which in this example is shown as a surface between the lens system 124 and the array 128 of the reimaging lenses 128a. In various implementations, the lens system 124 can be an objective lens 124. However, the objective lens 124 is optional and various embodiments of the system 100 need not include the objective lens 124. In various embodiments, the objective lens 124 can slightly shift the images obtained by the different detectors in the array 136 spatially along a direction perpendicular to optical axis of the lens 124, thus the functionality of the system 100 is not necessarily compromised when the objective lens 124 is not included. Generally, however, the field apertures corresponding to different optical channels may be located in the same or different planes. These field apertures may be defined by the aperture of the reimaging lens 128a and/or filters in the divided aperture 130 in certain implementations. In one implementation, the field apertures corresponding to different optical channels can be located in different planes and the different planes can be optical conjugates of one another. Similarly, while all of the filter elements in the array of spectral filters 130 of the embodiment 100 are shown to lie in one plane, generally different filter elements of the array of spectral filter 130 can be disposed in different planes. For example, different filter elements of the array of spectral filters 130 can be disposed in different planes that are optically conjugate to one another. However, in other embodiments, the different filter elements can be disposed in non-conjugate planes.

Figure 2:
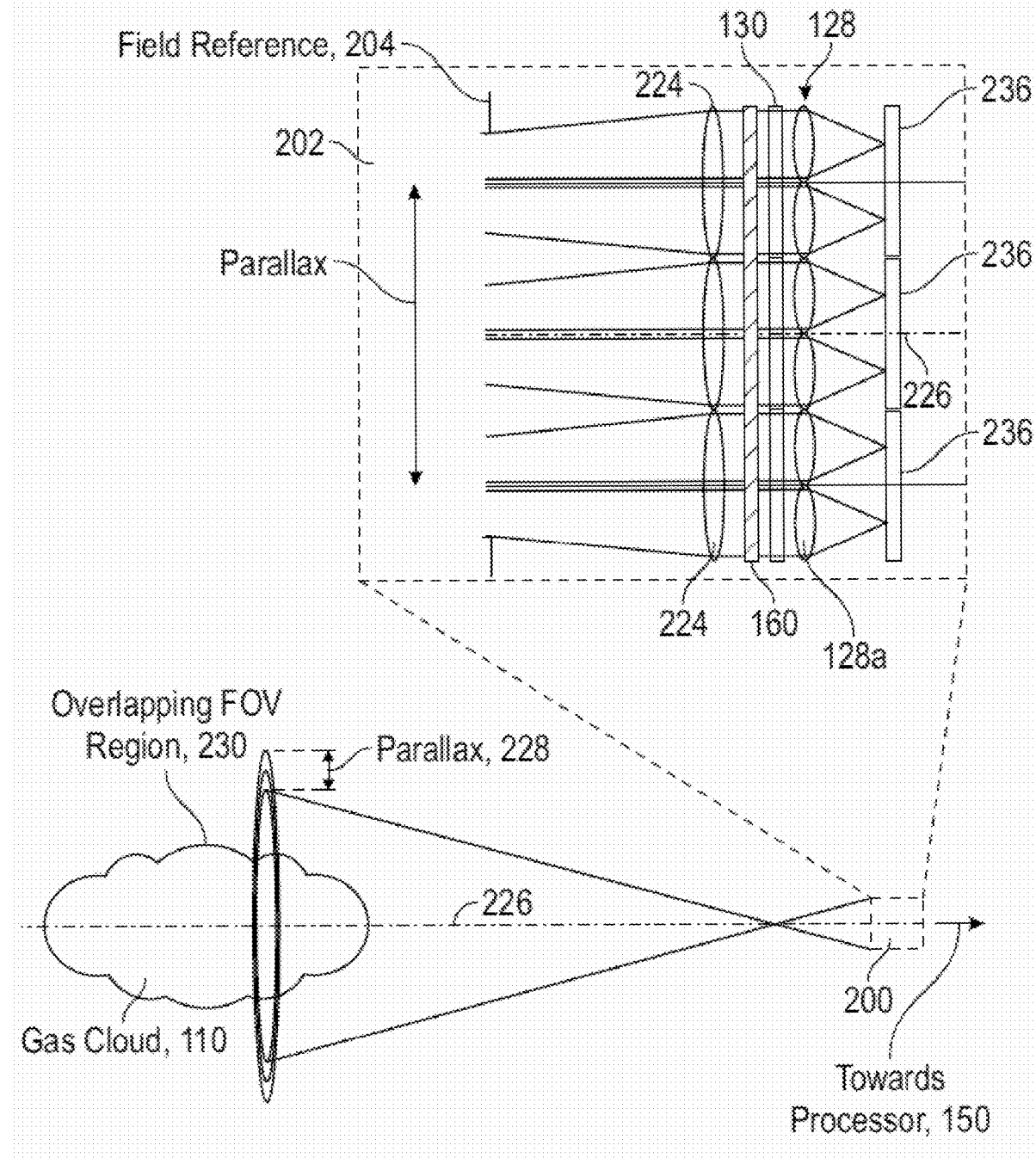
FIG. 2 shows an embodiment with a divided front objective lens and an array of infrared sensing FPAs.

In contrast to the embodiment 100, the front objective lens 124 need not be a single optical element, but instead can include a plurality of lenses 224 as shown in an embodiment 200 of the DAISI imaging system in FIG. 2. These lenses 224 are configured to divide an incoming optical wavefront from the object 110. For example, the array of front objective lenses 224 can be disposed so as to receive an IR wavefront emitted by the object that is directed toward the DAISI system. The plurality of front objective lenses 224 divide the wavefront spatially into non-overlapping sections. FIG. 2 shows three objective lenses 224 in a front optical portion of the optical system contributing to the spatial division of the aperture of the system in this example. The plurality of objective lenses 224, however, can be configured as a two-dimensional (2D) array of lenses. FIG. 2 presents a general view of the imaging system 200 and the resultant field of view of the imaging system 200. An exploded view 202 of the imaging system 200 is also depicted in greater detail in a figure inset of FIG. 2. As illustrated in the detailed view 202, the embodiment of the imaging system 200 includes a field reference 204 at the front end of the system. The field reference 204 can be used to truncate the field of view. The configuration illustrated in FIG. 2 has an operational advantage over embodiment 100 of FIG. 1 in that the overall size and/or weight and/or cost of manufacture of the embodiment 200 can be greatly reduced because the objective lens is smaller. Each pair of the lenses in the array 224 and the array 128 is associated with a field of view (FOV). Each pair of lenses in the array 224 and the array 128 receives light from the object from a different angle. Accordingly, the FOV of the different pairs of lenses in the array 224 and the array 128 do not completely overlap as a result of parallax. As the distance between the imaging system 200 (portion 202) and the object 110 increases, the overlapping region 230 between the FOVs of the individual lenses 224 increases while the amount of parallax 228 remains approximately the same, thereby reducing its effect on the system 200. When the ratio of the parallax-to-object-distance is substantially equal to the pixel-size-to-system-focal-length ratio then the parallax effect may be considered to be negligible and, for practical purposes, no longer distinguishable. While the lenses 224 are shown to be disposed substantially in the same plane, optionally different objective lenses in the array of front objective lenses 224 can be disposed in more than one plane. For example, some of the individual lenses 224 can be displaced with respect to some other individual lenses 224 along the axis 226 (not shown) and/or have different focal lengths as compared to some other lenses 224. As discussed below, the field reference 204 can be useful in calibrating the multiple detectors 236.

In one implementation, the front objective lens system such as the array of lenses 224 is configured as an array of lenses integrated or molded in association with a monolithic substrate. Such an arrangement can reduce the costs and complexity otherwise accompanying the optical adjustment of individual lenses within the system. An individual lens 224 can optionally include a lens with varying magnification. As one example, a pair of thin and large diameter Alvarez plates can be used in at least a portion of the front objective lens system. Without any loss of generality, the Alvarez plates can produce a change in focal length when translated orthogonally with respect to the optical beam.

In further reference to FIG. 1, the detector array 136 (e.g., FPA component) configured to receive the optical data representing spectral signature(s) of the imaged object 110 can be configured as a single imaging array (e.g., FPA) 136. This single array may be adapted to acquire more than one image (formed by more than one optical channel 120) simultaneously. Alternatively, the detector array 136 may include a FPA unit. In various implementations, the FPA unit can include a plurality of optical FPAs. At least one of these plurality of FPAs can be configured to acquire more than one spectrally distinct image of the imaged object. For example, as shown in the embodiment 200 of FIG. 2, in various embodiments, the number of FPAs included in the FPA unit may correspond to the number of the front objective lenses 224. In the embodiment 200 of FIG. 2, for example, three FPAs 236 are provided corresponding to the three objective lenses 224. In one implementation of the system, the FPA unit can include an array of microbolometers. The use of multiple microbolometers advantageously allows for an inexpensive way to increase the total number of detection elements (i.e. pixels) for recording of the three-dimensional data cube in a single acquisition event (i.e. one snapshot). In various embodiments, an array of microbolometers more efficiently utilizes the detector pixels of the array of FPAs (e.g., each FPA) as the number of unused pixels is reduced, minimized and/or eliminated between the images that may exist when using a single microbolometer.

Figures 3A, 3B:
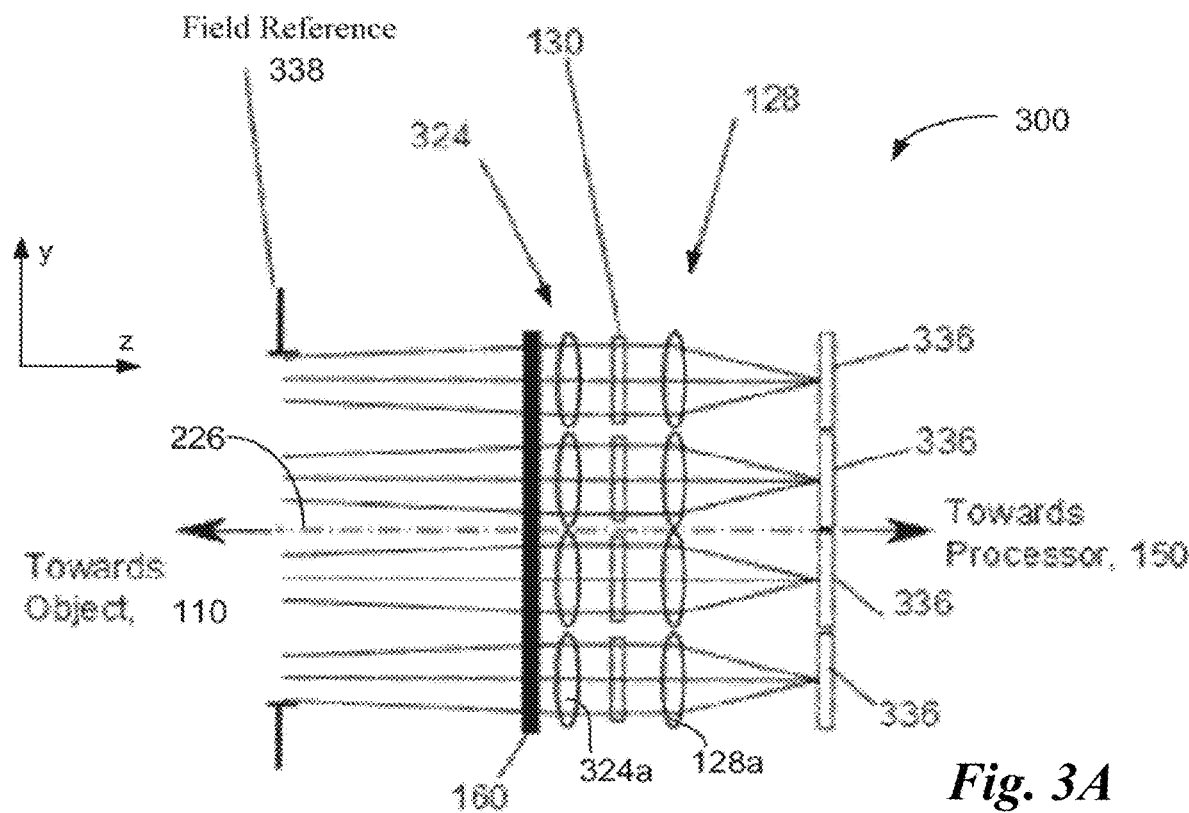
FIG. 3A represents an embodiment employing an array of front objective lenses operably matched with the re-imaging lens array.
FIG. 3B illustrates a two-dimensional array of optical components corresponding to the embodiment of FIG. 3A.

FIG. 3A illustrates schematically an embodiment 300 of the imaging system in which the number of the front objective lenses 324a in the lens array 324, the number of re-imaging lenses 128a in the lens array 128, and the number of FPAs 336 are the same. So configured, each combination of respectively corresponding front objective lens 324, re-imaging lens 128a, and FPAs 336 constitutes an individual imaging channel. Such a channel is associated with acquisition of the IR light transmitted from the object 110 through an individual filter element of the array of optical filters 130. A field reference 338 of the system 300 is configured to have a uniform temperature across its surface and be characterized by a predetermined spectral curve of radiation emanating therefrom. In various implementations, the field reference 338 can be used as a calibration target to assist in calibrating or maintaining calibration of the FPA. Accordingly, in various implementations, the field reference 338 is used for dynamically adjusting the data output from each FPA 336 after acquisition of light from the object 110. This dynamic calibration process helps provide that output of the different (e.g., most, or each of the) FPA 336 represents correct acquired data, with respect to the other FPAs 336 for analysis, as discussed below in more detail.

FIG. 3B illustrates the plan view perpendicular to the axis 226 of an embodiment 300 of the imaging system illustrated in FIG. 3A. For the embodiment shown in FIG. 3B, the optical components (e.g., objective lenses 324a, filter elements of the array of spectral filters 130, re-imaging lenses 128a and FPA units 336) are arranged as a 4×3 array. In one implementation, the 4×3 array 340 of optical components (lenses 324a, 128a; detector elements 336) is used behind the temperature controlled reference target 160. The field reference aperture 338 can be adapted to obscure and/or block a peripheral portion of the bundle of light propagating from the object 110 towards the FPA units 336. As a result, the field reference 338 obscures and/or blocks the border or peripheral portion(s) of the images of the object 110 formed on the FPA elements located along the perimeter 346 of the detector system. Generally, two elements of the FPA unit will produce substantially equal values of digital counts when they are used to observe the same portion of the scene in the same spectral region using the same optical train. If any of these input parameters (for example, scene to be observed, spectral content of light from the scene, or optical elements delivering light from the scene to the two detector elements) differ, the counts associated with the elements of the FPA unit will differ as well. Accordingly, and as an example, in a case when the two FPAs of the FPA unit 336 (such as those denoted as #6 and #7 in FIG. 3B) remain substantially un-obscured by the field reference 338, the outputs from these FPAs can be dynamically adjusted to the output from one of the FPAs located along perimeter 346 (such as, for example, the FPA element #2 or FPA element #11) that processes light having similar spectral characteristics.

III. Examples of a Mobile DAISI System

The DAISI systems disclosed herein can be configured to be installed at a suitable location on a long-term basis, according to some embodiments. For example, the DAISI systems disclosed in Section II above can be affixed to a fixture mounted to the ground at a location to continuously or periodically monitor the presence of gases or chemicals at the location. In some embodiments, for example, the DAISI systems can be attached to a pole, post, or any suitable fixture at the location to be monitored. In such arrangements, the DAISI system can continuously or periodically capture multispectral, multiplexed image data of the scene, and an on-board or remote computing unit can process the captured image data to identify or characterize gases or chemicals at the location. A communications module can communicate data relating to the identified gases or chemicals to any suitable external system, such as a central computing server, etc. For such long-term installations of the DAISI system, the installation site may include a power source (e.g., electrical transmission lines connected to a junction box at the site) and network communications equipment (e.g., network wiring, routers, etc.) to provide network communication between the DAISI system and the external systems.

It can be advantageous to provide a mobile DAISI system configured to be worn or carried by a user. For example, it may be unsuitable or undesirable to install a DAISI system at some locations on a long-term basis. As an example, some oil well sites may not have sufficient infrastructure, such as power sources or network communication equipment, to support the DAISI system. In addition, it can be challenging to move the DAISI system from site to site to monitor different locations. For example, installing and removing the DAISI system from a site for transport may involve substantial effort and time for the user when the system is connected to infrastructure at the site to be monitored. Accordingly, it can be desirable to provide a DAISI system that can be used independently of the facilities or infrastructure at the site to be monitored. Furthermore, it can be advantageous to implement the DAISI system in a form factor and with a weight that can be carried or worn by a user. For example, a mobile DAISI system can enable the user to easily transport the system from site-to-site, while monitoring the presence of gases or chemicals in real-time.

It should be appreciated that each of the systems disclosed herein can be used to monitor potential gas leaks in any suitable installation site, including, without limitation, drilling rigs, refineries, pipelines, transportations systems, ships or other vessels (such as off-shore oil rigs, trains, tanker trucks, petro-chemical plants, chemical plants, etc. In addition, each of the embodiments and aspects disclosed and illustrated herein such as above, e.g., with respect to FIGS. 1-3B, can be used in combination with each of the embodiments disclosed and illustrated herein with respect to FIGS. 4A-6C.

Figure 4A:
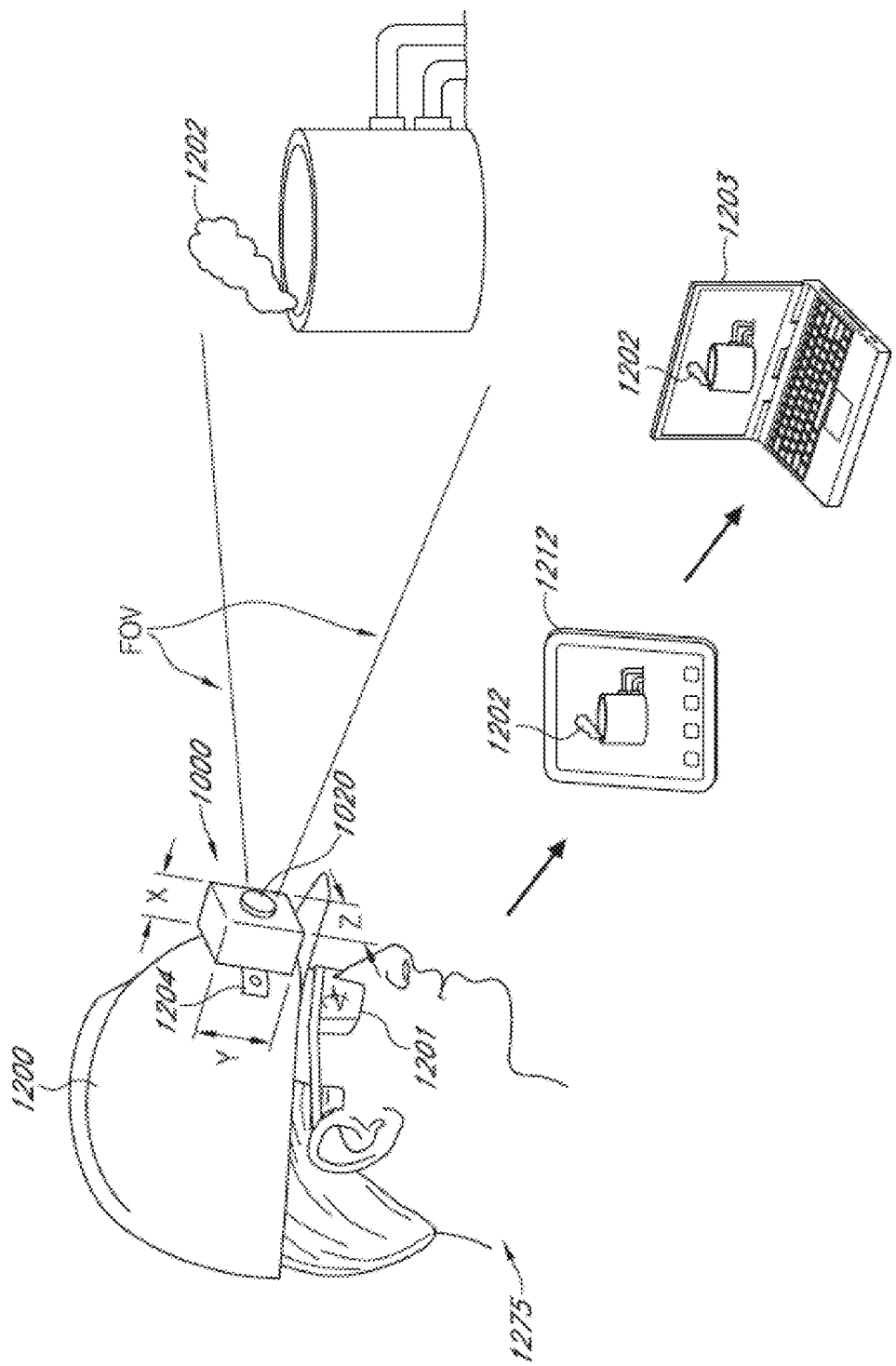
FIG. 4A is a schematic diagram illustrating a mobile infrared imaging system configured to be carried or worn by a human user.

FIG. 4A is a schematic diagram illustrating a mobile infrared imaging system 1000 (e.g., a mobile or portable DAISI system) configured to be carried or worn by a human user 1275. The user 1275 may wear a hat or helmet 1200 when he travels to a site to be monitored, such as an oil well site, a refinery, etc. The system 1000 shown in FIG. 4A is attached to the helmet 1200 by way of a support 1204 that securely mounts the system 1000 to the helmet 1200. For example, the support 1204 can comprise a fastener, a strap, or any other suitable structure. Advantageously, mounting the system 1000 to the helmet 1200 can enable the user 1275 to capture images within the system's field of view (FOV) by turning his head to face a particular location to be monitored. For example, the user 1275 can walk through the site and can capture video images of each portion of the site, e.g., various structures that may be susceptible to gas or chemical leaks, such as valves, fittings, etc. Thus, in the embodiment shown in FIG. 4A, the user 1275 can image each portion of the site by facing the area to be imaged and ensuring that the system 1000 is activated. In addition, by mounting the system 1000 to the user's helmet 1200, the user 1275 may use his hands for other tasks while the system 1000 images the site. Although the system 1000 of FIG. 4A is shown as being mounted to the user's helmet 1200, it should be appreciated that the system 1000 can instead be worn on other parts of the user's clothing or can be carried by the user, e.g., in a bag, case, or other suitable container. Furthermore, in some embodiments, a wind sensor can be provided to the user, e.g., on the user's clothing and/or on or near the system 1000. The wind sensor can be used to estimate wind conditions at the installation site, which can be used to improve the detection of gas leaks. In other embodiments, the system 1000 can be coupled to or formed with a housing that defines a "gun"-like structure which can be aimed or pointed by the user in a particular direction.

As explained herein, a gas cloud 1202 emitted from a structure at the site can be imaged by pointing the system 1000 towards the gas cloud 1202 and capturing an image of the gas cloud 1202 when the cloud 1202 is within the FOV of the system 1000. Unlike other systems, the system 1000 can capture multispectral image data of a single scene over a range of IR wavelengths with a single snapshot, as explained in further detail herein. The single snapshot can be captured in a short timeframe, e.g., less than about 3 seconds, less than about 2 seconds, or less than about 1.5 seconds (for example, in about 1 second, in some embodiments). The single snapshot can be captured in greater than about 5 milliseconds, greater than about 0.2 seconds, or greater than about 0.5 seconds. The captured image data can be processed on board the system 1000 by a processing unit, as explained in further detail herein. For example, the processing unit can process the image data from the different optical channels and can compare the captured spectral information with a database of known chemicals to identify and/or characterize the gases that are included in the gas cloud 1202.

A communications module on board the system 1000 can transmit information relating to the identified gases or chemicals to any suitable external device. For example, the communications module can wirelessly communicate (e.g., by Bluetooth, WiFi, etc.) the information to a suitable mobile computing device, such as an electronic eyewear apparatus 1201, a tablet computing device 1212, a mobile smartphone, a laptop or notebook computer 1203, or any other suitable mobile computing device. In some embodiments, if a gas cloud is detected, the system 1000 can warn the user by way of sending a signal to the mobile device (e.g., tablet computing device 1212 or a mobile smartphone. The mobile device can emit an audible ring and/or can vibrate to notify the user of a potential gas leak. In the embodiment of FIG. 4A, the electronic eyewear apparatus 1201 can include a user interface comprising a display that the user 1275 can view in real-time as he visits the site. In some embodiments, the electronic eyewear apparatus 1201 comprises eyewear that includes a display. The electronics eyewear apparatus 1201 can be further configured to present images from this display to the wearer. The electronics eyewear apparatus 1201 may for example include projection optics that projects the image into the eye. The electronic eyewear apparatus 1201 may comprise heads up display optics the presents the image on the lens portion(s) of the eyewear so that the wearer can view the image and also see through the eyewear and peer at objects in the distance. Other configurations are possible. In some arrangements, the eyewear apparatus 1201 can comprise a Google Glass device, sold by Google, Inc., of Mountain View, Calif.

The processing unit can configure the processed image data such that the types of identified gases are displayed to the user 1275 on the display of the eyewear apparatus 1201. For example, in some embodiments, color-coded data may represent different types of gases or concentrations of a particular gas, and may be overlaid on a visible light image of the scene. For example, the color-coded data and image of the gas cloud can be seen by the user on the electronic eyewear apparatus 1201. In various embodiments, text data and statistics about the composition of the gas cloud 1202 may also be displayed to the user 1275. Thus, the user 1275 can walk the site and can view the different types of gases in the gas cloud 1202 substantially in real-time. Advantageously, such real-time display of the composition of the gas cloud 1202 can enable the user 1275 to quickly report urgent events, such as the leakage of a toxic gas or chemical. In some embodiments, detection of a toxic leak can trigger an alarm, which may cause emergency personnel to help evacuate the site and/or fix the leak.

In some embodiments, the processed image data can be transmitted from the system 1000 to the tablet computing device 1212, laptop computer 1203, and/or smartphone. The user 1275 can interact with the table computing device 1212 or laptop computer 1203 to conduct additional analysis of the imaged and processed gas cloud 1202. Furthermore, information about the gas cloud (including the processed data and/or the raw image data) may also be transmitted to a central server for centralized collection, processing, and analysis. In various arrangements, a global positioning system (GPS) module can also be installed on board the system 1000 and/or on the mobile computing device (such as a tablet computing device, smartphone, etc.). The GPS module can identify the coordinates of the user 1275 when a particular image is captured. The location data for the captured image data can be stored on the central server for further analysis.

Thus, the system 1000 shown in FIG. 4A can enable the user 1275 to image multiple locations of a particular site to be monitored, such as an oil well site. Advantageously, the optical components, the processing components, and the communications components of the system 1000 can be integrated within a relatively small housing that can be carried or worn by the user 1275. For example, in various embodiments, the system 1000 does not include complex mechanical components for movement, such as gimbals, actuators, motors, etc. Without such components, the size of the system 1000 can be reduced relative to other systems.

Unlike other systems, in which the system components are bulky or are assembled over a large form factor, the mobile system 1000 can be sized and shaped in such a manner so as to be easily moved and manipulated when the user 1275 moves about the site. Indeed, it can be very challenging to integrate the various system components in a small form-factor. Advantageously, the systems 1000 can be worn or carried by a human user. For example, the components of the system 1000 can be contained together in a data acquisition and processing module 1020, which may include a housing to support the system components. The components of the system 1000 (including the optical or imaging components, the focal plane array, the on-board processing electronics, and the communications components) may be packaged or assembled in the data acquisition and processing module 1020 and may occupy a volume less than about 300 cubic inches, less than about 200 cubic inches, or less than about 100 cubic inches. In various embodiments, the components of the system 1000 (including the optical or imaging components, the focal plane array, the on-board processing electronics, and the communications components) may be packaged or assembled in the data acquisition and processing module 1020 and may occupy a volume greater than about 2 cubic inches, or greater than about 16 cubic inches.

The data acquisition and processing module 1020 (with the system components mounted therein or thereon) may be sized and shaped to fit within a box-shaped boundary having dimensions X×Y×Z. For example, the data acquisition and processing module 1020, including the imaging optics, focal plane array, and on board processing electronics, may be included in a package that is sized and shaped to fit within the box-shaped boundary having dimensions X×Y×Z. This package may also contain a power supply, such as a battery and/or solar module. In some embodiments, the data acquisition and processing module 1020 (including the imaging optics, focal plane array, and on board processing electronics may) can be sized and shaped to fit within a box-shaped boundary smaller than 8 inches×6 inches×6 inches. In some embodiments, the data acquisition and processing module 1020 (including the imaging optics, focal plane array, and on board processing electronics may) can be sized and shaped to fit within a box-shaped boundary smaller than 7 inches×5 inches×5 inches, e.g., a box-shaped boundary small than 7 inches×3 inches×3 inches. In some embodiments, the data acquisition and processing module 1020 (including the imaging optics, focal plane array, and on board processing electronics may) can be sized and shaped to fit within a box-shaped boundary smaller than 6 inches×4 inches×4 inches. In some embodiments, the data acquisition and processing module 1020 (including the imaging optics, focal plane array, and on board processing electronics may) can be sized and shaped to fit within a box-shaped boundary smaller than 2 inches×2 inches×6 inches. In some embodiments, the data acquisition and processing module 1020 (including the imaging optics, focal plane array, and on board processing electronics may) can be sized and shaped to fit within a box-shaped boundary having dimensions larger than 4 inches×2 inches×2 inches. In some embodiments, the data acquisition and processing module 1020 (including the imaging optics, focal plane array, and on board processing electronics may) can be sized and shaped to fit within a box-shaped boundary having dimensions larger than 3 inches×3 inches×7 inches. In some embodiments, the data acquisition and processing module 1020 (including the imaging optics, focal plane array, and on board processing electronics may) can be sized and shaped to fit within a box-shaped boundary having dimensions larger than 2 inches×1 inches×1 inches. The data acquisition and processing module 1020 (including the imaging optics, focal plane array, and on board processing electronics may) can have dimensions less than 2 inches×2 inches×6 inches. The data acquisition and processing module 1020 (including the imaging optics, focal plane array, and on board processing electronics may) can have dimensions greater than 1 inches×1 inches×3 inches. The data acquisition and processing module 1020 (including the imaging optics, focal plane array, and on board processing electronics may) can have dimensions greater than 2 inches×2 inches×4 inches. said data acquisition and processing module has dimensions less than 6 inches×3 inches×3 inches. The data acquisition and processing module 1020 (including the imaging optics, focal plane array, and on board processing electronics may) can have dimensions less than 4 inches×3 inches×3 inches. The data acquisition and processing module 1020 (including the imaging optics, focal plane array, and on board processing electronics may) can have dimensions less than 3 inches×2 inches×2 inches. The data acquisition and processing module 1020 (including the imaging optics, focal plane array, and on board processing electronics may) can have dimensions greater than 2 inches×1 inches×1 inches. The data acquisition and processing module 1020 (including the imaging optics, focal plane array, and on board processing electronics may) can have dimensions greater than 1 inches× 0.5 inch×0.5 inch. The data acquisition and processing module 1020 (including the imaging optics, focal plane array, and on board processing electronics may) can have a volume less than 30 cubic inches. The data acquisition and processing module 1020 (including the imaging optics, focal plane array, and on board processing electronics may) can have a volume less than 20 cubic inches. The data acquisition and processing module 1020 (including the imaging optics, focal plane array, and on board processing electronics may) can have a volume less than 15 cubic inches. The data acquisition and processing module 1020 (including the imaging optics, focal plane array, and on board processing electronics may) can have a volume less than 10 cubic inches. The data acquisition and processing module 1020 (including the imaging optics, focal plane array, and on board processing electronics may) can have a volume more than 1 cubic inches. The data acquisition and processing module 1020 (including the imaging optics, focal plane array, and on board processing electronics may) can have a volume more than 4 cubic inches. The data acquisition and processing module 1020 (including the imaging optics, focal plane array, and on board processing electronics may) can have a volume more 5 cubic inches. The data acquisition and processing module 1020 (including the imaging optics, focal plane array, and on board processing electronics may) can have a volume more 10 cubic inches. This package may also contain a power supply, including a battery and/or solar module, a communications module, or both and fit into the above-referenced dimensions. It should be appreciated that the dimensions disclosed herein may not correspond to the directions shown in FIG. 4A with respect to X, Y, and Z.

Moreover, the system 1000 can have a mass and weight sufficiently small so as to enable the user 1275 to easily carry or wear the data acquisition and processing module 1020 at the site. Thus, the embodiment shown in FIG. 4A can be sized and shaped and configured to have a mass that enables a human user to easily and effectively manipulate the system 1000.

Figure 4B:
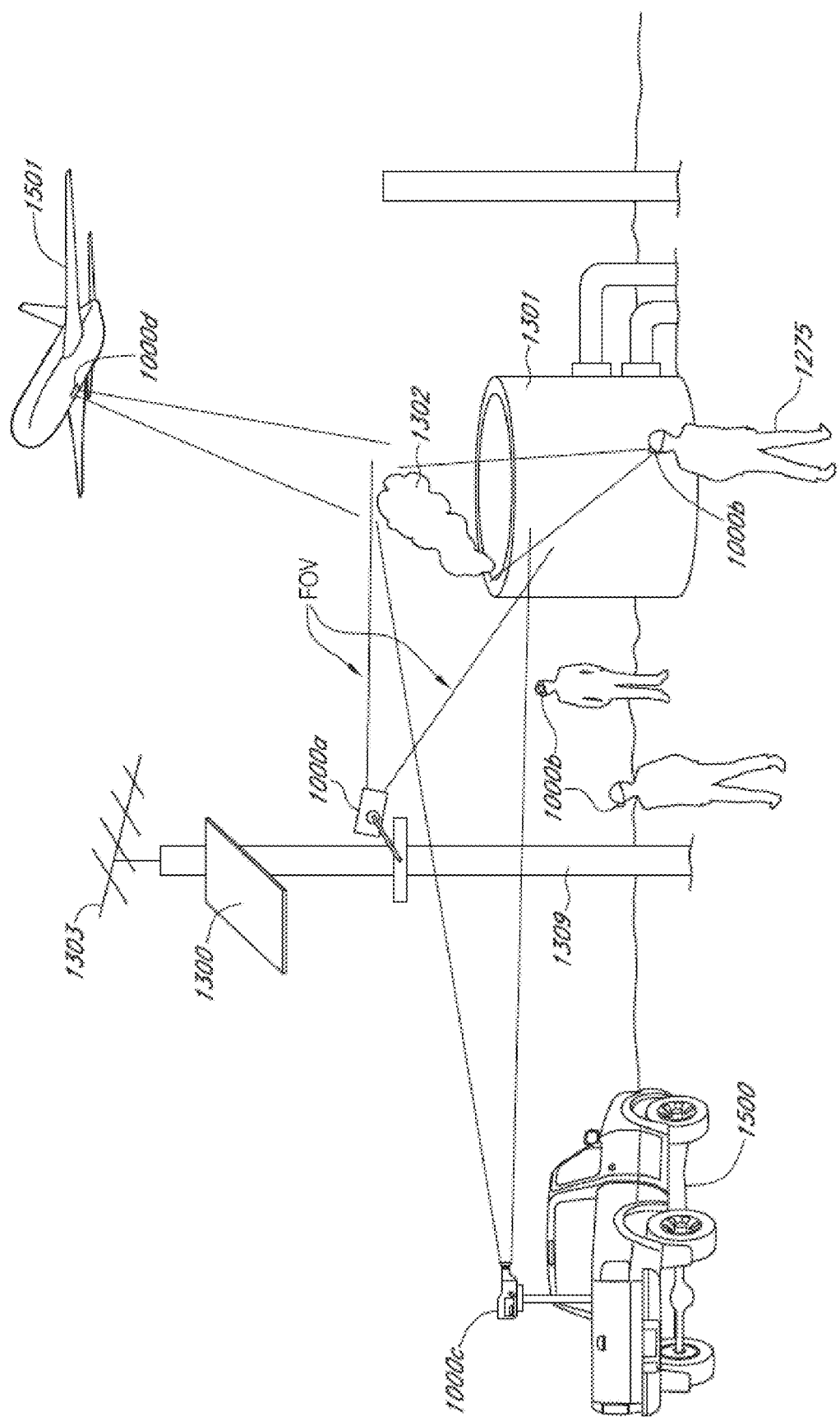
FIG. 4B is a schematic diagram illustrating an installation site that can be monitored by multiple infrared imaging systems.

FIG. 4B is a schematic diagram illustrating an installation site (e.g., an oil well site, etc.) that can be monitored by multiple infrared imaging systems 1000 (e.g., a DAISI system). For example, as shown in FIG. 4B, an imaging system 1000A can be mounted to a pole 1309 or other stationary structure at the site. An imaging system 1000B can be worn or carried by multiple users 1275, an imaging system 1000C can be mounted on a truck 1500, and/or an imaging system 1000D can be mounted on an aerial platform 1501, such as an unmanned aerial vehicle (UAV) or a piloted airplane. In some arrangements, the UAV can comprise an airplane, a helicopter (such as a quad helicopter), etc. The embodiments disclosed herein can utilize the image data captured by any combination of the systems 1000A-1000D at the installation site to image the entire installation site in an efficient manner. Indeed, each installation site can include any suitable number and type of system 1000A-1000D. For example, each installation site can include greater than two systems 1000A-1000D, greater than five systems 1000A-1000D, greater than ten systems 1000A-1000D, greater than twenty systems 1000A-1000D. Each installation site may include less than about 100 systems 1000A-1000D.

For example, the central server can track the real-time locations of each imaging system 1000A-1000D based on the GPS coordinates of the particular system or on predetermined knowledge about the system's stationary location. The distributed nature of the imaging systems 1000A-1000D can provide rich information to the central server about the types and locations of gas leaks or other problems throughout multiple installation sites. Although FIG. 4B illustrates a stationary system 1000A mounted to a fixture, a portable system 1000B to be worn or carried by a human, a truck-based system 1000C, and an aerial-based system 1000D, it should be appreciated that other types of systems may be suitable. For example, in some embodiments, a robotic vehicle or a walking robot can be used as a platform for the systems 1000 disclosed herein. In various embodiments, a floating platform (such as a boat) can be used as a platform for the systems 1000 disclosed herein. It should also be appreciated that the systems disclosed herein can utilize any combination of the platforms (e.g., stationary fixtures such as a pole, human user(s), truck(s) or other vehicle, aerial platform(s), floating platform(s), robotic platform(s), etc.) to support the systems 1000.

The systems 1000 shown in FIG. 4B can comprise a mobile DAISI system, similar to that illustrated in FIG. 4A. In other embodiments, the systems 1000 can comprise a larger DAISI system configured for use on a relatively long-term basis. For example, the stationary imaging system 1000A shown in FIG. 4B can be installed on a pole 1309 or other suitable structure for monitoring a storage tank 1301. A solar panel 1300 can be provided at or near the system 1000 to help provide power to the system 1000. An antenna 1303 can electrically couple to the system and can provide wireless communication between the system 1000 and any other external entity, such as a central server, for storing and/or processing the data captured by the system 1000.

A DAISI system such as system 1000 may, if desired, be coupled to a unit that adjusts the pan, tilt, rotation, height, or other position of the system 1000. As an example, system 1000 may be mounted to a pan and tilt unit. The pan and tilt unit may be able to rotate the front of system 1000 left and right (e.g., yaw system 1000 left and right) and able to rotate the front of system 1000 up and down (e.g., pitch system 1000 up and down), thereby enabling system 1000 to focus on a particular portion of the surrounding environment and, when desired, to scan different areas of the surrounding environment (i.e., to move through a desired scan path). The pan and tilt unit (or any other unit that adjusts the position of system 1000 may include motors, actuators, or other suitable mechanisms to drive movements of system 1000. The operation of a pan and tilt unit (or any other unit that adjusts the position of system 1000) may be controlled by system 1000, by the pan and tilt unit, by a remote system, by a control system capable of controlling one or more systems 1000 and/or corresponding pan and tilt units, or by any suitable and desired control system.

The stationary infrared imaging system 1000A can be programmed to continuously or periodically monitor the site. If a gas cloud 1302 escapes from the storage tank 1301, such as by leaking from a broken valve, then the system 1000A can capture a multispectral, snapshot image or series of images (e.g., a video stream) of the gas cloud 1302. As with the embodiment of FIG. 4A, the imaging system 1000A can include imaging, processing, and communications components on board the system 1000A to identify and characterize the types of gases in the cloud 1302 and to transmit the processed data to the central server, e.g., by way of the antenna 1303.

The imaging systems 1000B worn or carried by the multiple users 1275 can advantageously capture and process multispectral image data of the portions of the installation site that each user 1275 visits. It should be appreciated that the different users 1275 may work in or travel through different portions of the installation site (and also to a number of installation sites) over a period of time. When activated, the imaging systems 1000B worn or carried by the users 1275 can continuously or periodically capture multispectral image data of the different locations at the installation site(s) to which the user 1275 travels. As explained herein, the system 1000B can transmit the image data and the location at which the image was captured to the central server. If the system 1000B or the central server detects a problem (such as a gas leak), then the central server can associate that leak with a particular location and time.

Furthermore, because the central server can receive image data and location data from multiple users at different locations and viewing from different perspectives, the central server can create an organization-wide mapping of gas leaks that include, e.g., the locations of gas leaks in any of multiple installation sites, the type and concentrations and expanse or extent of each gas leaked, the particular user 1275 that captured the image data, and the time at which the image was taken. Thus, each user 1275 that carries or wears a portable imaging system 1000B can contribute information to the central server that, when aggregated by the central server, provides rich details on the status of any gas leaks at any installation sites across the organization.

The truck-mounted imaging system 1000C can be mounted to a truck or other type of vehicle (such as a car, van, all-terrain vehicle, etc.). As shown in FIG. 4B, the imaging system 1000C can be connected to an end of an extendable pole or extension member mounted to the truck 1500. The system 1000C can be raised and lowered by a control system to enable the system 1000C to image a wide area of the installation site. In some embodiments, actuators can be provided to change the angular orientation of the system 1000C, e.g., its pitch and yaw. A vibration isolation or reduction mechanism can also be provided to reduce vibrations, which may disturb the imaging process. The system 1000C can be battery powered and/or can be powered by the truck; in some embodiments, a generator can be used to supply power to the system 1000C. A user can drive the truck 1500 throughout the installation site to image various portions of the site to detect leaks. In addition, the user can drive the truck 1500 to other installation sites to detect gas leaks. As explained herein, the location of the truck 1500 can be communicated to the central server and the location of the truck 1500 can be associated with each captured image. The truck 1500 may include GPS electronics to assist in tracking the location of the truck 1500 and/or system 1000C over time as the user drives from place to place. Similarly, the aerial platform 1501 (such as an unmanned aerial vehicle, or UAV) can support the imaging system 1000D. The aerial platform 1501 can be piloted (either remotely or non-remotely) to numerous installation sites to capture multispectral image data to detect gas clouds.

Thus, the systems 1000A-1000D can provide extensive data regarding the existence of leaks at numerous installations across an organization. Monitoring numerous cameras simultaneously or concurrently across an organization, site, region, or the entire country can be enabled at least in part by providing wireless (or wired) communication between the systems 1000A-1000D and one or more central servers. Advantageously, the collection of image data from multiple sources and multiple platforms can enable the organization to create a real-time mapping of potential gas leaks, the types and amounts of gases being leaks, the locations of the leaks, and the time the image data of the leak was captured. In some arrangements, the aggregation of data about a site can improve the safety of installation sites. For example, if a gas leak is detected at a particular installation, the embodiments disclosed herein can alert the appropriate personnel, who can begin safety and/or evacuation procedures. Moreover, the aggregation of data across an organization (such as an oil service company) can provide site-wide, region-wide, and/or company-wide metrics for performance. For example, a given facility can monitor its total emissions over time and use the resulting data to help determine the facility's overall performance. A given region (such as a metropolitan area, a state, etc.) can monitor trends in emissions over time, providing a value on which to base decisions. Likewise, a company can look at the emissions performance at all of its facilities and can make decisions about whether some facilities should make new investments to improve performance, and/or whether the entire company should make various improvements. The mobile systems 1000 disclosed herein can thus provide a ubiquitous monitoring system for decision making. In addition, the systems 1000 disclosed herein can be used in a feedback control process to improve various manufacturing procedures based on the gases detected by the system(s) 1000. Accordingly, a control module may be provided to adjust the manufacturing procedure and/or parameters according to the gases measured by the system 1000.

The embodiments of the mobile infrared imaging system 1000 disclosed herein provide various advantages over other systems. As explained above, aggregation of data about a site and its potential gas leaks can provide an organization- or system-wide mapping of potential problems. Furthermore, automatic detection of gas leaks (and identification of the gases in the gas cloud) can simplify operation of the system 1000 and can reduce the risk of user errors in attempting to detect or identify gas clouds manually. Moreover, the small size of the systems 1000 disclosed herein are more easily carried or worn by the user than other systems. In addition, the systems 1000 disclosed herein can overlay the identified gas clouds on a visible image of the scene and can color code the gas cloud according to, e.g., type of gas, concentration, etc.

Figure 5:
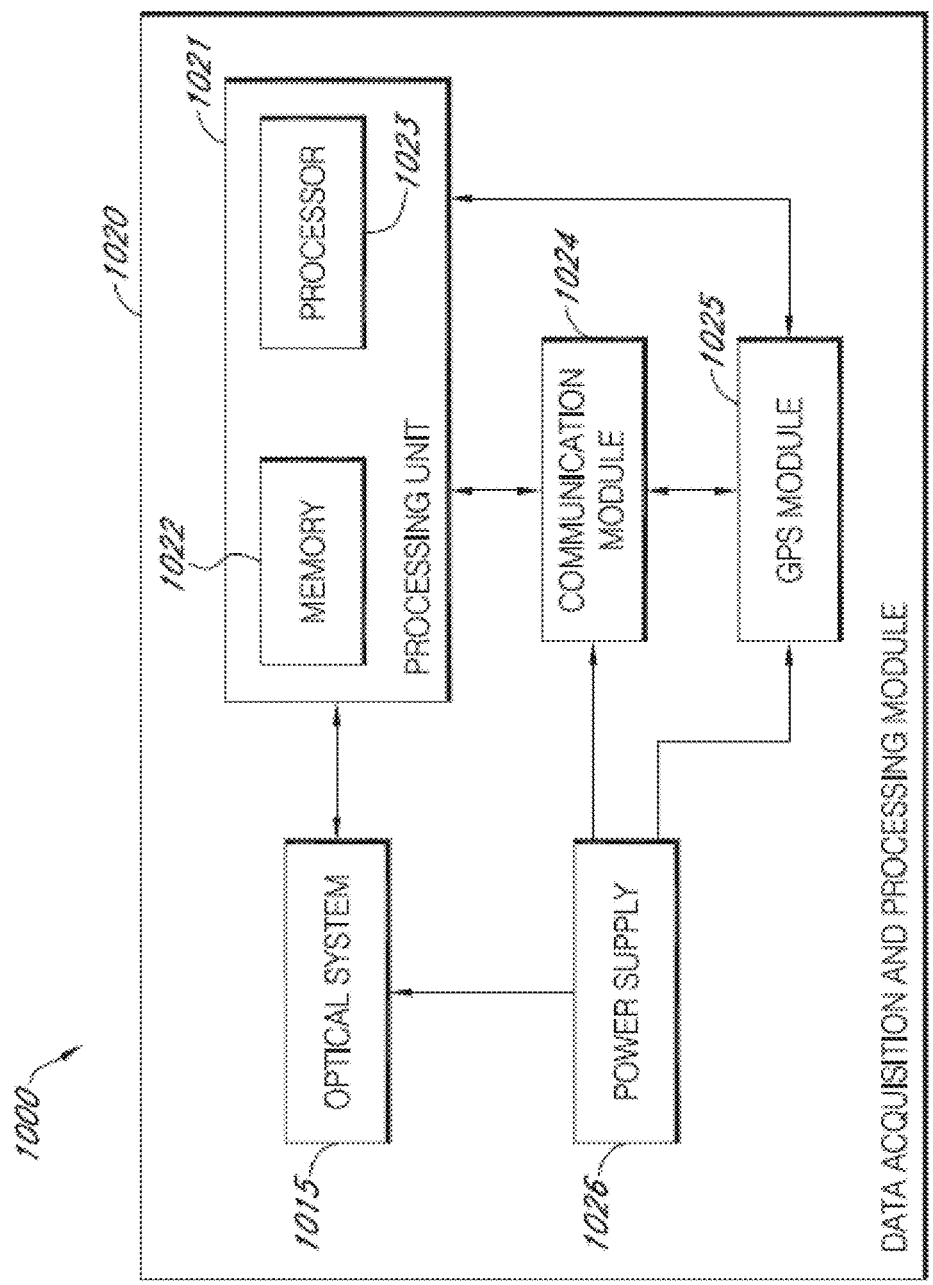
FIG. 5 is a schematic system block diagram showing a mobile infrared imaging system, according to one embodiment.

FIG. 5 is a schematic system block diagram showing a mobile infrared imaging system 1000 (e.g., a mobile DAISI system), according to one embodiment. The imaging system 1000 can include a data acquisition and processing module 1020 configured to be worn or carried by a person. The data acquisition and processing module 1020 can include, contain, or house an optical system 1015, a processing unit 1021, a power supply 1026, a communication module 1025, and GPS module 1025. In other embodiments, the data acquisition and processing module 1020 can be configured to be mounted to a structure at the site to be monitored, such as a post. The power unit 1026 can be provided on board the system 1000. The power unit 1026 can be configured to provide power to the various system components, such as the optical system 1015, the processing unit 1021, the communication module 1024, and/or the GPS module 1025. In some embodiments, the power unit 1026 can comprise one or more batteries (which may be rechargeable) to power the system components. In some embodiments, the power unit 1026 can include a solar power system including one or more solar panels for powering the system by sunlight. In some embodiments, the power unit 1026 can include various power electronics circuits for converting AC power supplied by standard power transmission lines to DC power for powering the system components. Other types of power supply may be suitable for the power unit 1026.

The system 1000 can include an optical system 1015 configured to capture multispectral image data in a single snapshot, as explained herein. For example, the optical system 1015 can include an optical focal plane array (FPA) unit and components that define at least two optical channels that are spatially and spectrally different from one another. The two optical channels can be positioned to transfer IR radiation incident on the optical system towards the optical FPA. The multiple channels can be used to multiplex different spectral images of the same scene and to image the different spectral images on the FPA unit.

The processing unit 1021 can also be provided on board the data acquisition and processing module 1020. The processing unit 1021 can include a processor 1023 and a memory 1022. The processor 1023 can be in operable cooperation with the memory 1022, which can contain a computer-readable code that, when loaded onto the processor 1023, enables the processor 1023 to acquire multispectral optical data representing a target species of gas or chemical from IR radiation received at the optical FPA unit of the optical system 1015. The memory 1022 can be any suitable type of memory (such as a non-transitory computer-readable medium) that stores data captured by the optical system 1015 and/or processed by the processing unit 1021. The memory 1022 can also store the software that is executed on the processor 1023. The processor 1023 can be configured to execute software instructions that process the multispectral image data captured by the optical system 1015. For example, the processor 1023 can analyze the different images detected by the FPA and can compare the captured data with known signatures of various types of gases or chemicals. Based on the analysis of the captured image data, the processor can be programmed to determine the types and concentrations of gases in a gas cloud. Further, as explained herein, the processor 1023 can analyze calibration data provided by the optical system 1015 to improve the accuracy of the measurements.

Advantageously, the processor 1023 can comprise one or more field-programmable gate arrays (FPGA) configured to execute methods used in the analysis of the images captured by the optical system 1015. For example, the FPGA can include logic gates and read access memory (RAM) blocks that are designed to quickly implement the computations used to detect the types of gases in a gas cloud. The small size/weight, and high performance characteristics of the FPGA can enable on board computation and analysis within the data acquisition and detection unit 1020 worn or carried by the user. The use of FPGA (or similar electronics) on board the system 1000 can reduce costs associated with using an off-site central server or larger computing device to conduct the image analysis computations. In addition, enabling computation with one or more FPGA devices on board the wearable system can also prevent or reduce communication bottlenecks associated with wirelessly transmitting large amounts of raw data from the system 1000 to a remote server or computer, which can be used in some embodiments.

The communication module 1024 can be configured to communicate with at least one device physically separate from the data acquisition and processing module 1020. For example, the communication module 1024 can include a wireless communication module configured to wirelessly communicate with the at least one separate device. The wireless communication module can be configured to provide wireless communication over wireless networks (e.g., WiFi internet networks, Bluetooth networks, etc.) and/or over telecommunications networks (e.g., 3G networks, 4G networks, etc.).

In some embodiments, for example, the wireless communication module can provide data communication between the data acquisition and processing module 1020 and a mobile device such as an electronic eyewear apparatus, a tablet computing device, a mobile smartphone, a laptop or notebook computer, or any other suitable mobile computing device. As explained herein, the mobile device can include a display on which the processed image data can be displayed to the user. For example, the types (and/or concentrations) of gases in a gas cloud can be illustrated on the display, e.g., by color coding or other suitable illustration scheme. The processed data can overlie a visible image of the scene in some arrangements. In some embodiments, the wireless communication module can provide data communication between the system 1000 and an external device remote from the system 1000, such as a central server. For example, the processed image data and/or the raw image data may be transmitted over a telecommunications network to the central server for storage and/or further analysis. In some embodiments, the processed or raw image data can be uploaded to the mobile device (e.g., notebook computer, smartphone, tablet computing device, etc.), which can in turn communicate the image data to the central server.

The GPS module 1025 can be configured to determine the location of the data acquisition and processing module 1020 at a particular time. The processing unit 1021 can store the location data and can associate the location data with a particular image captured by the optical system 1015 in some arrangements. The location data associated with the captured images can be transmitted by the communication module 1024 (or by an external device) to a central server in some arrangements.

The optical system 1015, the processing unit 1021, the power supply 1026, the communication module 1024, and/or the GPS module 1025 may be contained or housed in the data acquisition and processing module 1020, which can be carried or worn by the user. The components of the system 1000 (including the optical components, the processing components, and the communications components) may be packaged or assembled in the data acquisition and processing module 1020 and may occupy a volume less than about 300 cubic inches, less than about 200 cubic inches, or less than about 100 cubic inches. In various embodiments, the components of the system 1000 (including the optical components, the processing components, and the communications components) may be packaged or assembled in the data acquisition and processing module 1020 and may occupy a volume greater than about 2 cubic inches, or greater than about 16 cubic inches. A power supply, including a battery and/or solar module may also be included among the components packaged or assembled in the data acquisition and processing module 1020 and fit into the above-referenced volumetric dimensions.

The data acquisition and processing module 1020 (with the system components mounted therein or thereon, including the imaging optics, focal plane array, and on board processing electronics may) may be sized and shaped to fit within a box-shaped boundary having dimensions X×Y×Z. For example, in some embodiments, the data acquisition and processing module 1020 (including the imaging optics, focal plane array, and on board processing electronics may) can be sized and shaped to fit within a box-shaped boundary smaller than 8 inches×6 inches×6 inches. In some embodiments, the data acquisition and processing module 1020 (including the imaging optics, focal plane array, and on board processing electronics may) can be sized and shaped to fit within a box-shaped boundary smaller than 7 inches×5 inches×5 inches. In some embodiments, the data acquisition and processing module 1020 (including the imaging optics, focal plane array, and on board processing electronics may) can be sized and shaped to fit within a box-shaped boundary smaller than 6 inches×4 inches×4 inches. In some embodiments, the data acquisition and processing module 1020 (including the imaging optics, focal plane array, and on board processing electronics may) can be sized and shaped to fit within a box-shaped boundary having dimensions larger than 4 inches by 2 inches×2 inches. In some embodiments, the data acquisition and processing module 1020 (including the imaging optics, focal plane array, and on board processing electronics may) can be sized and shaped to fit within a box-shaped boundary having dimensions larger than 2 inches by 1 inches×1 inches. A power supply, including a battery and/or solar module, a communications module, or both may be included in the data acquisition and processing module 1020 and fit into the above-referenced dimensions. It should be appreciated that the dimensions disclosed herein may not correspond to the directions shown in FIG. 4A with respect to X, Y, and Z. Moreover, the system 1000 can have a mass and weight sufficiently small so as to enable the user 1275 to easily carry or wear the data acquisition and processing module 1020 at the site.

IV. Additional Examples of a Mobile DAISI System

Additional examples of mobile divided-aperture infrared spectral imaging (DAISI) systems are provided in this section. For example, the systems 1000 shown in FIGS. 6A-6C may be used with any of the embodiments disclosed above. Beneficially, the systems 1000 disclosed herein can provide various improvements that enable a multi-spectral, snapshot mode imaging system to be worn or carried by a person.

Figure 6B:
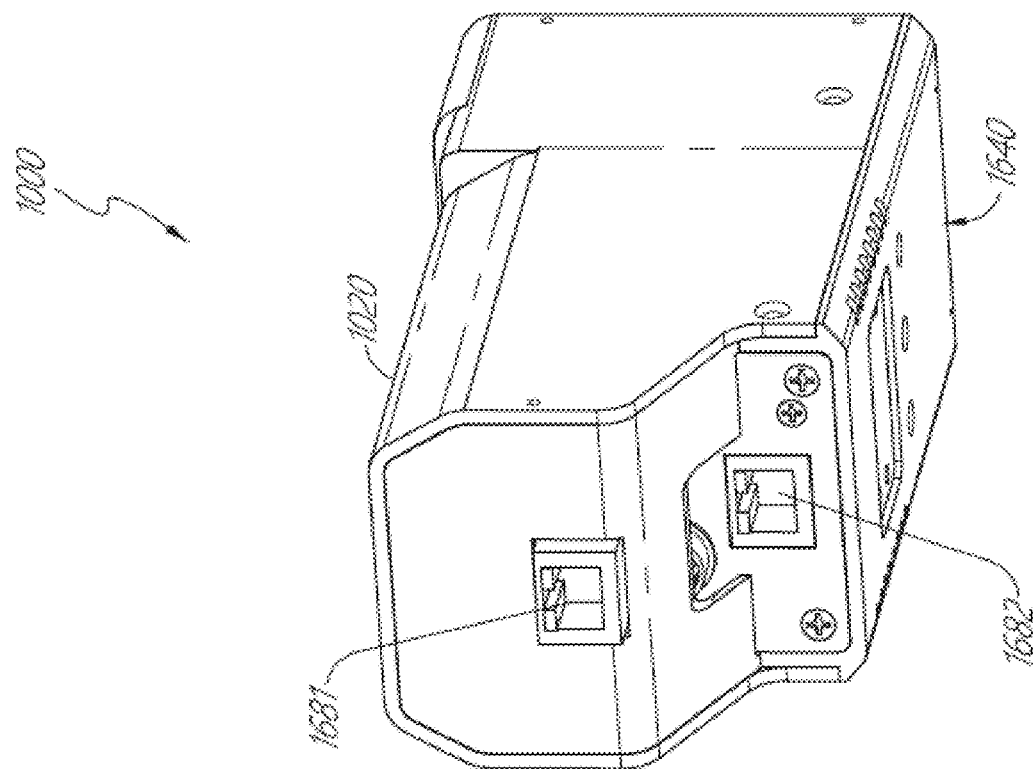
FIG. 6B is a schematic rear perspective view of the system shown in FIG. 6A.
Figure 6A:
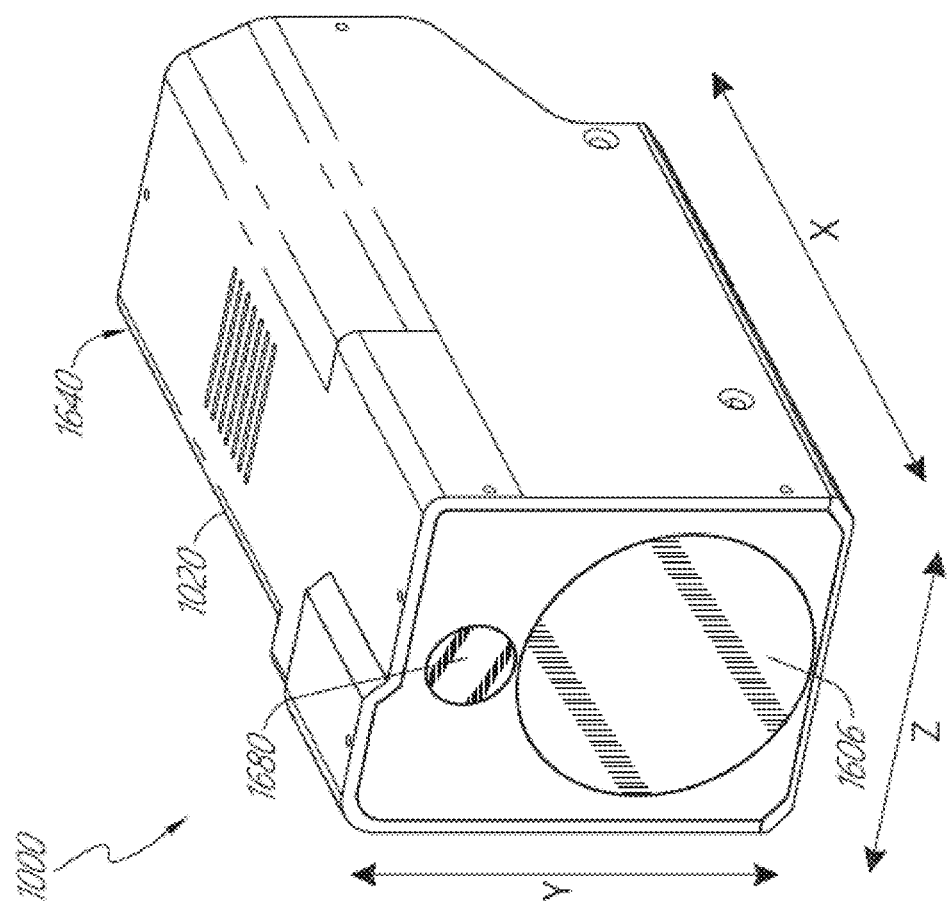
FIG. 6A is a schematic perspective view of a system, according to various embodiments.
Figure 6C:
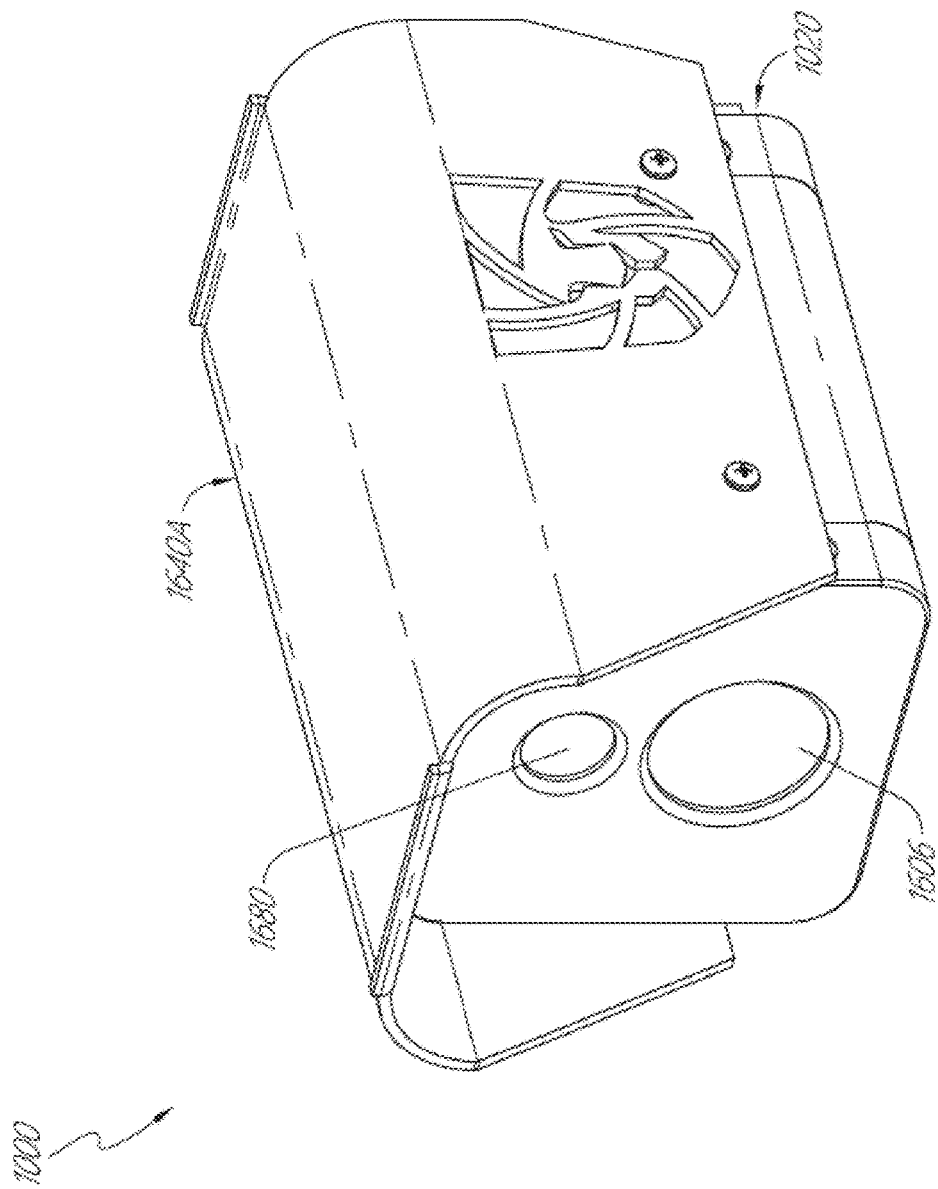
FIG. 6C is a schematic front perspective view of a system according to various embodiments.

As with the above-referenced embodiments, the systems 1000 of FIGS. 6A-6C can comprise an optical focal plane array (FPA) and components that define at least two optical channels that are spatially and spectrally different from one another. The at least two optical channels can be positioned to transfer infrared (IR) radiation towards the FPA. A processing unit comprising a processor and/or processing electronics can acquire multispectral image data representing a target species from the received IR radiation. The optical system and the processing unit can be contained together in a data acquisition and processing module configured to be worn or carried by a person. In some embodiments disclosed in this section, the imaging system may be fixed at a desired location, such as at a petroleum refinery, an oil well site, etc.

A. System Overview

FIG. 6A is a schematic perspective view of a system 1000, according to various embodiments. FIG. 6B is a schematic rear perspective view of the system 1000 shown in FIG. 6A. The system 1000 can comprise a data acquisition and processing module 1020, which may be similar to the data acquisition and processing module described above. For example, the data acquisition and processing module 1020 can comprise a housing 1640 within which the optical components of the system 1000 are housed. The system 1000 can include an optical window 1606 and a visible light imaging system 1680. The window 1606 can be configured to transmit infrared radiation from the object to the internal optical components within the housing 1640. In some embodiments, the window 1606 comprises germanium. The window 1606 and visible light imaging system 1680 may be the same as or similar to the window and visible light system described above.

As shown in FIG. 6B, the data acquisition and processing unit 1020 can comprise any suitable number of power and/or signal connections to a computing device. For example, the data acquisition and processing unit 1020 can comprise a data connector 1681 to provide data communication between the data acquisition and processing unit 1020 and a computing device. The data acquisition and processing unit 1020 can also comprise a power connector 1682 to provide electrical power to the data acquisition and processing unit 1020. In some arrangements, the data acquisition and processing unit 1020 can comprise a communication module 1024, which can provide wireless (and/or wired) data communication with an external computing device (such as a laptop computer, a tablet computer, a smartphone, etc.). In addition, the data acquisition and processing unit 1020 can comprise one or more batteries to provide power to the system 1000.

The data acquisition and processing unit 1020 can be configured to be worn or carried by a person. The combination of components described herein can advantageously enable the optical components and processing electronics to fit within a small form factor sufficient to be worn or carried by a person. For example, the data acquisition and processing unit 1020 can have dimensions and a weight (or mass) selected so as to be easily worn or carried by a human user to any suitable location, e.g., for conducting infrared imaging and monitoring of potential gas leaks at a petroleum installation. As shown in FIG. 6A, the data acquisition and processing unit 1020 can be sized and shaped to fit within a box-shaped boundary having dimensions length X×height Y×width Z. The volume of the data acquisition and processing unit 1020 can be in a range of 5 cubic inches to 40 cubic inches, in a range of 9 cubic inches to 30 cubic inches, in a range of 10 cubic inches to 30 cubic inches, in a range of 10 cubic inches to 25 cubic inches, in a range of 10 cubic inches to 20 cubic inches, or in a range of 10 cubic inches to 15 cubic inches. In some embodiments, the volume of the data acquisition and processing unit 1020 can be in a range of 15 cubic inches to 25 cubic inches, in a range of 17 cubic inches to 24 cubic inches, or in a range of 19 cubic inches to 23 cubic inches.

The length X can be in a range of 3 inches to 8 inches, in a range of 3.5 inches to 6 inches, in a range of 4 inches to 6 inches, or in a range of 5 inches to 6 inches. The height Y can be in a range of 1 inch to 5 inches, in a range of 1 inch to 3 inches, in a range of 1.5 inches to 2.5 inches, or in a range of 2 inches to 2.5 inches. The width Z can be in a range of 1 inch to 5 inches, in a range of 1 inch to 3 inches, in a range of 1 inch to 2.5 inches, or in a range of 1 inch to 2 inches. For example, the width Z can be in a range of 1.25 inches to 2 inches, in a range of 1.5 inches to 2 inches, or in a range of 1.6 inches to 1.9 inches.

The weight of the data acquisition and processing unit 1020 can be in a range of 0.5 pounds to 5 pounds, in a range of 0.5 pounds to 3 pounds, in a range of 0.75 pounds to 2.5 pounds, in a range of 1 pound to 2.5 pounds, in a range of 1 pound to 2 pounds, or in a range of 1.25 pounds to 1.75 pounds.

FIG. 6C is a schematic front perspective view of a system 1000 according to various embodiments. The components of the system 1000 of FIG. 6C may be the same as the components of FIGS. 6A-6B. However, in the embodiment of FIG. 6C can comprise a housing 1640A that is configured for use in conjunction with locations classified in Class 1, Division 1 of the National Electrical Code (NEC), available at necconnect.org. For example, the housing 1640A of FIG. 6C can be sufficiently sealed so as to prevent gases from entering the housing 1640A. As another example, the housing 1640a of FIG. 6C can be of a type generally considered to be explosion proof. The processing electronics and other components within the data acquisition and processing unit 1020 can be passively cooled without requiring external airflow into the data acquisition and processing unit 1020 from the outside environs (e.g., ambient air). In some embodiments, the data acquisition and processing unit 1020 can be filled with a gas to cool the internal components. For example, in some embodiments, data acquisition and processing unit 1020 and the housing 1640A can be filled with nitrogen gas. The system 1000 shown in FIG. 6C can be fixed in a permanent location (e.g., an oil well site or other petroleum installation) or can be configured for mobile user (e.g., worn or carried by a user).

Figure 7:
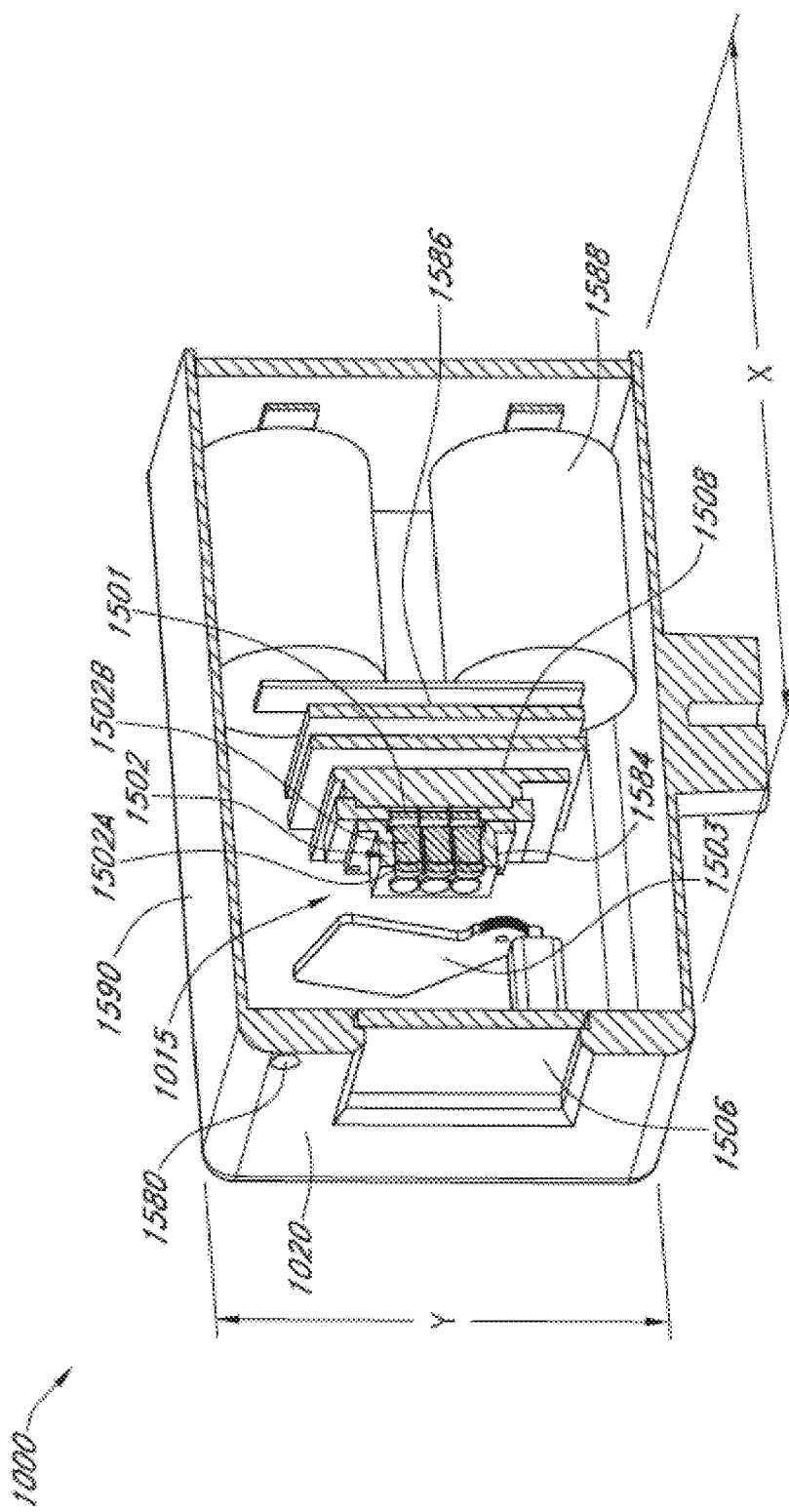
FIG. 7 is a perspective cross-sectional view of an example mobile infrared imaging system.

FIG. 7 is a perspective cross-sectional view of a mobile infrared imaging system 1000. The mobile infrared imaging system 1000 can include one or more movable shutters 1503 (e.g., two shutters) rear of the window 1506 and a lens assembly 1502 rear of the shutter(s) 1503. A filter array 1501 can be disposed rear (or forward) of the second lens array 1502B, and an optical focal plane array (FPA) unit 1508 can be disposed rear of the filter array 1501. The filter array 1501 may be disposed forward of the lens assembly 1502 (i.e., on the side of the lens assembly 1502 closest to window 1506). The optical FPA unit 1508 can be mechanically and electrically coupled with one or more substrates 1586, which may comprise printed circuit board or PCB substrates. In various embodiments, the FPA unit 1508 comprises a single FPA or detector array. Additionally, as explained herein, the lens assembly 1502, filter array 1501, and optical FPA unit can at least partially define one or more optical channels that are spatially and spectrally different. A number of the optical channels can be at least 4, at least 5, at least 8, at least 9, at least 12, at least 13, or at least 20. In some embodiments, a number of the optical channels is between 4 and 50.

One or more batteries 1588 can supply power to the system 1000 by way of the substrate(s) 1586. In addition, a visible light imaging sensor 1580 can be disposed in the housing 1590 and can be configured to provide a visible light image of the scene being captured by the system 1000. The processed IR image data can be overlaid upon the visible light image. In various embodiments the visible light imaging sensor 1580 can be used for reduction of scene-motion-induced detection errors, for example, to detect a moving object that enters the field of view (such as an animal or person) and would interfere with the data being collected.

As explained herein, the movable shutter(s) 1503 can be configured to provide spectral-radiometric calibration for the system 1000. The shutter(s) 1503 can be configured to move in and out of the field of view of the lens assembly 1502 periodically, e.g., in a time period in a range of about 1 minute to about 15 minutes, or more particularly, in a range of about 3 minutes to about 7 minutes, e.g., about 5 minutes. Although one shutter 1503 is illustrated in FIG. 7, it should be appreciated that two or more shutters may be provided. The shutter(s) 1503 can be used in static calibration procedures to provide the system with absolute temperature values. In some embodiments, only static calibration is performed, e.g., no dynamic calibration is performed. In some embodiments, both static and dynamic calibration procedures are performed.

The lens assembly 1502 can include a first lens array 1502A and a second lens array 1502B. In some embodiments, the lens assembly 1502 can comprise an array of two-part lenses denoted by the first and second arrays 1502A, 1502B. In some embodiments, the lens assembly 1502 can comprise an array of two separate lenses denoted by the first and second arrays 1502A, 1502B. Each of the lens arrays 1502A, 1502B can comprise a 4×3 array of lenses, each of which may correspond to a particular detector region in the FPA unit 1508 and can define an optical channel of the system 1000. The lenses used in the first lens array 1502A may be different from the lenses used in the second lens array 1502B. The lenses can be any suitable type of lens, including, e.g., spherical lenses, aspheric lenses, rod lenses, etc. or any combination thereof. For example, the lenses used in the first lens array 1502A can comprise aspheric lenses, and the lenses used in the second lens array 1502B can comprise rod lenses. Although the lens assembly 1502 shown in FIG. 7 includes two lens arrays, it should be appreciated that additional lens arrays may be used, e.g., three lens arrays, four lens arrays, five lens arrays, etc. In addition, to assist in enabling a small system size, the diameter of each lens in the assembly 1502 can be less than about 0.5", e.g., in a range of about 0.1" to about 0.5". The f-number of each lens can be less than about 2, e.g., in a range of about 0.2 to 2, or more particularly, in a range of about 0.5 to 2, or 1.0 to 2 or 1.1 to 2.

The first lens array 1502A and the second lens array 1502B can be coupled to one another by way of a mounting plate 1584 sized and shaped to support or receive each lens array 1502A, 1502B. For example, the first lens array 1502A can be mounted on one side of the mounting plate 1584, and the second lens array 1502B can be mounted on an opposite side of the mounting plate 1584. The mounting plate 1584 can be machined to have diameter tolerances of about +/−25 microns. The lenses of the arrays 1502A, 1502B can be secured to the mounting plate 1584 with a curable epoxy. For example, the lenses may fit into opposite sides of holes formed in the mounting plate 1584.

The optical FPA unit 1508 can comprise any suitable type of detector array that is configured to detect infrared radiation, for example, greater than 1 micron, or greater than 2 microns, or greater than 3 microns or greater than 5 microns, or greater than 6 microns and possibly lower than 20 microns, or 15 microns, or 13 microns, or 12 microns or 10 microns, in wavelength, and may be cooled or uncooled. In some embodiments the optical FPA unit 1508 comprises one or more microbolometer arrays, which may be uncooled. For example, an array of about 1000×1000 microbolometer arrays may be used in the embodiments disclosed herein. Microbolometer arrays such as those manufactured by DRS Technologies of Arlington, Va., and Sofradir EC, Inc., of Fairfield, N.J., may be suitable for the embodiments disclosed herein. For example, the DRS U8000 FPA manufactured by DRS Technologies may be used in some embodiments. In some arrangements, the microbolometer array may have a resolution of 1024×768 with a pixel pitch of 12 microns. The array of lenses can form separate channels having image detection regions that form part of the array. For example, 12 channels can be included in the 1024×768 pixel array on the detector array (microbolometer array) that are for example 250×250 pixels for each of the 12 channels. Detector arrays having more or less pixels may be employed. Similarly the number of channels be larger or smaller than 12 and the detection area on the detector array for a single channel may be larger or smaller than 250×250 pixels. For example, the detection region may comprise from between 100-200 pixels×100-200 pixels per detection region. For example, the detection region may comprise from between 100-200 pixels×100-200 pixels per detection region, from between 200-300 pixels×200-300 pixels per detection region, or from between 300-400 pixels×300-400 pixels or from between 400-500 pixels×400-500 pixels. Likewise the detection region for a channel may measure 100-200 pixels on a side, 200-300 pixels on a side, 300-400 pixels on a side, 400-500 pixels on side or larger or smaller.

In some arrangements, the spectral band of the microbolometer can be about 7.5 microns to 14 microns or can be about 3 microns to 14 microns or 3 to 8 microns. The microbolometer array can operate at a frame rate of about 30 Hz and can operate at operating temperatures of about −40° C. to +70° C. In various embodiments, the microbolometer array is an uncooled microbolometer that does not include a cooler. The sensitivity of the microbolometer at F/1 can be <about 40 mK. The systems 1000 disclosed herein can be used to detect wavelengths in a range of about 1 micron to about 20 microns. For example, the systems 1000 disclosed herein can be used to detect wavelengths above about 6 microns, e.g., in a range of about 6 microns to about 18 microns, in a range of about 3 microns to about 14 microns, or more particularly, in a range of about 7 microns to about 14 microns or 3 to 8 microns. In various embodiments, the individual detector elements of the microbolometer array can be spaced relatively close together to at least partially enable a small, compact system. For example, adjacent detector elements of the array can be spaced apart by a distance in a range of about 7 microns to about 15 microns, or more particularly in a range of about 9 microns to about 13 microns, e.g., about 11 microns. The individual lenses can be spaced apart by a distance in a range of about 20 mm to about 35 mm, e.g. in a range of about 24 mm to about 30 mm, e.g., about 27.5 mm. Likewise the spatially and spectrally spaced channels may be physically spaced apart by 20 to 35 mm, 24 mm to 30 mm, etc. Although various embodiments of the system are described as including an FPA comprising for example a microbolometer array, certain embodiments comprise a plurality of FPAs. In some embodiments, a single optical FPA is used. In some embodiments, detectors of the optical FPA are configured to detect radiation in the same band of IR wavelengths.

The on-board processing electronics of the data acquisition and processing module 1020 can process the IR optical data to detect and/or identify a target species from the IR radiation received at the optical FPA. For example, the module 1020 can be configured to acquire multispectral image data and analyze the acquired image data to identify the target species. For example, the mobile imaging systems 1000 disclosed herein can be configured to image a 10 m×10 m object area at a distance of about 17 m at a resolution of about 0.04 m. In this example, any gas leaks that generate a gas cloud of at least about 1.5 inches in size can be detected and/or identified by the system 1000. The detection and identification methods can be performed substantially in real-time such that the user can be alerted if any leaks are identified.

As explained above, the infrared image data captured by the system 1000 can be processed on board the data acquisition and processing module 1020 of the imaging system 1000. One way to provide a smaller system 1000 is to process the image data using one or more field-programmable gate arrays (FPGA) configured to execute methods used in the analysis of the images captured by the optical system 1015. In some embodiments, one or more Application Specific Integrated Circuits (ASICs) may be used instead of, or in addition to, the FPGAs. For example, an ASICs chip may include a FPGA. The FPGA(s) (and/or ASIC(s)) can be mounted to and electrically coupled with the substrate(s) 1586 shown in FIG. 7 and can be physically located proximate the optical system. For example, the FPGA can include logic gates and read access memory (RAM) blocks that are designed to quickly implement the computations used to detect the types of gases in a gas cloud. The small size/weight, and high performance characteristics of the FPGA can enable on board computation and analysis within the data acquisition and detection unit 1020 worn or carried by the user. The use of FPGA (or similar electronics) on board the system 1000 can reduce costs associated with using an off-site central server or larger computing device to conduct the image analysis computations. Advantageously, the embodiments disclosed herein can enable on-board computation even though it can be challenging to implement complex methods on the limited computing platform that FPGAs provide.

In addition, enabling computation with one or more FPGA devices on board the wearable system can also prevent or reduce communication bottlenecks associated with wirelessly transmitting large amounts of raw data from the system 1000 to a remote server or computer. For example, the infrared optical system 1015 disclosed herein may generate up to about 380 Mbps of raw image data at 30 frames per second, and the visible sensor 1580 may generate about 425 Mbps of raw image data at 30 frames per second. The resulting data rate of about 800 Mbps is faster than most conventional wireless technologies. While data compression and/or pre-processing may reduce the raw data rates for the visible and IR images, in some embodiments, the IR image data may only be compressed by a ratio of about 2:1. The resulting overall data rate of about 192 Mbps may not be transmitted effectively by conventional wireless communications devices. Accordingly, performing the image processing calculations on board the system 1000 (e.g., on the data acquisition and processing module 1020) can reduce the occurrence of or avoid bottlenecks generated by wirelessly communicating the raw image data to an off-site central server.

One challenge to implementing a mobile imaging system is the power requirements of each component of the system, including, e.g., the IR optical system 1015, the visible sensor 1580, the processing electronics, the wireless communications modules, etc. Advantageously, the mobile infrared imaging systems 1000 disclosed herein can be configured to operate by battery power for long periods of time without recharging or replacing the batteries 1588. In some arrangements the one or more batteries 1588 can comprise lithium ion batteries, which have relatively high energy densities. In addition, to help reduce power consumption within the system 1000, the FPGAs of the data acquisition and processing module 1020 can be advantageously programmed such that power consumption is lower than that used for other types of processing electronics.

The systems 1000 disclosed herein can advantageously operate for between 8 hours and 36 hours without recharging or replacing the batteries, or more particularly between about 10 hours and 24 hours without recharging or replacing the batteries. In some embodiments, the system 1000 can operate for at least about 12 hours without recharging or replacing the batteries. The components of the data acquisition and processing module 1020 (including the imaging optics, focal plane array, and on board processing electronics may) can be configured to operate at relatively low electrical power levels, e.g., at power levels in a range of about 3 W to about 10 W, or more particularly in a range of about 4 W to about 7 W, or in a range of about 4 W to about 6 W, e.g., about 5 W in some embodiments. The components of the data acquisition and processing module 1020 (including the imaging optics, focal plane array, and on board processing electronics may) can also be configured to operate at relatively low overall energy levels for a single charge of the batteries 1588, e.g., at energy levels in a range of about 60 Watt-hours (Wh) to about 100 Wh, or more particularly in a range of about 80 Wh to about 95 Wh, or in a range of about 85 Wh to about 90 Wh.

In addition, for each of the embodiments disclosed herein, various motion detection and/or compensation techniques can be implemented to account for relatively large-scale motions that are induced by the user moving his or her head during use. For example, when a user is visiting a well site or other installation, the user may be continuously walking and looking in different directions (e.g., by rotating his or her head). Additionally, vibration can be introduced by the user's natural unsteadiness. Such movement can continuously change the system's field of view at a relatively rapid rate, which can affect the accuracy of the methods used to determine the identity of species in a gas cloud or other object. Accordingly, it can be desirable to provide improved motion detection and/or compensation techniques to reduce errors associated with the movements of the user.

V. Examples of Window Obscuration Sensors

The DAISI systems disclosed herein may include one or more window obscuration sensors that help reduce false detection of target species. In particular, if there is water, dirt, grime, dust, bugs or other foreign contaminants on the DAISI system's optical window (e.g., optical window 1606 of FIG. 6A or window 1506 of FIG. 7), the contaminants can induce a perceived spectral change into the system and create the false signature of a target species (e.g., a hydrocarbon gas like methane) due to parallax. In other words, objects in the near field may block one IR channel disproportionately to the other channels, causing a shift in the IR spectrum received by the optical detector system that could be perceived by the system as a target species in the scene or preventing proper sensing of target species (e.g., near field objects may result in false positives or false negatives). The system may therefore falsely report detection of a target species due to the presence of water, dirt, bugs, or other such contaminants on the optical window.

The system may also be susceptible to false positives when objects are sufficiently near the optical window (i.e., when there are objects in a near-field region). The distances at which the system is susceptible to false positives may depend at least in part on the optical properties of the imaging system and its lenses. For objects at larger distances (i.e., objects in a far-field region), the system may be able to accurately identify whether or not those objects at further distances are one of the target species. The near-field region in which the imaging system may be susceptible to false positives may include distances of less than 2 meters, less than 1 meter, less than 50 centimeters, etc.

Beneficially, the systems 1000 disclosed herein can provide one or more window obscuration sensors that can detect when the optical window is obscured (e.g., sensors that can detect objects on or in front of the window that may introduce obscuration that may degrade operation of the system) by contaminants on the window or objects are located within the near-field region and thus the system can reduce or eliminate false alarms and false detections of target species.

A. Dual-Channel Window Obscuration Sensors

Figure 8B:
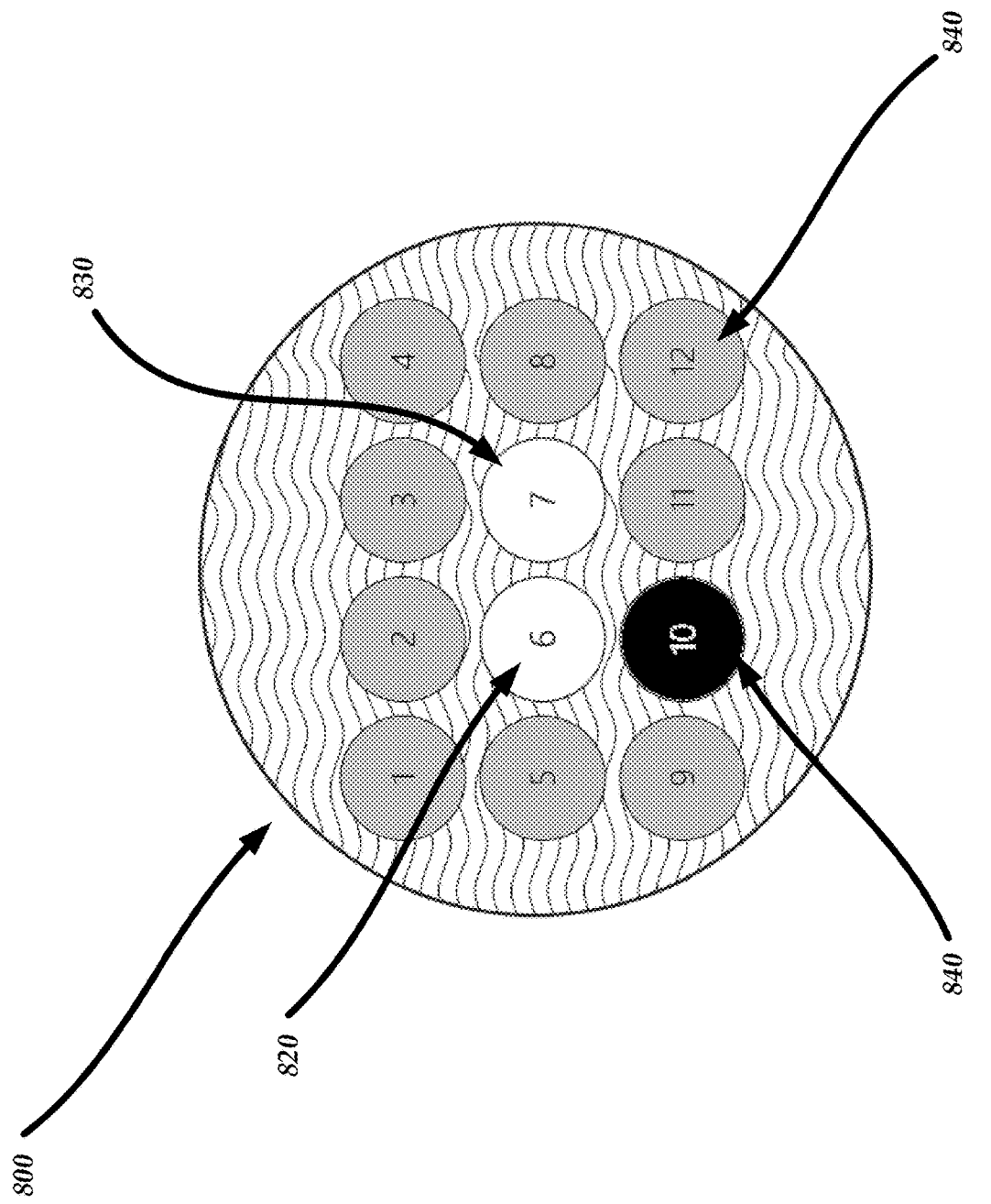
FIG. 8B is a schematic diagram of example optical filters for an imaging system having divided optical channels and having a window obscuration sensor formed from at least one of the optical channels.

As shown in FIGS. 8A and 8B, a system 1000 may include a 4×3 array of optical channels, defined in part by an array 800 of optical filters. The array 800 may include a variety of infrared filters such as infrared filters 810. Most of the optical channels may have an infrared filter such as filter 810 as shown in FIG. 8A. Moreover, each of the infrared filters may pass a different set of infrared frequencies, such that the system 1000 can image a scene in a variety of different wavelengths simultaneously as part of detecting target species. If desired, an array such as the 4×3 array of FIG. 8A may include one or more unused optical channels, such as channel 840. In such embodiments, a light blocking filter may be disposed in the unused optical channel(s) to ensure that no stray light enters adjacent channels. In at least some example, channel 840 may be a reference channel with a cover over the lenses (e.g., used for tracking temperature changes in the optical system).

The systems 1000 disclosed herein can include dual-channel window obscuration sensors (WOS), as shown in FIG. 8A. With a dual-channel WOS sensor, the systems 1000 can use differences between data from two channels such as channels 850a and 850b to exclude from detection objects that are disposed away from the systems 1000 and thereby focus upon objects that are located within the near-field of systems 1000. In other words, the systems 1000 can use parallax differences between the two channels 850a and 850b of the WOS sensor to identify objects that are within the near-field region and that might otherwise trigger a false positive identification of a target species.

The dual-channel WOS may include channels 850a and 850b associated with filters 820 and 830. Filters 820 and 830 may be any type of filter or may even be omitted from the filter array 800. As another example, filters 820 and 830 may pass a broad spectrum of incoming light, such as visible light or broad ranges of infrared light including wavelengths in which the focal plan array is sensitive. In some arrangements, filters 820 and 830 may pass infrared light in a spectral band from about 3 microns to about 14 microns, from about 7.5 microns to about 14 microns, from about 3 microns to about 8 microns, etc.

In at least some designs, dual-channel window obscuration sensors may be associated with optical channels such as channels 850a and 850b disposed in the center two channels of an array of channels, as illustrated in FIG. 8A. By disposing the WOS channels in the center two channels of an array, such as a 4×3 array, the parallax differences between the two channels can be concentrated in an x-axis, thereby simplifying detection of objects near the systems 1000. In general, however, WOS channels may be disposed in any desired location or in any channels of an array, including the center channels, peripheral channels, and corner channels.

A schematic diagram of the array 800 of optical filters is shown in FIG. 8B. As shown in FIG. 8B, the 4×3 array may include 12 optical channels. Optical channels 6 and 7 may be associated with WOS filters 820 and 830, which pass a relatively broad spectrum of wavelengths. In contrast, optical channels 1-5, 8, 9, 11, and 12 may be associated with infrared filters 840, which may pass narrow spectrums of infrared wavelengths as appropriate for the detection of target species using infrared spectral signatures, as discussed herein. Optical channel 10, associated with filter 840, may be an unused optical channel. The arrangement of optical channels in FIG. 8B is merely an example and, in general, infrared optical channels, WOS channels, and any unused optical channels may be disposed in any desired arrangement.

1. Lens Focal Lengths for Window Obscuration Sensors

In order for the WOS sensors to focus on the optical window 1506 and the near-field region just in front of the optical window 1506 (i.e., the region in which systems 1000 are susceptible to false detections), lenses for the WOS sensors should be provided with an appropriate focal length. As such, the distances between the optical window 1506, lens assembly 1502, and optical FPA unit 1508 together with the focal length of the lens assembly 1502 should be considered.

Figure 9:
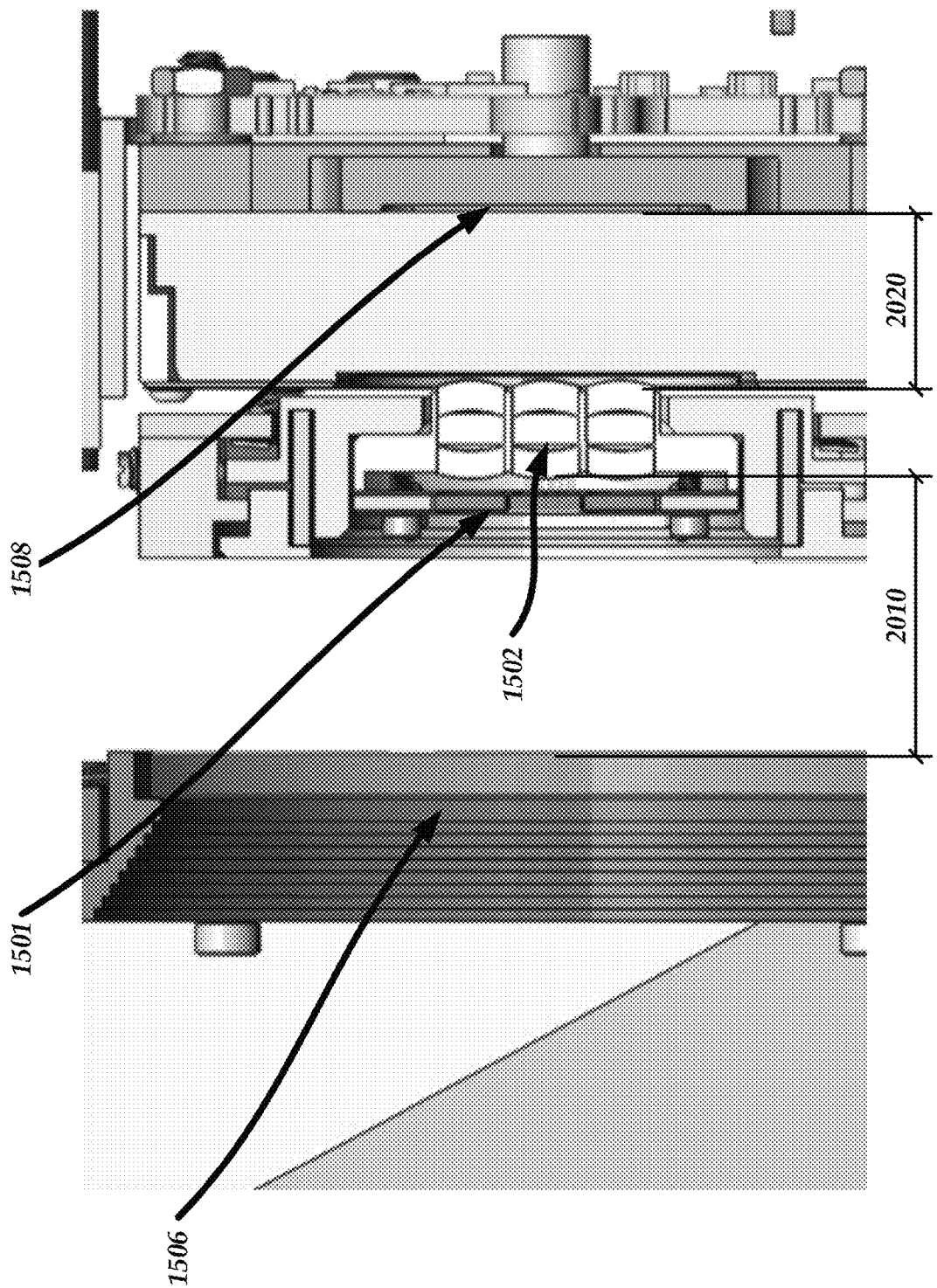
FIG. 9 is a schematic diagram of an example DAISI system illustrating distances between an optical window, an array of lenses, and a focal plane array (FPA).

FIG. 9 illustrates the distances between optical window 1506, lens assembly 1502, and optical FPA unit 1508. In particular, FIG. 9 illustrates the separation 2010 between optical window 1506 and lens assembly 1502 and illustrates the separation 2020 between lens assembly 1502 and FPA unit 1508. In at least some designs, the separation 2010 may be approximately 26 millimeters, while the separation 2020 may be approximately 2.4 millimeters.

Apply a thin lens approximately (i.e., setting aside the depth of lens assembly 1502 and assuming lens assembly 1502 included a single layer of thin lenses), the thin lens approximation can be used to determine what focal length is needed for a WOS sensor to receive light from the entire optical window 1506 (and thus be able to detect when a bug or other contaminant is on any part of the window 1506). The thin lens indicates that the focal length of a WOS channel is:

$$F=(1/x+1/y)^{-1}$$

wherein x is the distance from the lens assembly 1502 to the optical window 1506 and y is the distance from the lens assembly 1502 to the optical FPA 1508. Given a distance x (i.e., separation 2010) of approximately 26 millimeters and a distance y (i.e., separation 2020) of approximately 2.4 millimeters, the lenses in lens assembly 1502 associated with WOS sensor should preferably have a focal length of approximately 2.2 millimeters. Depending on the depth of the field of the lenses, slightly longer or shorter focal lengths may be utilized. In particular, it may be desirable to provides lenses having a depth of field that include the depth of the optical window 1508 as well distances in front of the optical window 1508 in regions in which the systems 1000 are susceptible to false detections due to objects in the near-region. In at least some designs, the systems 1000 may be susceptible to false detections when certain objects are within approximately a few tens of centimeters, less than 20 centimeters, or less than 50 centimeters of optical window 1506

In at least some designs, the lenses associated with WOS channels 850*a* and 850*b* (see FIG. 8A) may be in focus for a range of distances from the lenses that include the optical window 1506 as well as any regions in front of the optical window 1506 where the presence of an object may disrupt normal operation of the detection of target species by the systems 1000. In particular, the lenses of channels 850*a* and 850*b* may be focused on the optical window, may be focused at a location between the optical window and the lenses, or may be focused at a location beyond the optical window. In arrangements in which the plane of focus (e.g., the focus depth) is not set at the optical window, the lenses may have a depth of field that extends from the plane of focus to the distance of the optical window and to distances spaced apart from the optical window (e.g., regions in front of the optical window in which the systems 1000 may be susceptible to false alarms by the presence of external objects). The depth of field of the lenses of WOS channels 850*a* and 850*b* may be selected by selecting the optical properties of the lenses including possibly any of the lenses' aperture sizes, focal distance (e.g., distance from the systems 1000 at which the lenses are focused), focal length, or combinations thereof.

As examples, the depth of field of the WOS channels 850*a* and 850*b* (e.g., the region in which objects imaged by channels 850*a* and 850*b* are generally in focus) may extend from the optical window to approximately 1 meter away from the optical window, from the optical window to approximately 50 cm away from the optical window, from the optical window to approximately 20 cm away from the optical window, from the optical window to approximately 10 cm away from the optical window. In various designs, the f-number may be between f/10 or f/8 or f/5 or f/2 or f/1 and f/1 or f/0.9 or f/0.8 or f/0.7, or any f-number in any range defined by any of these values. Also, in various designs, the lenses in the channels 850*a* and 850*b* may have a focal length less than the lenses in other channels. For example, the focal length in other channels may be 2 or 5 times larger than the focal length in WOS channels 850*a* and 850*b*.

2. Dual-Channel WOS Algorithms

Figure 10:
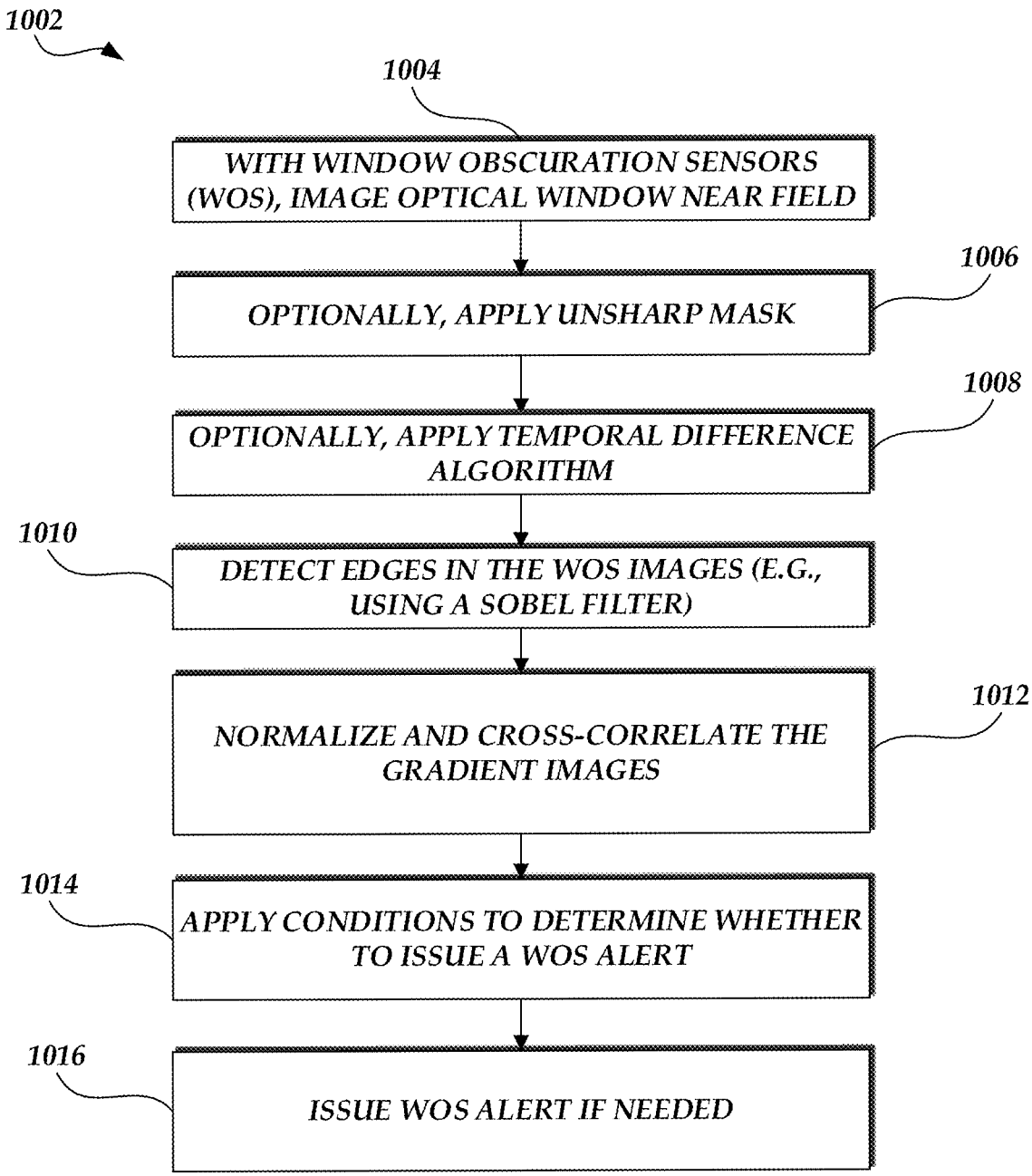
FIG. 10 is a flow chart of illustrative steps involved in one example of detecting objects on or near an optical window of the DAISI system.

In at least some designs, the systems 1000 may analyze image data from WOS channels and detect objects that may otherwise lead to false alarms using an algorithm of the type described herein. A method 1002 of analyzing WOS image data to detect whether optical window 1506 is obscured is shown in FIG. 10. While FIG. 10 illustrates a detailed method for evaluating WOS sensor data, various steps may be excluded, alternative steps may be included, and the steps may be reordered. As an example and as discussed later in connection with single-channel WOS systems, the cross-correlation step may be omitted. In general, FIG. 10 may involve example steps for evaluating focus levels images from WOS channels 850*a* and 850*b* (e.g., whether the images are in focus, whether any parts of the images are in focus, etc.). Additionally, FIG. 10 may involve comparing the images from the two WOS channels 850*a* and 850*b* with each other to determine how similar the two images are at a variety of offsets.

In step 1004, window obscuration sensors may image optical window 1506 and the area in front of optical window 1506 (i.e., the near field region in front of optical window 1506). Processing circuitry may receive and analyze those images in the manner set forth in FIG. 10. The processing circuitry may include, as examples, processing unit 1021 of FIG. 5 or external equipment.

In optional step 1006, an unsharp mask algorithm may be applied to the WOS images, to sharpen the WOS images. An unsharp mask involves using a blurred negative image to create a mask that is combined with the original image to create an image that is less blurry. An unsharp mask generally amplifies the high-frequency components of an image. Alternatives to unsharp masks include edge amplification, high-pass filters, derivative-based filtering, edge enhancement, an image sharpening mask, a contrast filter, contrast amplification, contrast enhancement, etc.

In optional step 1008, a temporal difference algorithm may be applied to the WOS images. The temporal difference algorithm may subtract out from the WOS images a reference image (or an average of multiple reference images, reference images may be prior images captured by an optical channel) or plurality of reference images from each WOS image. Each reference image may be an image frame captured by the WOS sensors at a time when it is known or presumed there are no objects on or near window 1506. In fixed installations, subtracting out a relatively fixed background, in the manner of step 1008, can facilitate detection of new objects that appear on or near optical window 1506. In general, subtracting out a reference image or images may highlight movement in the image by removing static and other slow moving objects.

In step 1010, processing circuitry may identify edges in the WOS images. As an example, a Sobel filter may be applied to the WOS images to create an image of the gradients (i.e., edges) in the WOS images. Additionally, a threshold operation may be applied to remove any gradients that are lower than a given threshold, leaving only large gradients (i.e., sharp edges). Because only objects that are in focus of the WOS sensors will have sharp edges, steps 1006-1010 have the effect of filtering out distance objects. In particular, distance objects will be out of focus in each WOS image, will therefore lack sharp edges, and will get filtered out by a Sobel filter with a threshold. Alternatives to Sobel filters include edge detection masks, edge detection algorithms, a Canny edge detector, a differential approach to edge detection, a phase stretch transform (PST), contrast enhancement, contrast measurement, etc.

In step 1012, the gradient images from step 1010 may be normalized and cross-correlated. In some cases, each gradient image may be normalized by subtracting the mean pixel value across the image from every pixel value and then by dividing each pixel by the standard deviation of pixel values. Cross-correlation may look at the similarity between the two gradient images, by combining the two gradient images with a logical AND operation. Any portions of the gradient images that both indicate edges (for a given horizontal offset) will multiply and yield a result, while portions that don't both indicate edges will include a multiplication by zero or a small value and yield no value or only a negligible value. Alternatives normalization and cross-correlation include comparing the gradient images, comparing any of the images received or generated in a prior step, comparison without normalization, comparison of the gradient or other images at a variety of offsets, comparison of the original images, etc.

As the WOS sensor includes a pair of divided channels spaced apart horizontally, the cross-correlation for a variety of horizontal pixel offsets may be of interest. As result, step 1012 may involve calculating cross-correlations for a variety of horizontal pixel offsets. Put another way, the similarity of the gradient images may be calculated when the gradient images are registered (i.e., aligned) as well as calculated for a variety of horizontal offsets in which one gradient image is horizontally offset from the other. Since objects that are close to or on the optical window will be in different positions in the two WOS images (and then the two gradient images), the cross-correlation is likely to peak not when the WOS images are aligned, but when the WOS images are offset by an amount that accounts for the parallax differences between the WOS images. Thus, it may be desirable to calculate the cross-correlation for the gradient images across a range of horizontal offsets.

Because the sensors are viewing objects on or near the optical window, the images of the objects will appear at different locations in each of the images, because the sensors are at different perspectives. Thus, step 1012 may involve comparing images from the two WOS channels 850a and 850b. The comparison may show that image features on a first image from the first WOS channel 850a are offset with respect to corresponding image features on the second image from the second WOS channel 850b. This offset may result from parallax. The two sensors for the respective first and second WOS channels 850a, 850b, view objects on or near the window from two perspectives. The different perspectives result in images of the objects (in the near-field region) appearing at different location on the two respective WOS sensors. This difference or offset in location is larger for objects closer to the sensors such as objects on the window in comparison to objects at a far distance from the window. Accordingly, by detecting the offset, whether the objects are on or near the window as opposed to being distant from the window may be determined. In some implementations, the images may be processed, e.g., compared, after introducing a variety of different offsets or shifts of the images with respect to each other. By comparing these images (and the associated image features) at a variety of different offsets, the method can figure out how much the objects in the two images are offset, and possibly determine if there are any objects within the region of interest (e.g., on or near the optical window). Additionally, the method can potentially identify the distance at which the object is located and/or account for the parallax differences.

In at least some examples, WOS channels 850a and 850b may have focal distances similar to those of the optical channels used in detection of target species. In such examples, the window obscuration sensor system may utilize parallax-induced differences in the images from the WOS channels 850a and 850b to identify whether or not objects are located within the near-field region (e.g., on or near the optical window 1506). The WOS system may also utilize parallax-induced differences even when the WOS channels 850a and 850b have significantly shorter focal distances (e.g., are focused on or near the optical window) than the optical channels used in detection of target species.

While the examples described herein generally provide WOS channels that are spaced apart horizontally and aligned vertically, this is merely one potential arrangement. In general, the WOS channels may alternatively be spaced apart vertically and aligned horizontally, or even spaced apart both vertically and horizontally (e.g., in a diagonal manner). The various examples described herein apply to such arrangements, with corresponding differences (e.g., cross-correlations would be calculated for vertical or diagonal offsets instead of just horizontal offsets).

In step 1014, various conditions may be applied to reduce false positive WOS alerts. In other words, the processing circuitry analyze various conditions to determine whether to issue a WOS alert (i.e., an alert indicating that there is water on optical window 1506, or some other contaminant on or near the optical window, which could interfere with proper detection of a target species). One such condition may be that there must be at least a predetermined number of "bad" pixels, or pixels in the gradient images that exceed the threshold discussed in connection with step 1010. In other words, the condition may involve determining that there are at least a predetermined number of sharp edges in the gradient images, such sharp edges being associated with water or other objects on or near the optical window. As an example, this condition may require there be at least 25 "bad" pixels in the gradient images. The number of "bad" pixels needed to trigger a WOS alert may be configurable by a user. In general, a higher required number of "bad" pixels will make the WOS alarm less sensitive to water or other objects on or near the optical window.

Another potential condition that may need to be satisfied to trigger a WOS alert is a cross correlation value above a predetermined threshold. In one example, the predetermined threshold is a value of at least 0.4. In other words, the two gradient images must be sufficiently alike that when logically AND'd together in their most correlated horizontal alignment, the cross correlation value is at least 0.4 The cross correlation value required to trigger a WOS alert may be user configurable. In general, a higher cross correlation value will make the WOS alarm less sensitive to water or other objects on or near the optical window.

As will be discussed in greater detail in connection with FIG. 21C, the processing circuitry may subtract a cross-correlation value (e.g., one of the lower cross-correlation values, the minimum cross-correlation value in box 21k) from the set of cross-correlation values before analyzing the peak value. By subtracting out one of the lower cross-correlation values from box 21k, the processing circuitry may be able to distinguish between the presence of target species in close proximity (for which it may not be desirable to issue a WOS alert) and the presence of other objects in close proximity (for which it may be desirable to issue a WOS alert).

A third potential condition may be that the cross correlation value of 0.4 must occur within an offset of 30 pixels. In other words, cross correlation of step 1012 may only be calculated (or may only be used in triggering a WOS alert) for offsets that are within 30 pixels (in either horizontal direction) of the original alignment of the two gradient images. Alternatively, step 1012 may involve a comparison of any of the images described in connection with FIG. 10 for any suitable number of offsets over any suitable number of offset ranges. As an example, the method may include comparing images from channels 850a and 850b by shifting the image from one channel in a range from 25 pixels leftwards to 25 pixels rightwards relative to the other channel. The offsets may generally correspond to the depth of field of the WOS channels 850a and 850b.

This may serve to limit the processing load of the WOS algorithm while still identifying relevant objects in or near the optical window. The offset limit for cross correlations that trigger a WOS alert may be user configurable.

3. Examples of WOS Sensing in Various Conditions

FIGS. 11A-21C illustrate various stages of WOS image processing and alert condition detection for a variety of conditions, showing the performance of the window obscuration sensor in correctly identifying the presence of objects on or near the optical window of the systems. As previously noted, objects that are on or near the optical window may generate false positives and appear to the DAISI systems as a target species of gas, due in part to parallax effects in the near field rage. Thus, the window obscuration sensors described herein can beneficially identify when objects are on or near the optical window, and providing a corresponding WOS alert. FIGS. 11A-21C highlight the performance of the WOS alerting system in various conditions.

The descriptions of FIGS. 11A-21C may refer to actions being taken or decisions made by a system such as a WOS system. In general, any suitable processor or electronics in systems 1000 or in external equipment may perform the described actions or make the described decisions. As examples, processing unit 1020 and processor 1023 of systems 1000 may implement the actions and decision-making processes described herein in connection with FIGS. 11A-21C.

When a WOS alert is provided by the DAISI systems, the DAISI systems may forward the alert to a user, so that the user can remove the object potentially interfering with accurate measurement or detection (e.g., clean the optical window), and may also temporarily disable detection of target species (e.g., to avoid false alerts caused by the objects detected by the WOS sensor). Alternatively, the DAISI system may continue detection of target species when the WOS channels 850a and 850b detect objects in the near-field region (e.g., within approximately 1 meter of the system or within approximately 20 centimeters or the system). In some examples, the DAISI system may use data from WOS channels 850a and 850b to compensate for the presence of objects in the near-field region that would otherwise impact detection of target species and may thereby enable continued operate and accurate detection of target species. As an example, the DAISI system may use data from WOS channels 850a and 850b to determine which IR channels are obscured and by how much those channels are obscured, and then may alter its analysis of IR image data from those channels to compensation for the obscuration (e.g., the DAISI systems may boost IR image signals from obscured channels to compensate for the obscuration).

a. A Fishing Lure at 2 Centimeters

Figure 11A:
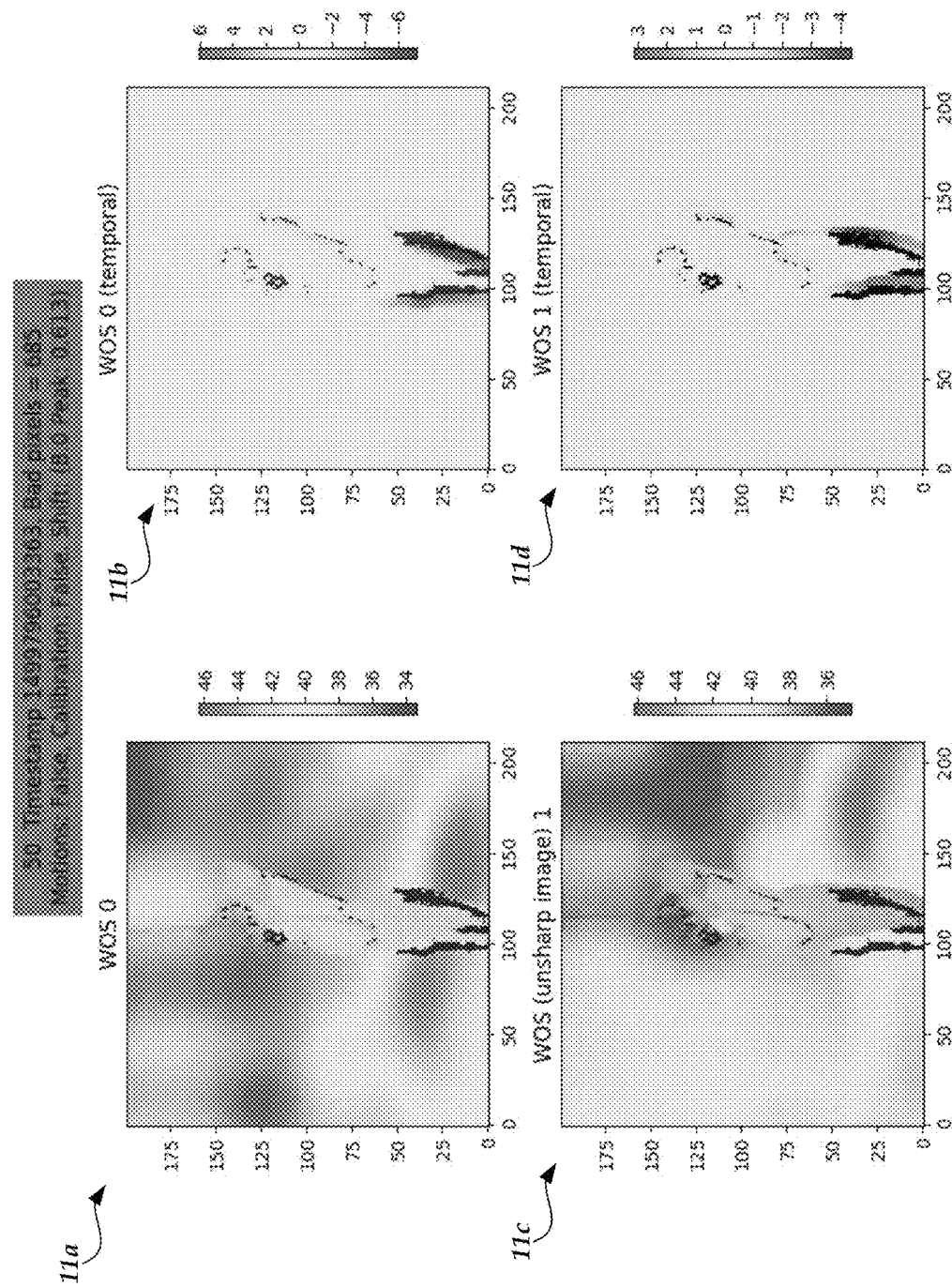
FIGS. 11A and 11B show an example of various stages of processing of data taken by window obscuration sensors with a fishing lure approximately 2 cm away from the optical window.
Figure 11B:
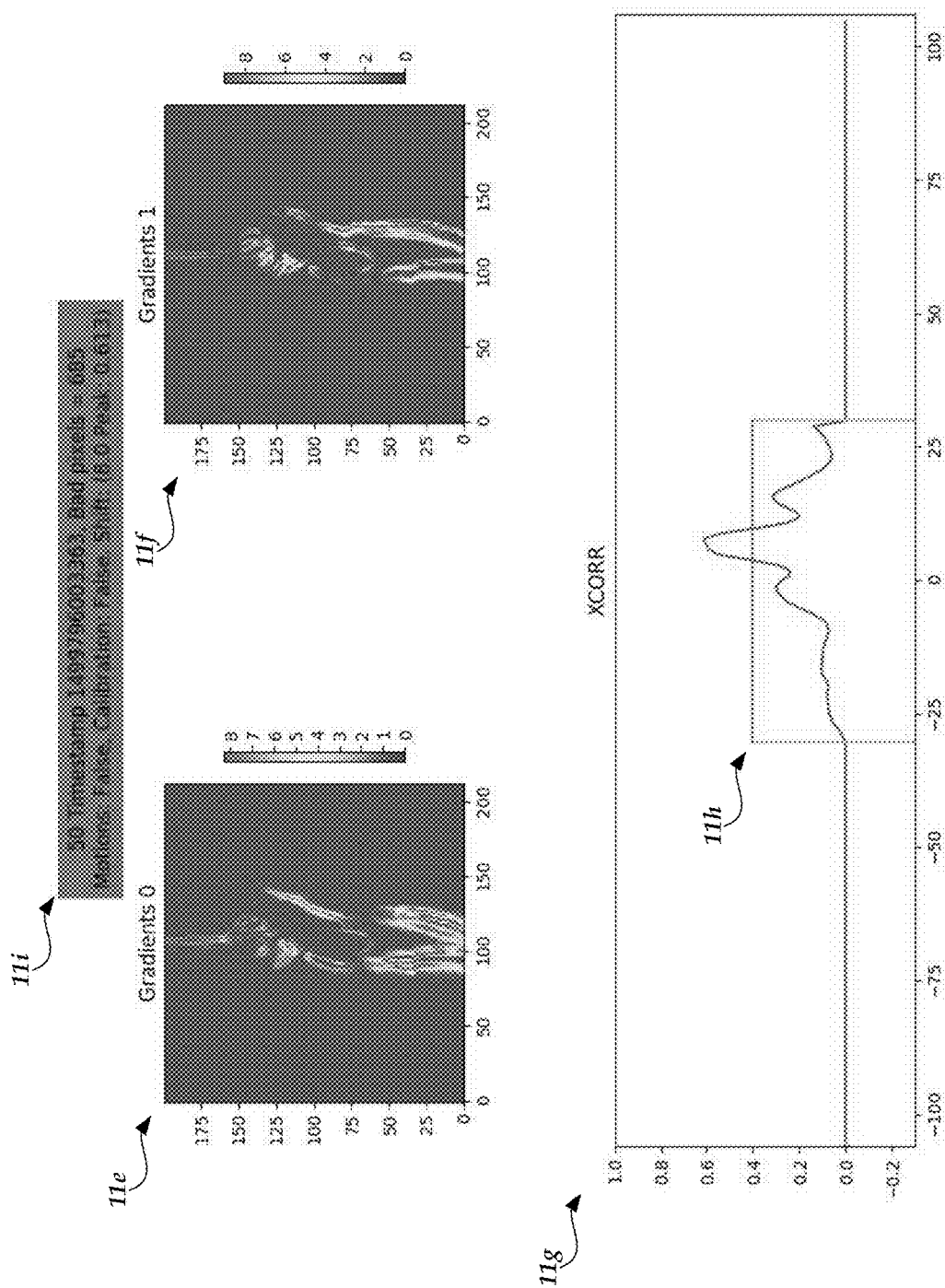

FIGS. 11A and 11B illustrate an example of the WOS alerting method 1002 of FIG. 10 in which a fishing lure is positioned approximately 2 centimeters away from the optical window 1506 of one of the systems 1000.

Image 11a of FIG. 11A may be an image captured from a first WOS channel such as optical channel 6 of FIG. 8B and passed through an unsharp mask (such as in step 1006 of FIG. 10). In image 11a, an outline of the fishing lure is visible, while the background is generally blurred, as the optical channel 6 is focused upon the near-field region including the optical window as described herein.

Image 11b may be a version of image 11a after applying an optional temporal mask (e.g., subtracting out of reference frame as in step 1008 of FIG. 10)). In image 11b, features that do not represent changes from a reference frame have been removed. Thus, in a fixed installation such as the illustrated example, background features and features associated with static objects are removed from image 11b. Generally, these features are not associated objects of interest to the WOS system (e.g., with objects in the near-field region).

Image 11e of FIG. 11B may be a version of image 11b (or 11a if the temporal mask step is skipped) after applying an edge detection mask (e.g., after applying a Sobel filter as in step 1010 of FIG. 10. In image 11e, the soft features and edges of the background have been removed as the soft background features are not associated with objects of interest to the WOS system. Additionally, the sharp edges of the fishing lure have been enhanced. The edges of the fishing lure are generally sharp in the illustrated example as the optical channels associated with the WOS system have their focus set for objects on or near the optical window, which includes objects at a distance of 2 centimeters.

Images 11c and 11d are equivalent versions of images 11a and 11b, respectively, but corresponding to a second WOS channel such as optical channel 7 of FIG. 8B. Similarly image 1 if is an equivalent version of image 11e, but corresponding to the second WOS channel. Thus, images 11c, 11d, and 11f provide similar information, but with a beneficial parallax offset.

As shown in images 11e and 11f, a large number of pixels (as indicated in banner 11i approximately 685 "bad pixels") have a gradient value above the predetermined threshold. These pixels may be referred to herein as bad pixels and may be associated with objects that are in-focus, and thereby known to be within the region of interest for the WOS system.

Graph 11g of FIG. 11B illustrates cross-correlation values for images 11e and 11f as a function of various horizontal offsets. In particular, graph 11g shows the cross-correlation values for horizontal for an offset of −100 to +100, wherein a negative offset may represent an offset of image 11e in a leftward direction by a given number of pixels from the image 11e, while a positive offset may represent an offset of image 11e in a rightward direction.

As shown in graph 11g, the fishing lure at 2 cm example may have a peak cross-correlation value of approximately 0.6 (e.g., a peak value of 0.613 at a positive shift of 8 pixels).

As part of step 1014, the WOS system may determine that the peak cross-correlation value within box 11h (see graph 11g) exceeds the predetermined threshold and that the number of "bad" pixels exceeds the predetermined threshold. As a result, the WOS system may issue a WOS alert, as indicated by box 11i, in the example of FIGS. 11A and 11B.

b. A Fishing Lure at 20 Centimeters

Figure 12A:
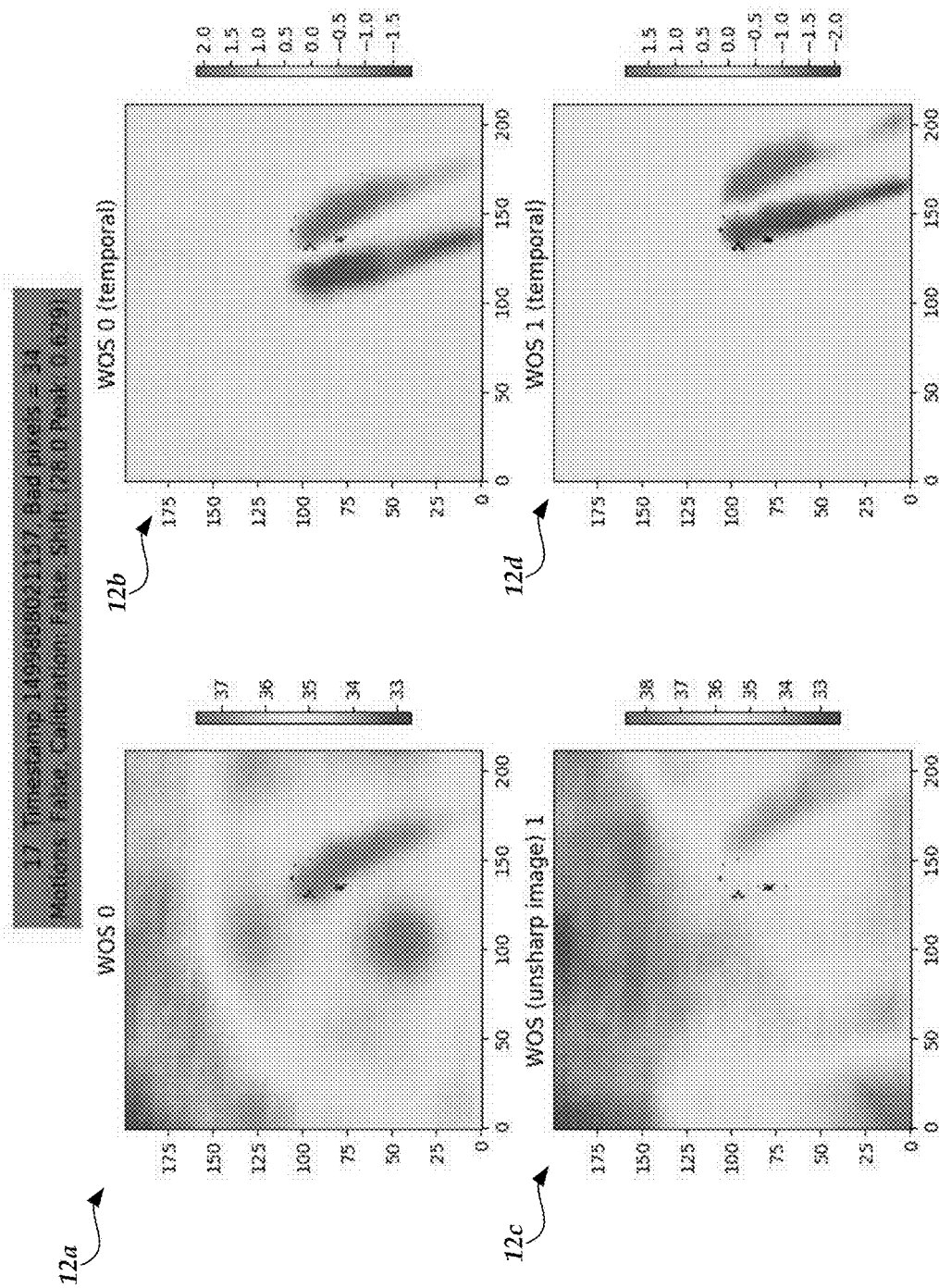
FIGS. 12A and 12B show an example of various stages of processing of data taken by window obscuration sensors with a fishing lure approximately 20 cm away from the optical window.
Figure 12B:
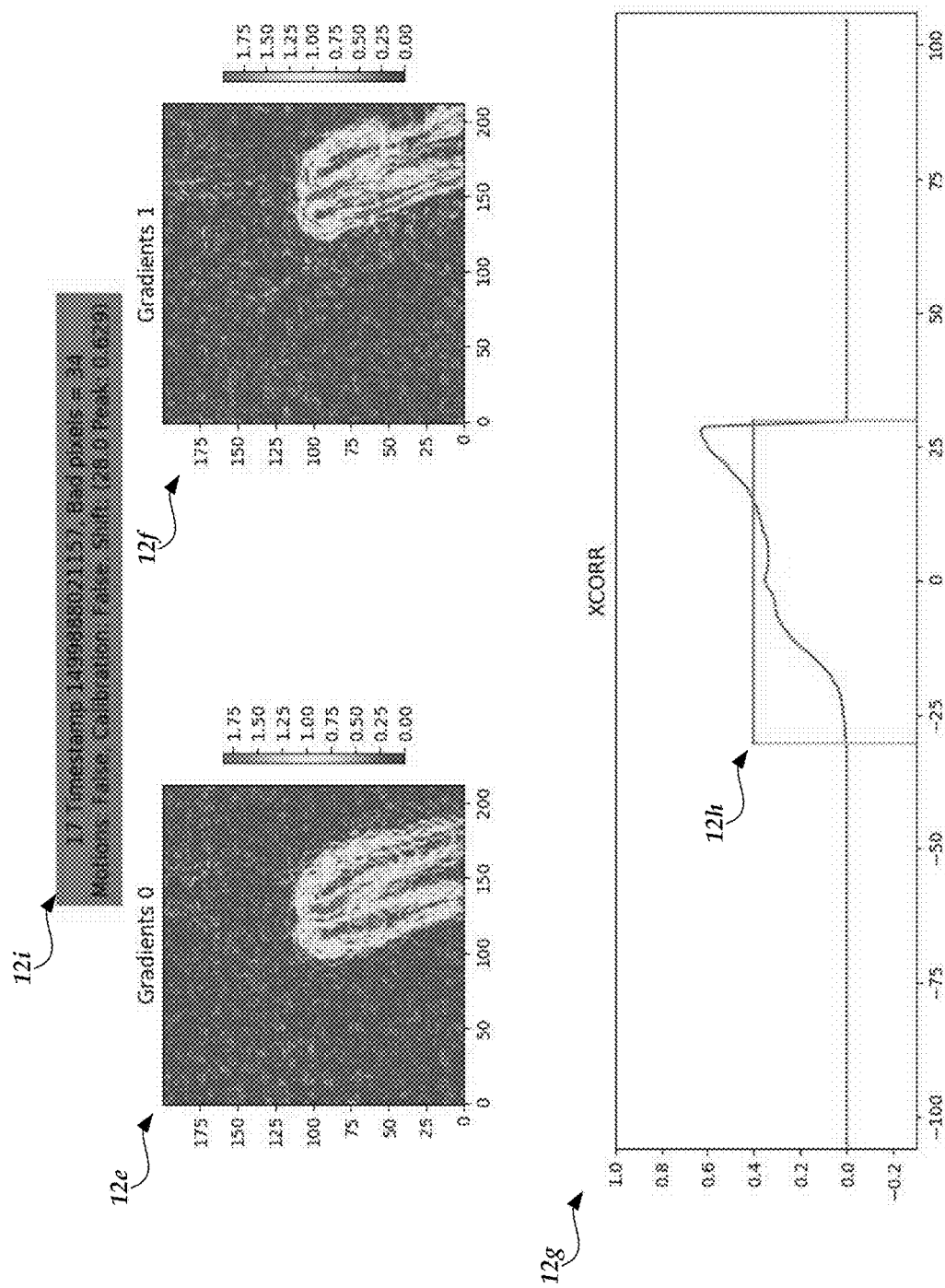

FIGS. 12A and 12B illustrate an example of the WOS alerting method 1002 of FIG. 10 in which a fishing lure is positioned approximately 20 centimeters away from the optical window 1506 of one of the systems 1000.

Image 12a of FIG. 12A may be an image captured from a first WOS channel such as optical channel 6 of FIG. 8B and passed through an unsharp mask (such as in step 1006 of FIG. 10). In image 12a, an outline of the fishing lure is visible, while the background is generally blurred, as the optical channel 6 is focused upon the near-field region including the optical window as described herein.

Image 12b may be a version of image 12a after applying an optional temporal mask (e.g., subtracting out of reference frame as in step 1008 of FIG. 10)). In image 12b, features that do not represent changes from a reference frame have been removed. Thus, in a fixed installation such as the illustrated example, background features and features associated with static objects are removed from image 12b. Generally, these features are not associated objects of interest to the WOS system (e.g., with objects in the near-field region).

Image 12e of FIG. 12B may be a version of image 12b (or 12a if the temporal mask step is skipped) after applying an edge detection mask (e.g., after applying a Sobel filter as in step 1010 of FIG. 10. In image 12e, the soft features and edges of the background have been removed as the soft background features are not associated with objects of interest to the WOS system. Additionally, the sharp edges of the fishing lure have been enhanced. The edges of the fishing lure are generally sharp in the illustrated example as the optical channels associated with the WOS system have their focus set for objects on or near the optical window, which includes objects at a distance of 20 centimeters.

Images 12c and 12d are equivalent versions of images 12a and 12b, respectively, but corresponding to a second WOS channel such as optical channel 7 of FIG. 8B. Similarly image 12f is an equivalent version of image 12e, but corresponding to the second WOS channel. Thus, images 12c, 12d, and 12f provide similar information, but with a beneficial parallax offset.

As shown in images 12e and 12f, a large number of pixels (indicated in banner 12i) have a gradient value above the predetermined threshold (e.g., 34 "bad pixels" as indicated in banner 12i). These pixels may be referred to herein as bad pixels and may be associated with objects that are in-focus, and thereby known to be within the region of interest for the WOS system.

Graph 12g of FIG. 12B illustrates cross-correlation values for images 12e and 12f as a function of various horizontal offsets. In particular, graph 12g shows the cross-correlation values for horizontal for an offset of −100 to +100, wherein a negative offset may represent an offset of image 12e in a leftward direction by a given number of pixels from the image 12e, while a positive offset may represent an offset of image 12e in a rightward direction.

As shown in graph 12g, the fishing lure at 20 cm example may have a peak cross-correlation value of approximately 0.6 (e.g., a peak of 0.629 at a shift of +28 pixels). Moreover, in comparison to graph 11g of FIG. 11B, the peak may be shifted towards a larger horizontal offset (e.g., the peak may be closer to a +30 pixel shift in graph 12g, as opposed to around +5 pixels in graph 11g). This shift may be associated with the increased distance of 20 cm in the example of FIGS. 12A and 12B, relative to the example at 2 cm.

As part of step 1014, the WOS system may determine that the peak cross-correlation value within box 12h (see graph 12g) exceeds the predetermined threshold and that the number of "bad" pixels exceeds the predetermined threshold. As a result, the WOS system may issue a WOS alert, as indicated by box 12i, in the example of FIGS. 12A and 12B.

c. A Fishing Lure at 50 Centimeters

Figure 13A:
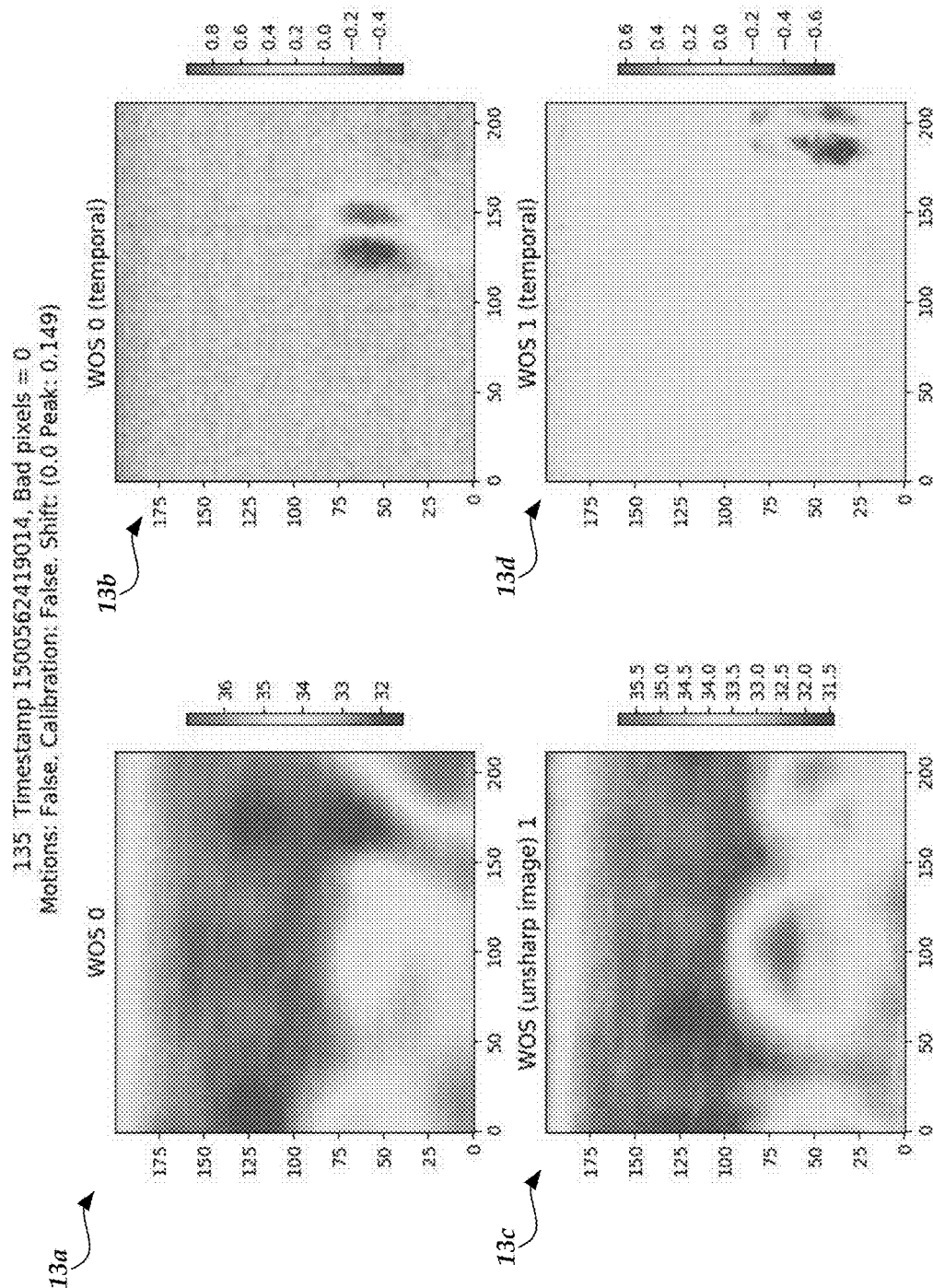
FIGS. 13A and 13B show an example of various stages of processing of data taken by window obscuration sensors with a fishing lure approximately 50 cm away from the optical window.
Figure 13B:
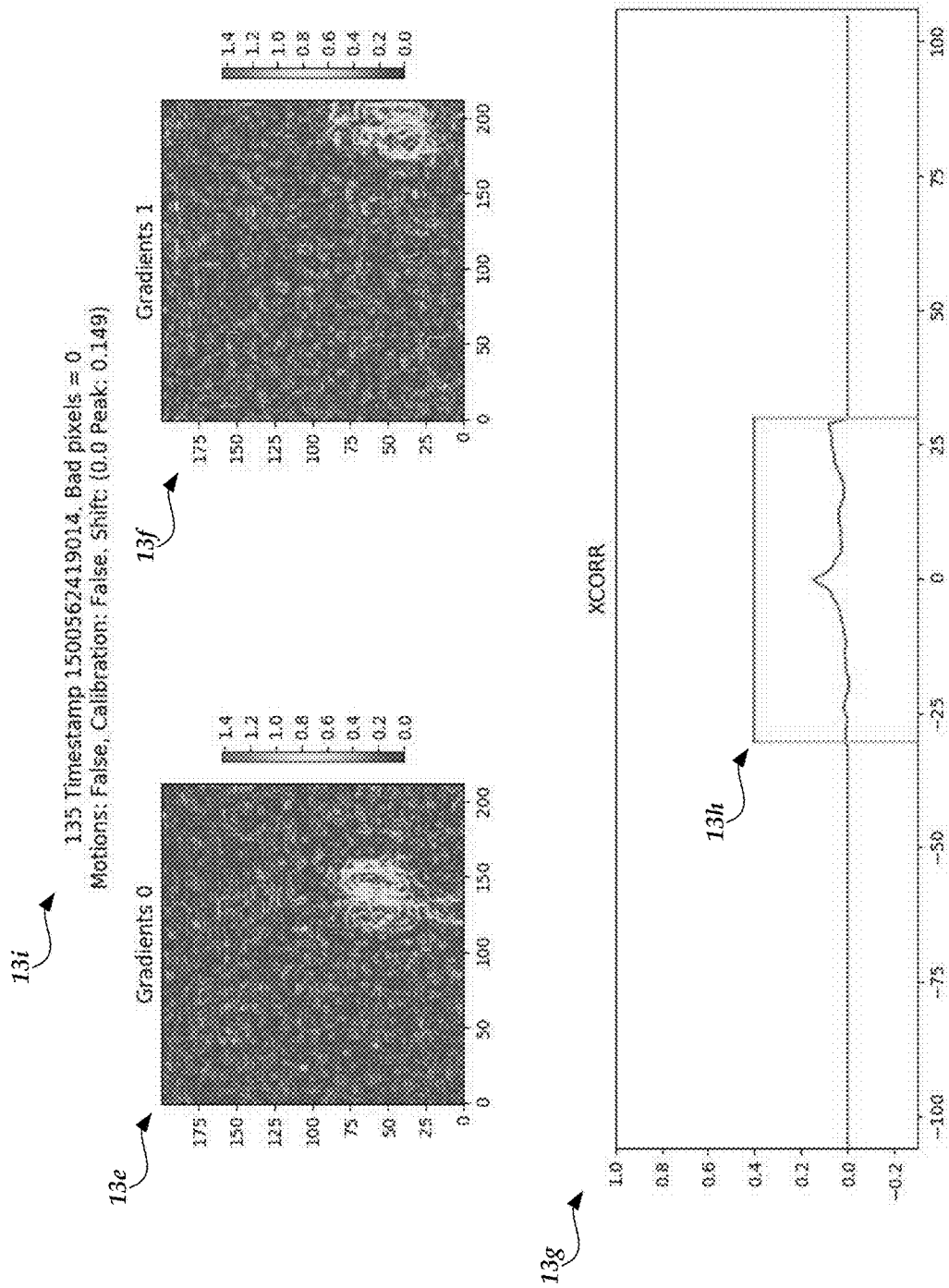

FIGS. 13A and 13B illustrate an example of the WOS alerting method 1002 of FIG. 10 in which a fishing lure is positioned approximately 50 centimeters away from the optical window 1506 of one of the systems 1000.

Image 13a of FIG. 13A may be an image captured from a first WOS channel such as optical channel 6 of FIG. 8B and passed through an unsharp mask (such as in step 1006 of FIG. 10). In image 13a, an outline of the fishing lure is just barely visible and is nearly as blurred as the background, as the optical channel 6 is focused upon the near-field region including the optical window as described herein.

Image 13b may be a version of image 13a after applying an optional temporal mask (e.g., subtracting out of reference frame as in step 1008 of FIG. 10)). In image 13b, features that do not represent changes from a reference frame have been removed. Thus, in a fixed installation such as the illustrated example, background features and features associated with static objects are removed from image 13b. Generally, these features are not associated objects of interest to the WOS system (e.g., with objects in the near-field region). In the example of FIG. 13A, the temporal mask has the effect of highlighting the fishing lure in image 13b.

Image 13e of FIG. 13B may be a version of image 13b (or 13a if the temporal mask step is skipped) after applying an edge detection mask (e.g., after applying a Sobel filter as in step 1010 of FIG. 10. In image 13e, the soft features and edges of the background have been removed as the soft background features are not associated with objects of interest to the WOS system. Additionally, the somewhat blurry edges of the fishing lure are somewhat sharpened. However, since the fishing lure is generally out of the focal range of the WOS system at 50 centimeters, its edges are somewhat blurry.

Images 13c and 13d are equivalent versions of images 13a and 13b, respectively, but corresponding to a second WOS channel such as optical channel 7 of FIG. 8B. Similarly image 13f is an equivalent version of image 13e, but corresponding to the second WOS channel. Thus, images 13c, 13d, and 13f provide similar information, but with a beneficial parallax offset.

As shown in images 13e and 13f, very few if any pixels (indicated in banner 13i) have a gradient value above the predetermined threshold (e.g., 0 "bad pixels" as indicated in banner 13i). In particular, there are very few, if any, edges that are sufficiently sharp in images 13e and 13f. Thus, the system can conclude that there are no objects within the region of interest near or on the optical window. As such, the WOW system may determine that no WOS alert is needed based on the lack of such edges (e.g., the lack of "bad" pixels in the gradient images). Nonetheless, the system may continue with WOS processing including calculation of cross-correlation values.

Graph 13g of FIG. 13B illustrates cross-correlation values for images 13e and 13f as a function of various horizontal offsets. In particular, graph 13g shows the cross-correlation values for horizontal for an offset of −100 to +100, wherein a negative offset may represent an offset of image 13e in a leftward direction by a given number of pixels from the image 13e, while a positive offset may represent an offset of image 13e in a rightward direction.

As shown in graph 13g, the fishing lure at 50 cm example may have a peak cross-correlation value of approximately 0.2 (e.g., a peak of 0.149 at a zero offset). As such, the cross-correlation value may not exceed the predetermined threshold indicated by box 13h and the system may decide not to provide a WOS alert.

d. A Tennis Racket at 2 Centimeters

Figure 14A:
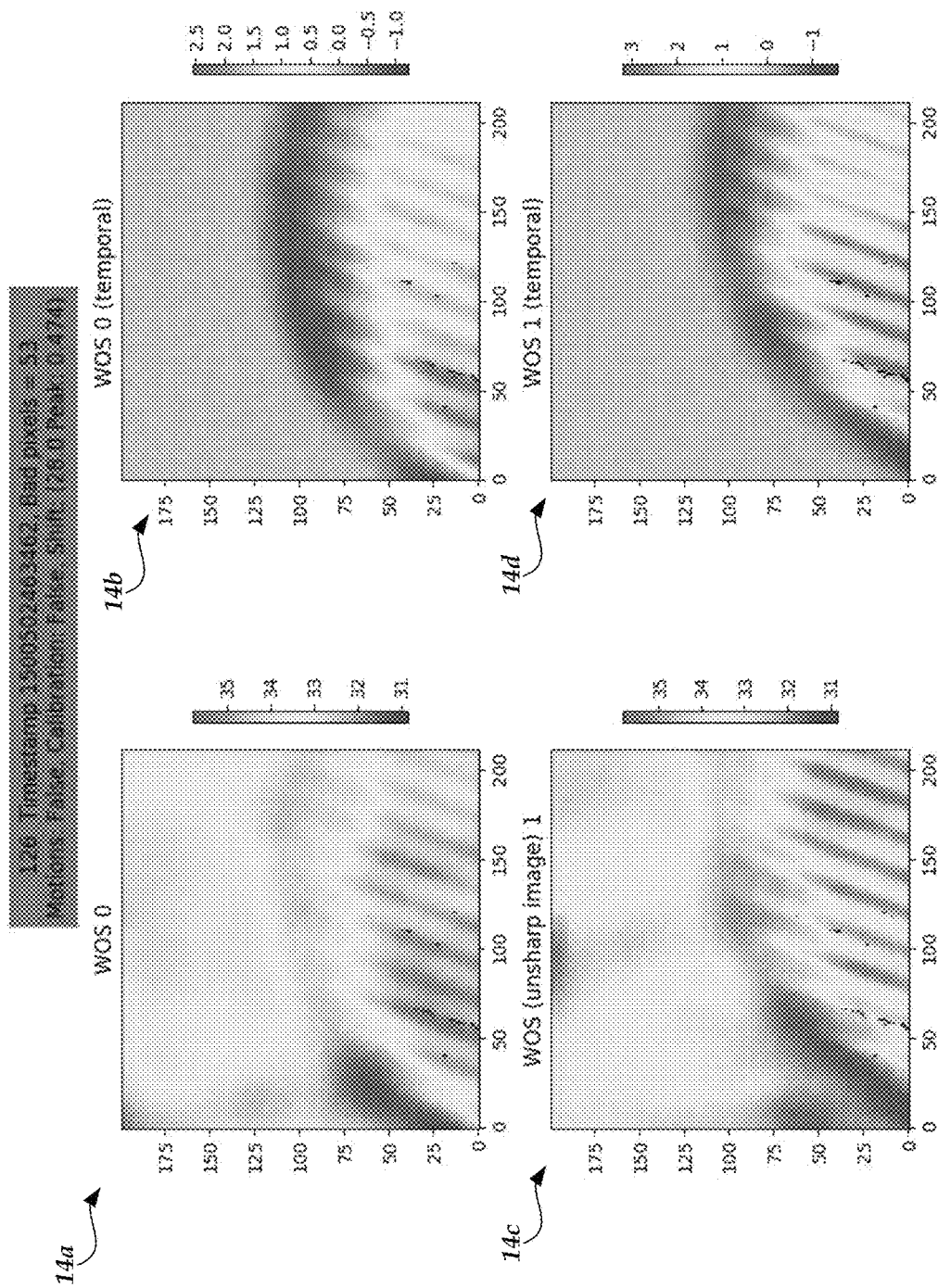
FIGS. 14A and 14B show an example of various stages of processing of data taken by window obscuration sensors with a tennis racket approximately 2 cm away from the optical window.
Figure 14B:
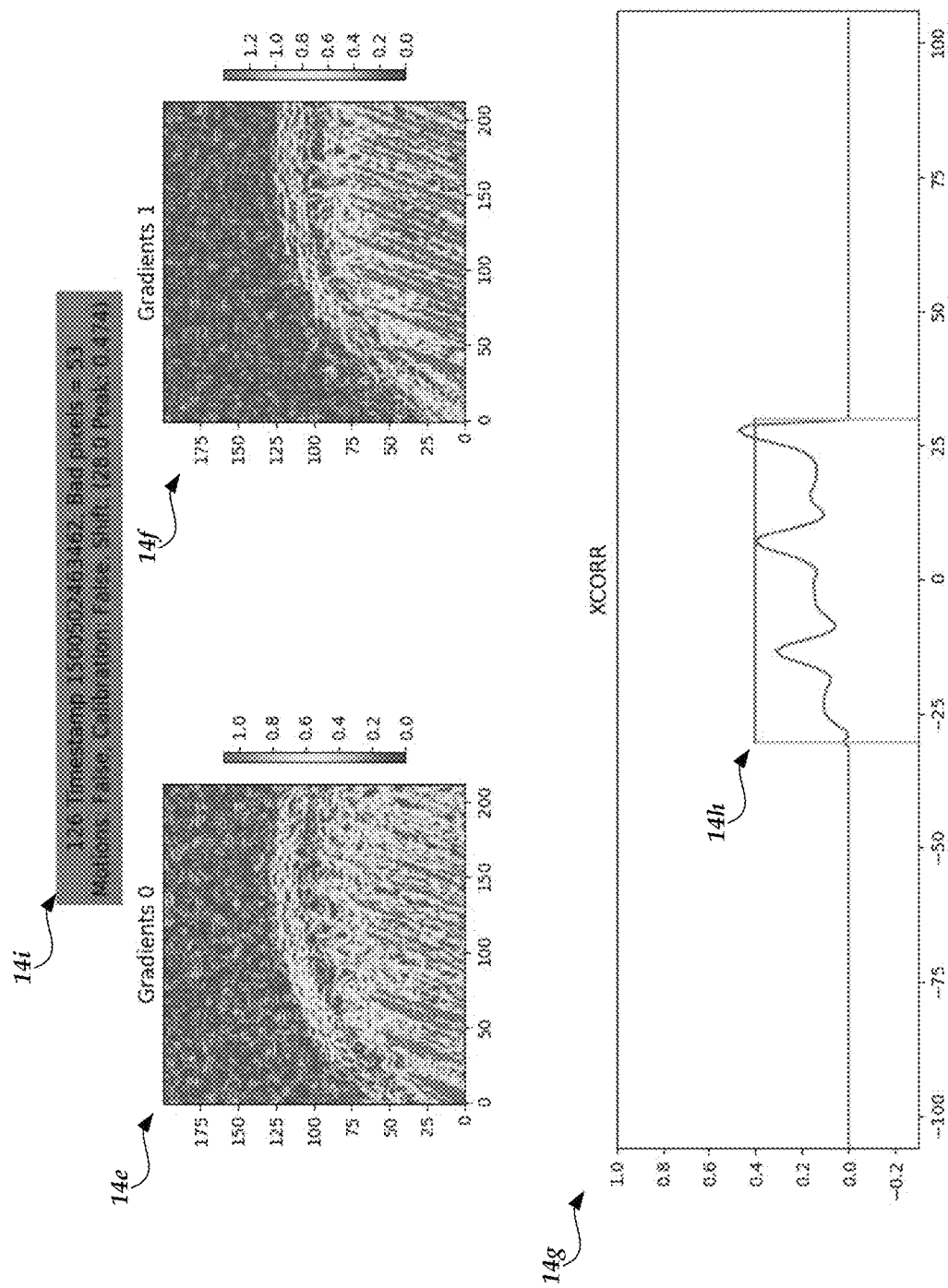

FIGS. 14A and 14B illustrate an example of the WOS alerting method 1002 of FIG. 10 in which a tennis racket is positioned approximately 2 centimeters away from the optical window 1506 of one of the systems 1000.

Image 14a of FIG. 14A may be an image captured from a first WOS channel such as optical channel 6 of FIG. 8B and passed through an unsharp mask (such as in step 1006 of FIG. 10). In image 14a, an outline of the tennis racket is visible, while the background is generally blurred, as the optical channel 6 is focused upon the near-field region including the optical window as described herein.

Image 14b may be a version of image 14a after applying an optional temporal mask (e.g., subtracting out of reference frame as in step 1008 of FIG. 10)). In image 14b, features that do not represent changes from a reference frame have been removed. Thus, in a fixed installation such as the illustrated example, background features and features associated with static objects are removed from image 14b. Generally, these features are not associated objects of interest to the WOS system (e.g., with objects in the near-field region).

Image 14e of FIG. 14B may be a version of image 14b (or 14a if the temporal mask step is skipped) after applying an edge detection mask (e.g., after applying a Sobel filter as in step 1010 of FIG. 10. In image 14e, the soft features and edges of the background have been removed as the soft background features are not associated with objects of interest to the WOS system. Additionally, the sharp edges of the tennis racket have been enhanced. The edges of the tennis racket are generally sharp in the illustrated example as the optical channels associated with the WOS system have their focus set for objects on or near the optical window, which includes objects at a distance of 2 centimeters.

Images 14c and 14d are equivalent versions of images 14a and 14b, respectively, but corresponding to a second WOS channel such as optical channel 7 of FIG. 8B. Similarly image 14f is an equivalent version of image 14e, but corresponding to the second WOS channel. Thus, images 14c, 14d, and 14f provide similar information, but with a beneficial parallax offset.

As shown in images 14e and 14f, a large number of pixels (indicated in banner 14i) have a gradient value above the predetermined threshold (e.g., 53 "bad pixels" as shown in banner 14i). These pixels may be referred to herein as bad pixels and may be associated with objects that are in-focus, and thereby known to be within the region of interest for the WOS system.

Graph 14g of FIG. 14B illustrates cross-correlation values for images 14e and 14f as a function of various horizontal offsets. In particular, graph 14g shows the cross-correlation values for horizontal for an offset of −100 to +100, wherein a negative offset may represent an offset of image 14e in a leftward direction by a given number of pixels from the image 14e, while a positive offset may represent an offset of image 14e in a rightward direction.

As shown in graph 14g, the tennis racket at 2 cm example may have a peak cross-correlation value of approximately 0.5 (e.g., a peak of 0.474 at a pixel shift of +28). Additionally, given the repeating pattern of the strings of the tennis racket, the gradient images have multiple cross-correlation peaks as shown in graph 14. Nonetheless, the system may still trigger a WOS alert.

As part of step 1014, the WOS system may determine that the peak cross-correlation value within box 14h (see graph 14g) exceeds the predetermined threshold and that the number of "bad" pixels exceeds the predetermined threshold. As a result, the WOS system may issue a WOS alert, as indicated by box 14i, in the example of FIGS. 14A and 14B.

e. A Moving Object at 2 Meters

Figure 15A:
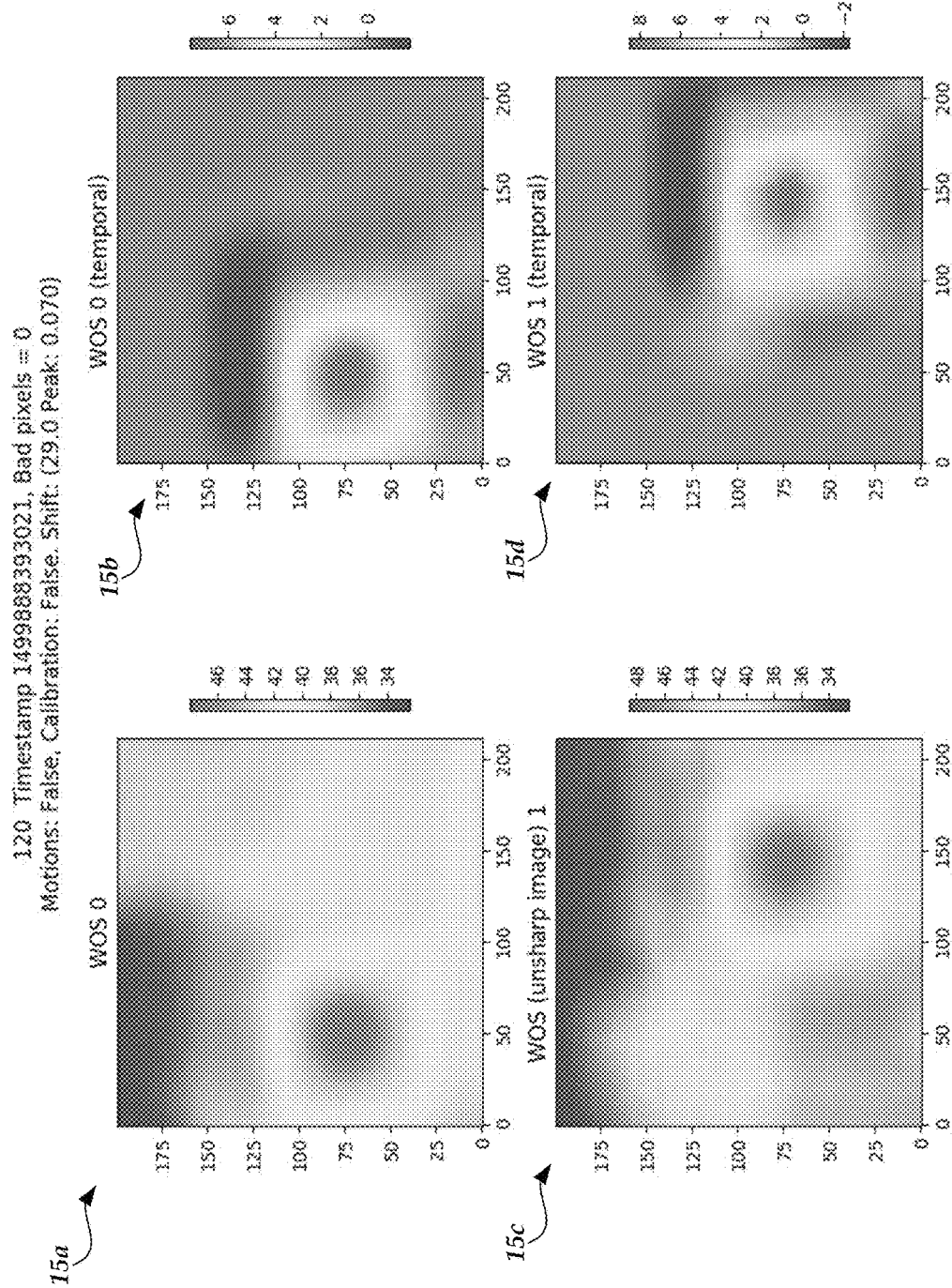
FIGS. 15A and 15B show an example of various stages of processing of data taken by window obscuration sensors with a moving object approximately 2 meters away from the optical window.
Figure 15B:
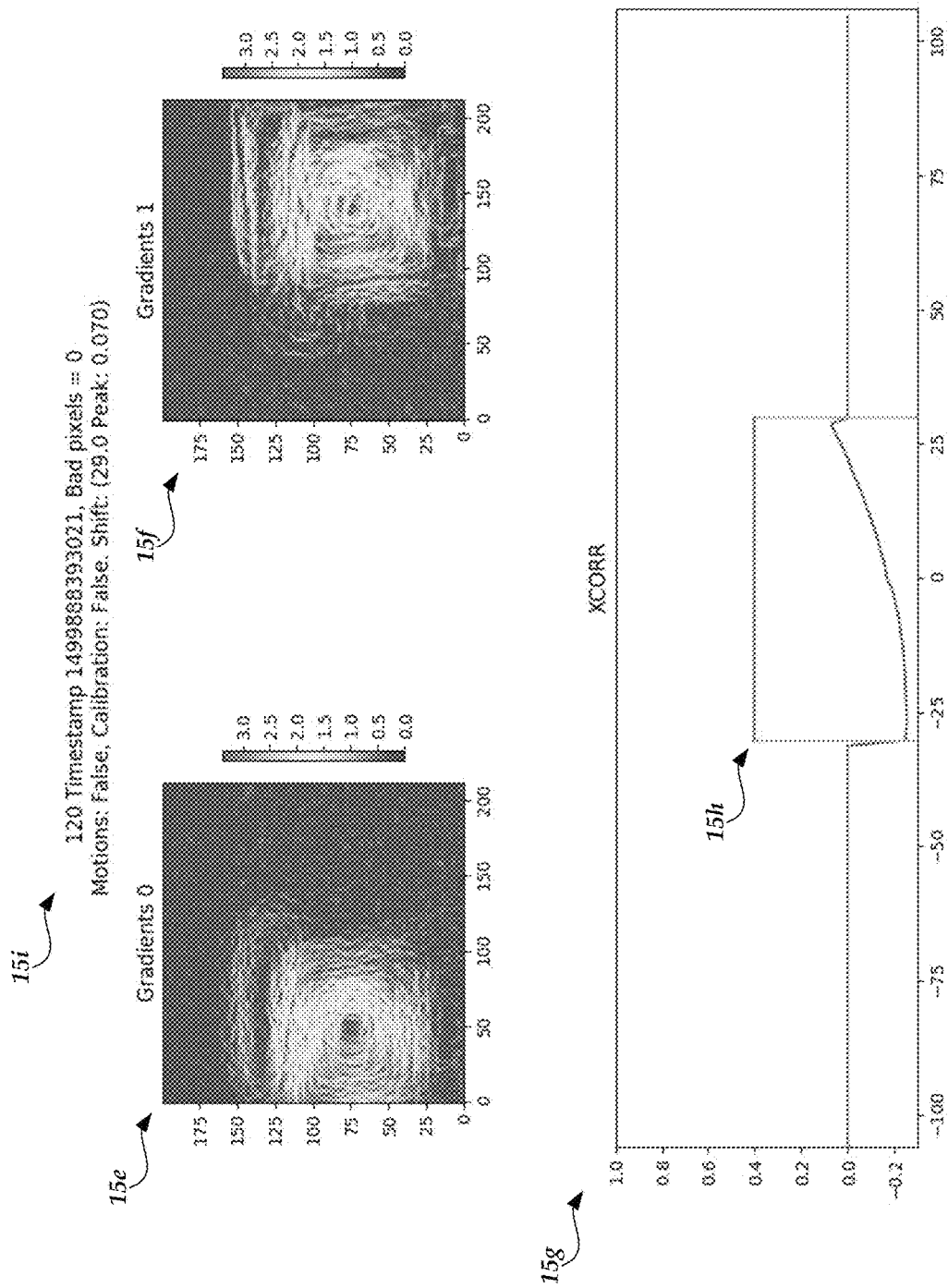

FIGS. 15A and 15B illustrate an example of the WOS alerting method 1002 of FIG. 10 in which a moving object is positioned approximately 2 meters away from the optical window 1506 of one of the systems 1000.

Image 15a of FIG. 15A may be an image captured from a first WOS channel such as optical channel 6 of FIG. 8B and passed through an unsharp mask (such as in step 1006 of FIG. 10). In image 15a, an outline of the moving object is visible, while the background is generally blurred, as the optical channel 6 is focused upon the near-field region including the optical window as described herein.

Image 15b may be a version of image 15a after applying an optional temporal mask (e.g., subtracting out of reference frame as in step 1008 of FIG. 10)). In image 15b, features that do not represent changes from a reference frame have been removed. Thus, in a fixed installation such as the illustrated example, background features and features associated with static objects are removed from image 15b.

Image 15e of FIG. 15B may be a version of image 15b (or 15a if the temporal mask step is skipped) after applying an edge detection mask (e.g., after applying a Sobel filter as in step 1010 of FIG. 10. In image 15e, the soft features and edges of the background have been removed as the soft background features are not associated with objects of interest to the WOS system. As illustrated, the moving object (which is too far from the system to be in focus for the WOS channels) has relatively soft edges.

Images 15c and 15d are equivalent versions of images 15a and 15b, respectively, but corresponding to a second WOS channel such as optical channel 7 of FIG. 8B. Similarly image 15f is an equivalent version of image 15e, but corresponding to the second WOS channel. Thus, images 15c, 15d, and 15f provide similar information, but with a beneficial parallax offset.

As shown in images 15e and 15f, few if any of the pixels (also indicated in banner 15i) have a gradient value above the predetermined threshold (e.g., 0 "bad pixels"). In particular, since the moving object is relatively far away from the optical window, the moving object is not in sharp focus and can't provide sharp edges. As such, the WOS system may decide not to issue a WOS alert, as there are insufficient sharp edges present in the gradient images.

Graph 15g of FIG. 15B illustrates cross-correlation values for images 15e and 15f as a function of various horizontal offsets. In particular, graph 15g shows the cross-correlation values for horizontal for an offset of −100 to +100, wherein a negative offset may represent an offset of image 15e in a leftward direction by a given number of pixels from the image 15e, while a positive offset may represent an offset of image 15e in a rightward direction.

As shown in graph 15g, the moving object at 2 m example may have a peak cross-correlation value of approximately 0.1 (e.g., a peak of 0.070 at a pixel shift of +29). This peak may be less than needed to satisfy the conditions applied in step 1015. As such, the WOS system may determine that the peak cross-correlation value within box 15h (see graph 15g) does not exceed the predetermined threshold. As a result, the WOS system may decide not to issue a WOS alert, as indicated by box 15i, in the example of FIGS. 15A and 15B.

f. Water Droplets on the Optical Window

Figure 16A:
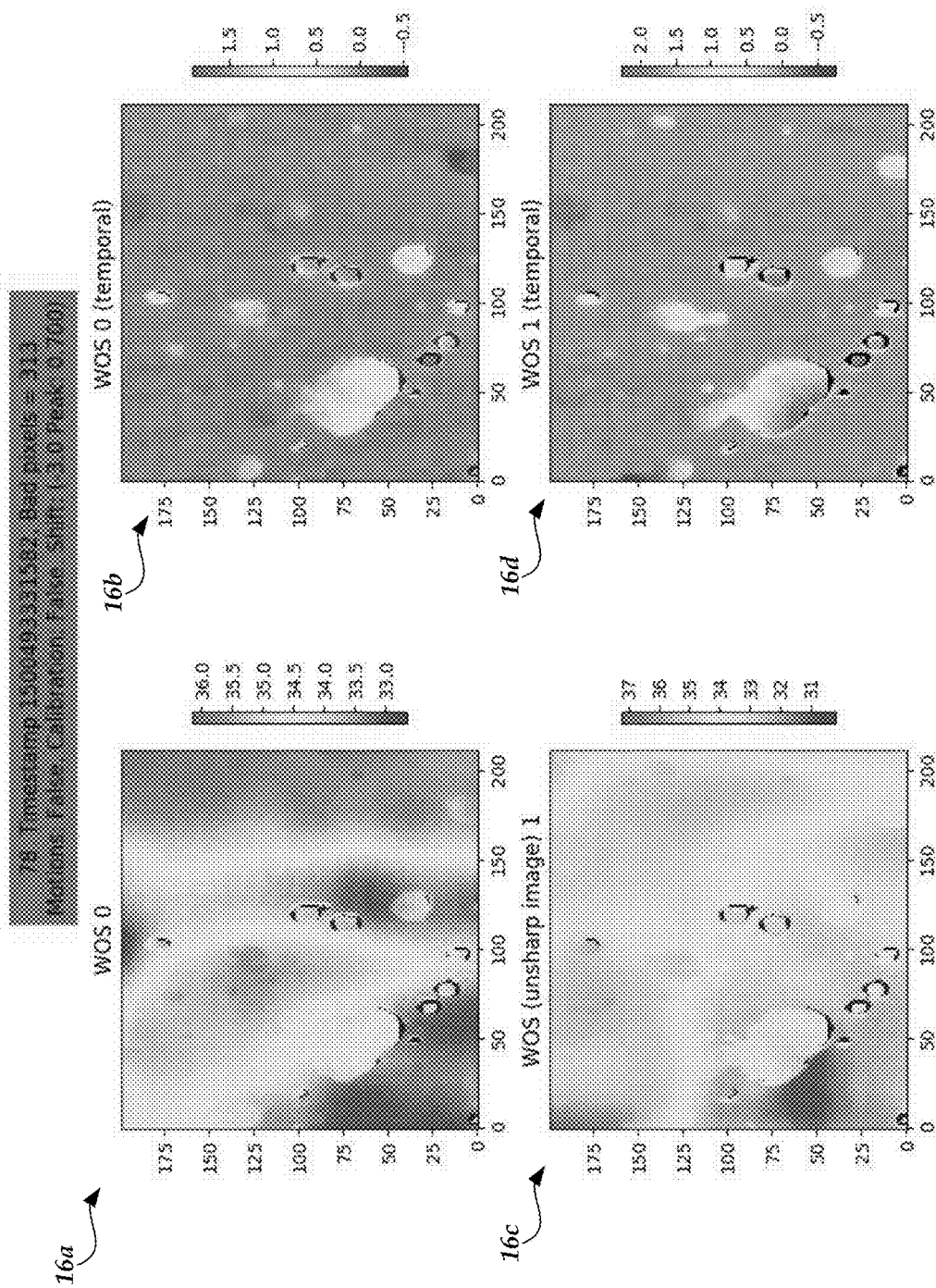
FIGS. 16A, 16B, 17A, and 17B show an example of various stages of processing of data taken by window obscuration sensors with water drops sprinkled onto the optical window.
Figure 16B:
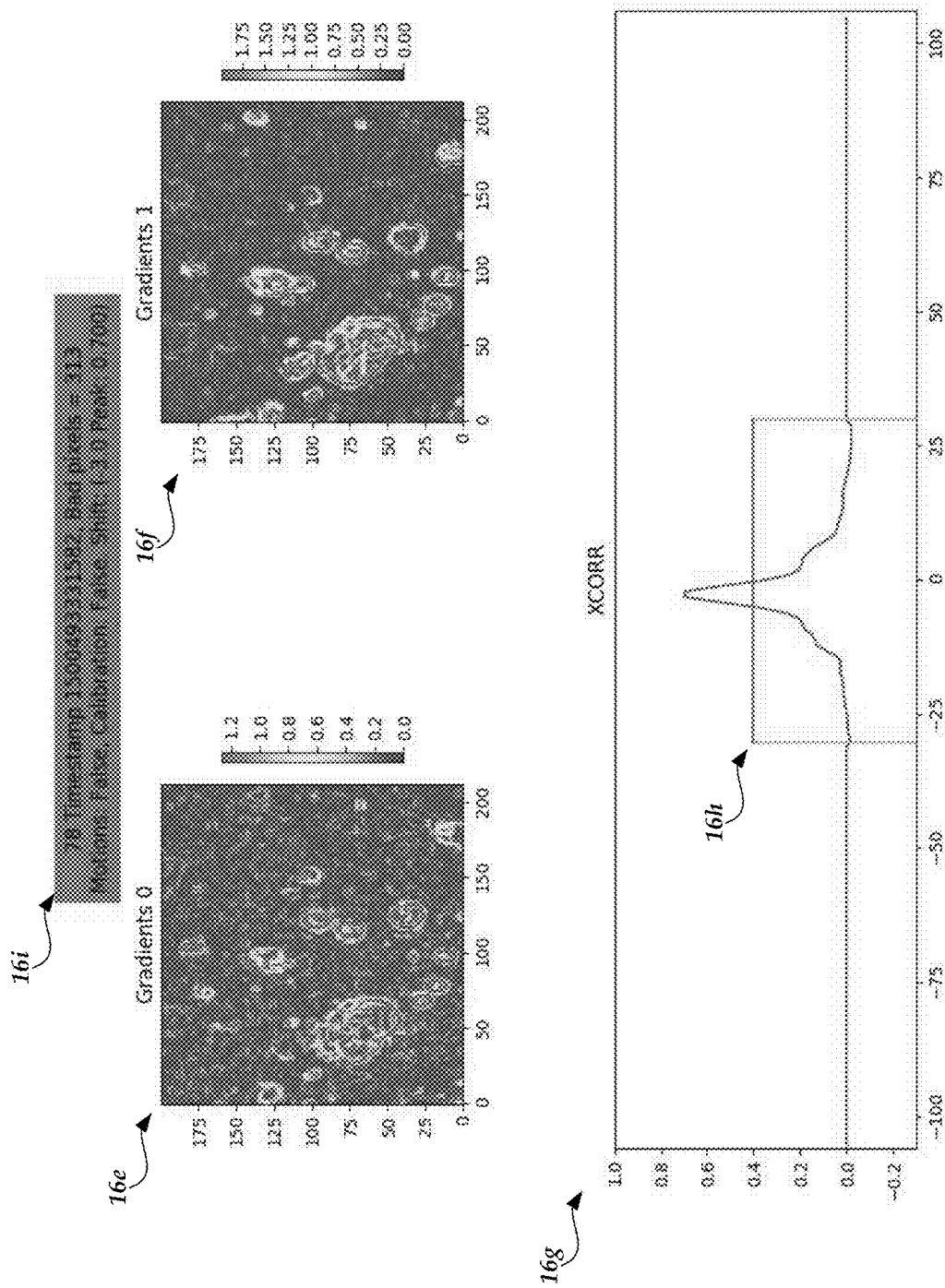

FIGS. 16A and 16B illustrate an example of the WOS alerting method 1002 of FIG. 10 in which water droplets are sprinkled onto the optical window 1506 of one of the systems 1000.

Image 16a of FIG. 16A may be an image captured from a first WOS channel such as optical channel 6 of FIG. 8B and passed through an unsharp mask (such as in step 1006 of FIG. 10). In image 16a, the water droplets are visible, while the background is generally blurred, as the optical channel 6 is focused upon the near-field region including the optical window as described herein.

Image 16b may be a version of image 16a after applying an optional temporal mask (e.g., subtracting out of reference frame as in step 1008 of FIG. 10)). In image 16b, features that do not represent changes from a reference frame have been removed. Thus, in a fixed installation such as the illustrated example, background features and features associated with static objects are removed from image 16b. Generally, these features are not associated objects of interest to the WOS system (e.g., with objects in the near-field region).

Image 16e of FIG. 16B may be a version of image 16b (or 16a if the temporal mask step is skipped) after applying an edge detection mask (e.g., after applying a Sobel filter as in step 1010 of FIG. 10. In image 16e, the soft features and edges of the background have been removed as the soft background features are not associated with objects of interest to the WOS system. Additionally, the sharp edges of the water drops have been enhanced. The edges of the water drops are generally sharp in the illustrated example, because the optical channels associated with the WOS system have their focus set for objects on or near the optical window, which includes objects on the optical window.

Images 16*c* and 16*d* are equivalent versions of images 16*a* and 16*b*, respectively, but corresponding to a second WOS channel such as optical channel 7 of FIG. 8B. Similarly image 16*f* is an equivalent version of image 16*e*, but corresponding to the second WOS channel. Thus, images 16*c*, 16*d*, and 16*f* provide similar information, but with a beneficial parallax offset.

As shown in images 16*e* and 16*f*, a large number of pixels (indicated in banner 16*i*) have a gradient value above the predetermined threshold (e.g., 313 bad pixels). These pixels may be referred to herein as bad pixels and may be associated with objects that are in-focus, and thereby known to be within the region of interest for the WOS system.

Graph 16*g* of FIG. 16B illustrates cross-correlation values for images 16*e* and 16*f* as a function of various horizontal offsets. In particular, graph 16*g* shows the cross-correlation values for horizontal for an offset of −100 to +100, wherein a negative offset may represent an offset of image 16*e* in a leftward direction by a given number of pixels from the image 16*e*, while a positive offset may represent an offset of image 16*e* in a rightward direction.

As shown in graph 16*g*, the example with water droplets on the optical window may have a peak cross-correlation value of approximately 0.7 (e.g., a peak of 0.700 at a pixel offset of −3).

As part of step 1014, the WOS system may determine that the peak cross-correlation value within box 16*h* (see graph 16*g*) exceeds the predetermined threshold and that the number of "bad" pixels exceeds the predetermined threshold. As a result, the WOS system may issue a WOS alert, as indicated by box 16*i*, in the example of FIGS. 16A and 16B.

g. A Second Example of Water Droplets on the Optical Window

Figure 17A:
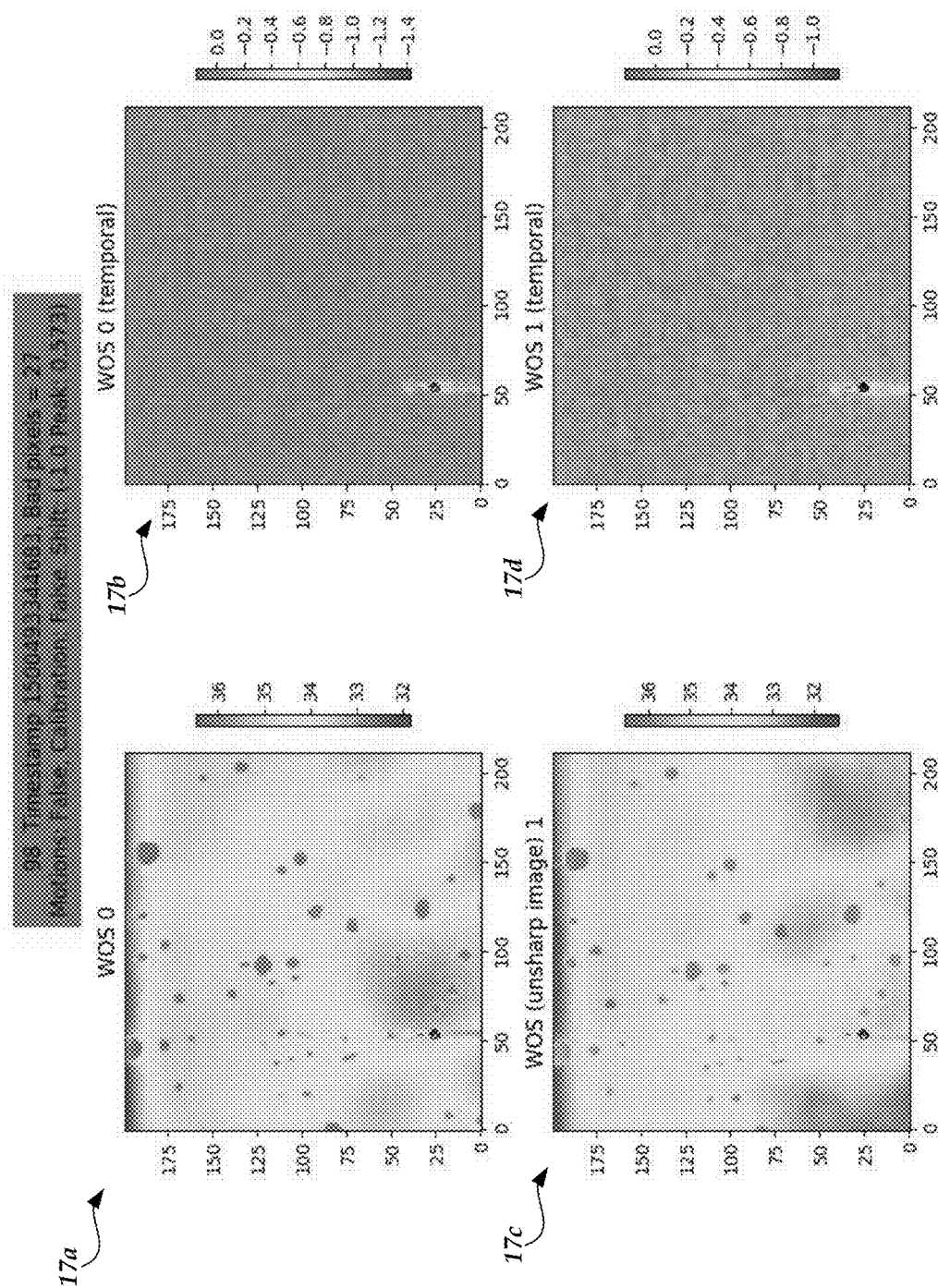
Figure 17B:
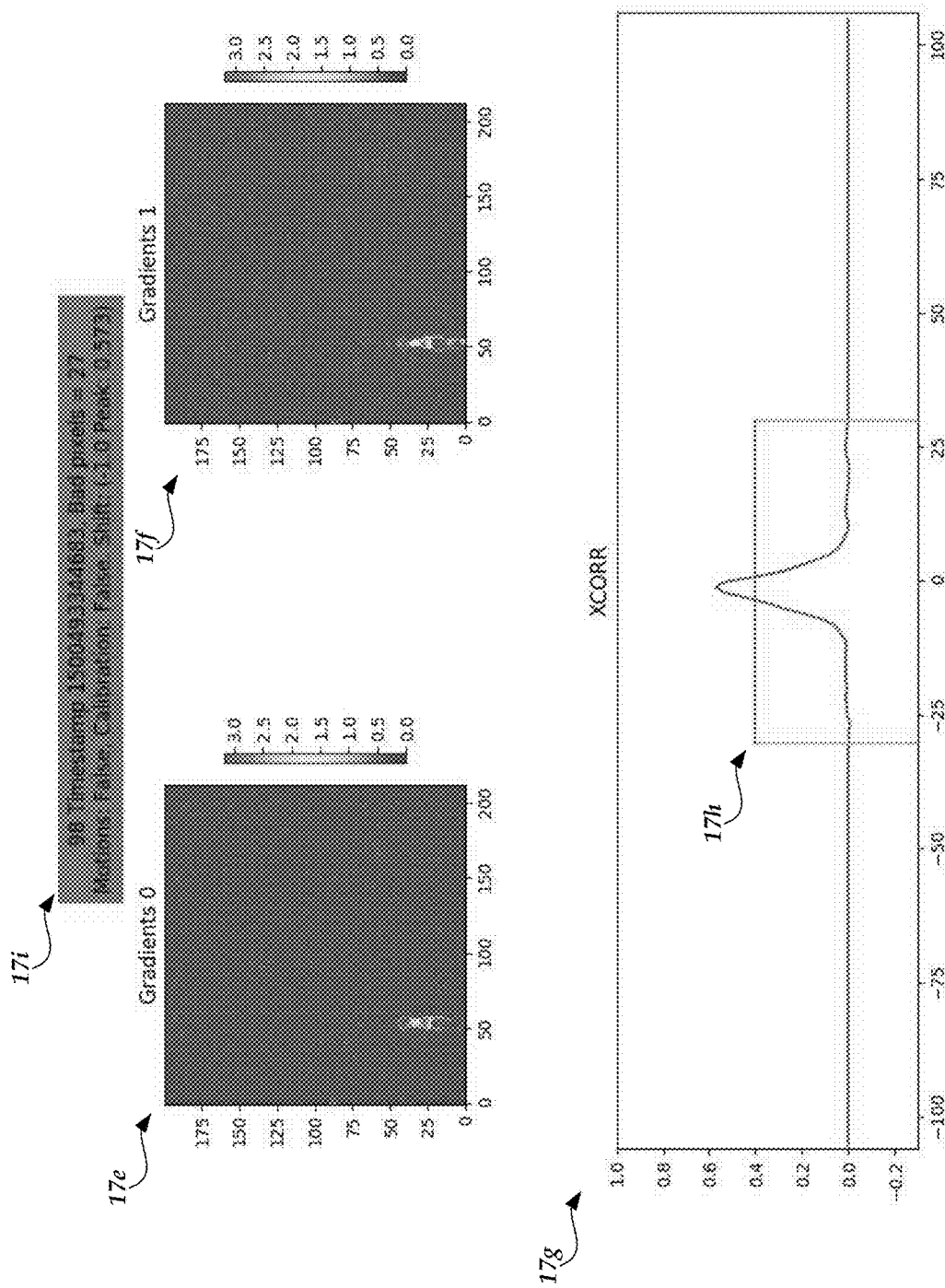

FIGS. 17A and 17B illustrate a second example in which water droplets are sprinkled onto the optical window 1506 of one of the systems 1000.

Image 17*a* of FIG. 17A may be an image captured from a first WOS channel such as optical channel 6 of FIG. 8B and passed through an unsharp mask (such as in step 1006 of FIG. 10). In image 17*a*, the water droplets are visible, while the background is generally blurred, as the optical channel 6 is focused upon the near-field region including the optical window as described herein.

Image 17*b* may be a version of image 17*a* after applying an optional temporal mask (e.g., subtracting out of reference frame as in step 1008 of FIG. 10)). In image 17*b*, features that do not represent changes from a reference frame have been removed. Thus, in a fixed installation such as the illustrated example, background features and features associated with static objects are removed from image 17*b*. Generally, these features are not associated objects of interest to the WOS system (e.g., with objects in the near-field region). In the particular example if image 17*b*, the temporal mask may also filter out water droplets that are stationary and have been incorporated into the reference image. Nonetheless, the WOS system is still able to generate a WOS alert, as discussed below in connection with FIG. 17B.

Image 17*e* of FIG. 17B may be a version of image 17*b* (or 17*a* if the temporal mask step is skipped) after applying an edge detection mask (e.g., after applying a Sobel filter as in step 1010 of FIG. 10. In image 17*e*, the soft features and edges of the background have been removed as the soft background features are not associated with objects of interest to the WOS system. Additionally, the sharp edges of the water drops have been enhanced.

Images 17*c* and 17*d* are equivalent versions of images 17*a* and 17*b*, respectively, but corresponding to a second WOS channel such as optical channel 7 of FIG. 8B. Similarly image 17*f* is an equivalent version of image 17*e*, but corresponding to the second WOS channel. Thus, images 17*c*, 17*d*, and 17*f* provide similar information, but with a beneficial parallax offset.

As shown in images 17*e* and 17*f*, a sufficient number of pixels (indicated in banner 17*i*) have a gradient value above the predetermined threshold to trigger a WOS alarm (e.g., 27 "bad pixels" as shown in banner 17*i*).

Graph 17*g* of FIG. 17B illustrates cross-correlation values for images 17*e* and 17*f* as a function of various horizontal offsets. In particular, graph 17*g* shows the cross-correlation values for horizontal for an offset of −100 to +100, wherein a negative offset may represent an offset of image 17*e* in a leftward direction by a given number of pixels from the image 17*e*, while a positive offset may represent an offset of image 17*e* in a rightward direction.

As shown in graph 17*g*, the second example with water droplets on the optical window may have a peak cross-correlation value of approximately 0.6 (e.g., a peak of 0.573 at a shift of −1 pixels), again sufficient to trigger a WOS alarm.

As part of step 1014, the WOS system may determine that the peak cross-correlation value within box 17*h* (see graph 17*g*) exceeds the predetermined threshold and that the number of "bad" pixels exceeds the predetermined threshold. As a result, the WOS system may issue a WOS alert, as indicated by box 17*i*, in the example of FIGS. 17A and 17B.

h. Water Droplets on the Optical Window with a Fishing Lure at 50 Centimeters

Figure 18A:
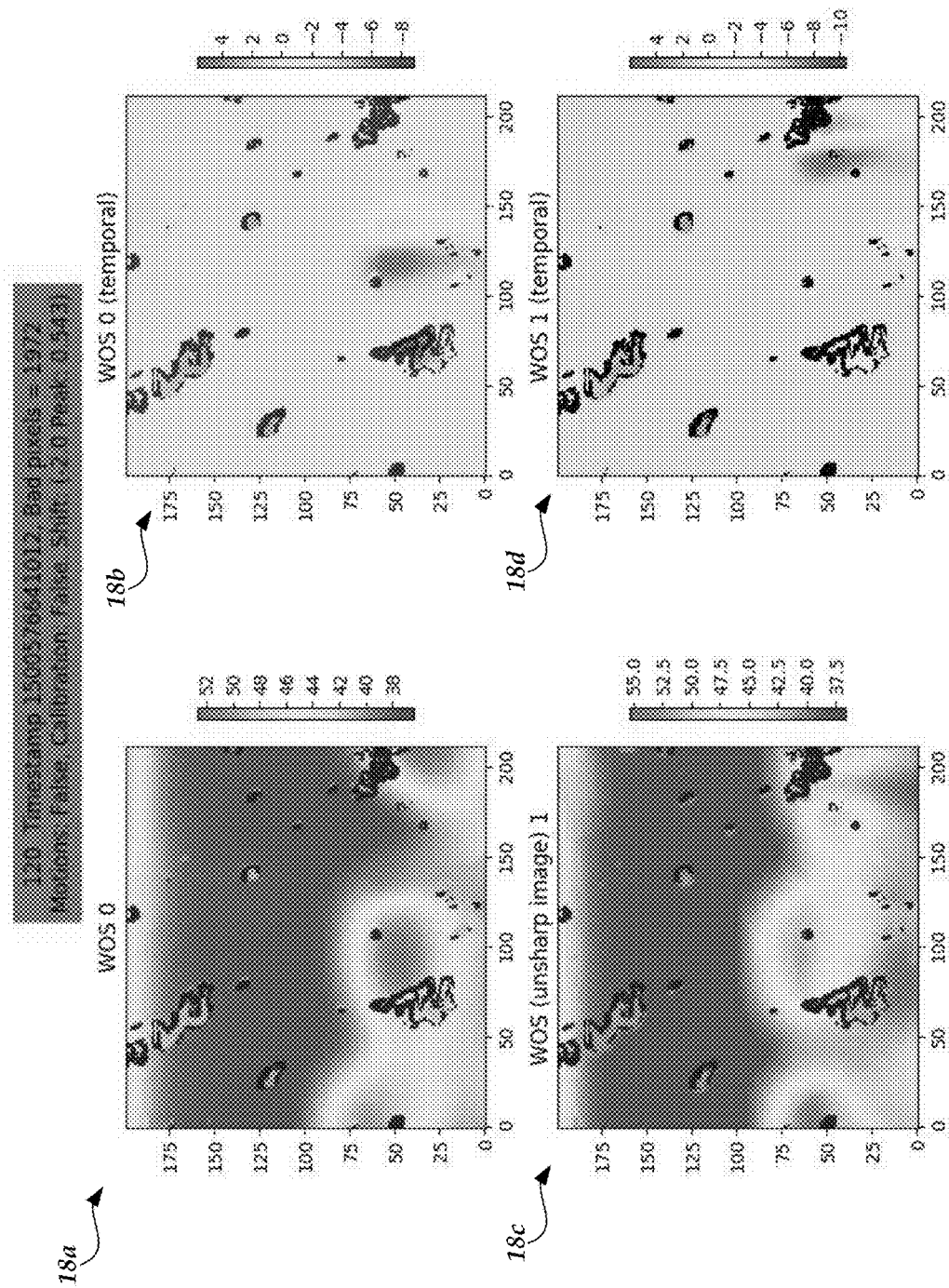
FIGS. 18A and 18B show an example of various stages of processing of data taken by window obscuration sensors with water drops sprinkled onto the optical window and a fishing lure approximately 50 cm away from the optical window.
Figure 18B:
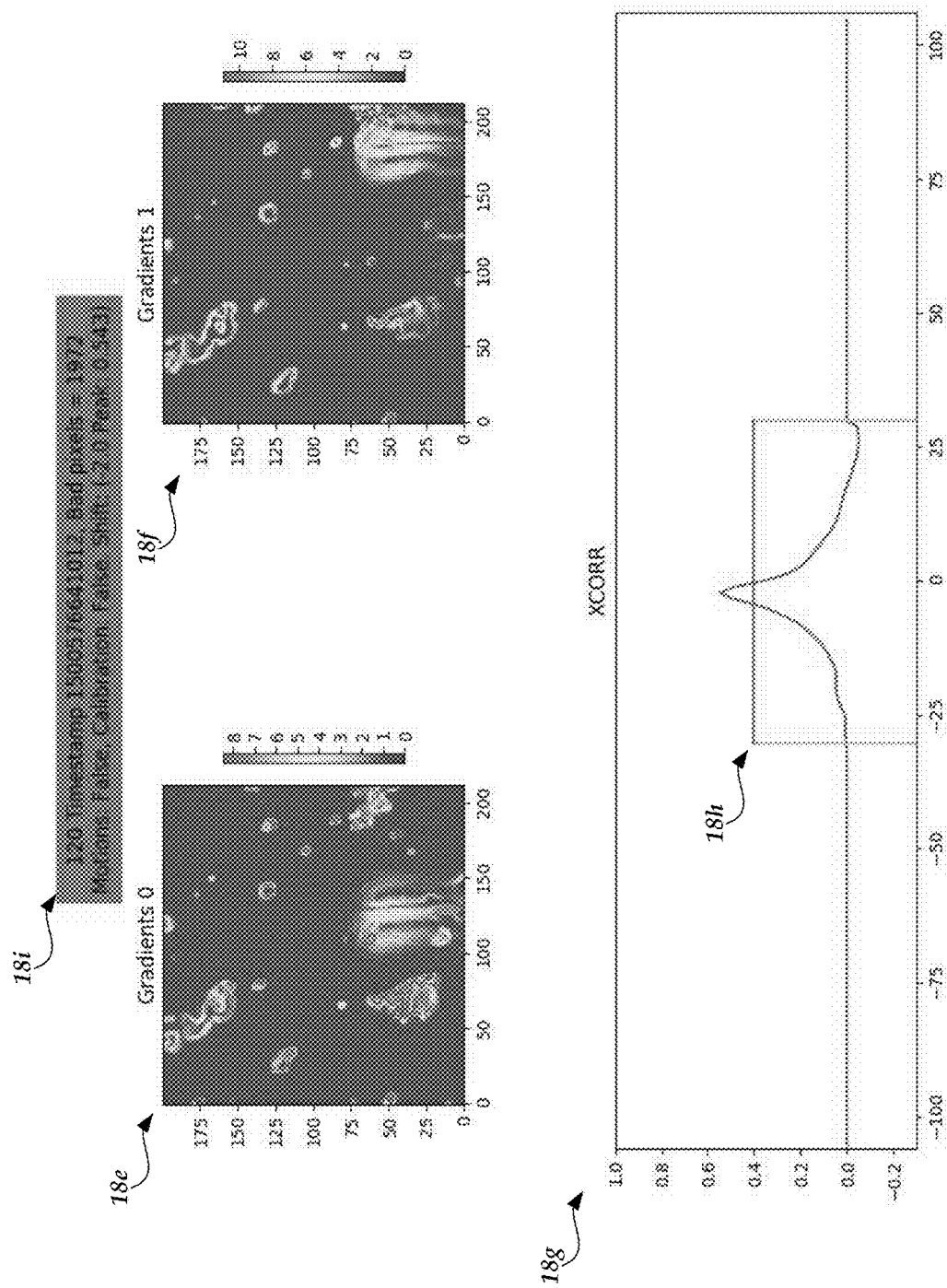

FIGS. 18A and 18B illustrate an example of the WOS alerting method 1002 of FIG. 10 in which water droplets are sprinkled onto the optical window 1506 and there is also a fishing lure moving across the scene at a distance of approximately 50 centimeters from the optical window. The example of FIGS. 18A and 18B illustrates how the WOS alert can be provided, even with a moving object potentially impacting the cross correlation calculations. For the sake of brevity, please refer to the discussions of FIGS. 16A and 16B for additional detail on the detection of water droplets on the optical window.

As shown in images 18*a* and 18*b*, the water droplets are clear and in focus, while the moving fishing lure is difficult to discern. Images 18*b* and 18*d* highlight the water droplets and the fishing lure. In particular, the fishing lure may be visible between columns 100 and 150 in image 18*b* and visible between columns 160 and 210 in image 18*b*. The sharp edges of the water droplets and the soft edges of the fishing lure are similarly visible in images 18*e* and 18*f*. Additionally, the cross-correlation values shown in graph 18*g* are relatively similar to those shown in graph 16*g* of FIG. 16B. As such, the WOS system has no trouble identifying the troublesome condition (water on the optical window), identifying a sufficient number of bad pixels (e.g., 1972 "bad pixels" as shown in banner 18*i*), and a sufficiently high cross-correlation value (e.g., a value of 0.543 at a shift of −2 pixels as illustrated in box 18*h* and banner 18*i*) and thereby deciding to issue a WOS alert (as shown in banner 18*i*), even in the presence of the moving fishing lure.

i. Water Droplets on the Optical Window with a Moving Tennis Racket at 1 Meter

Figure 19A:
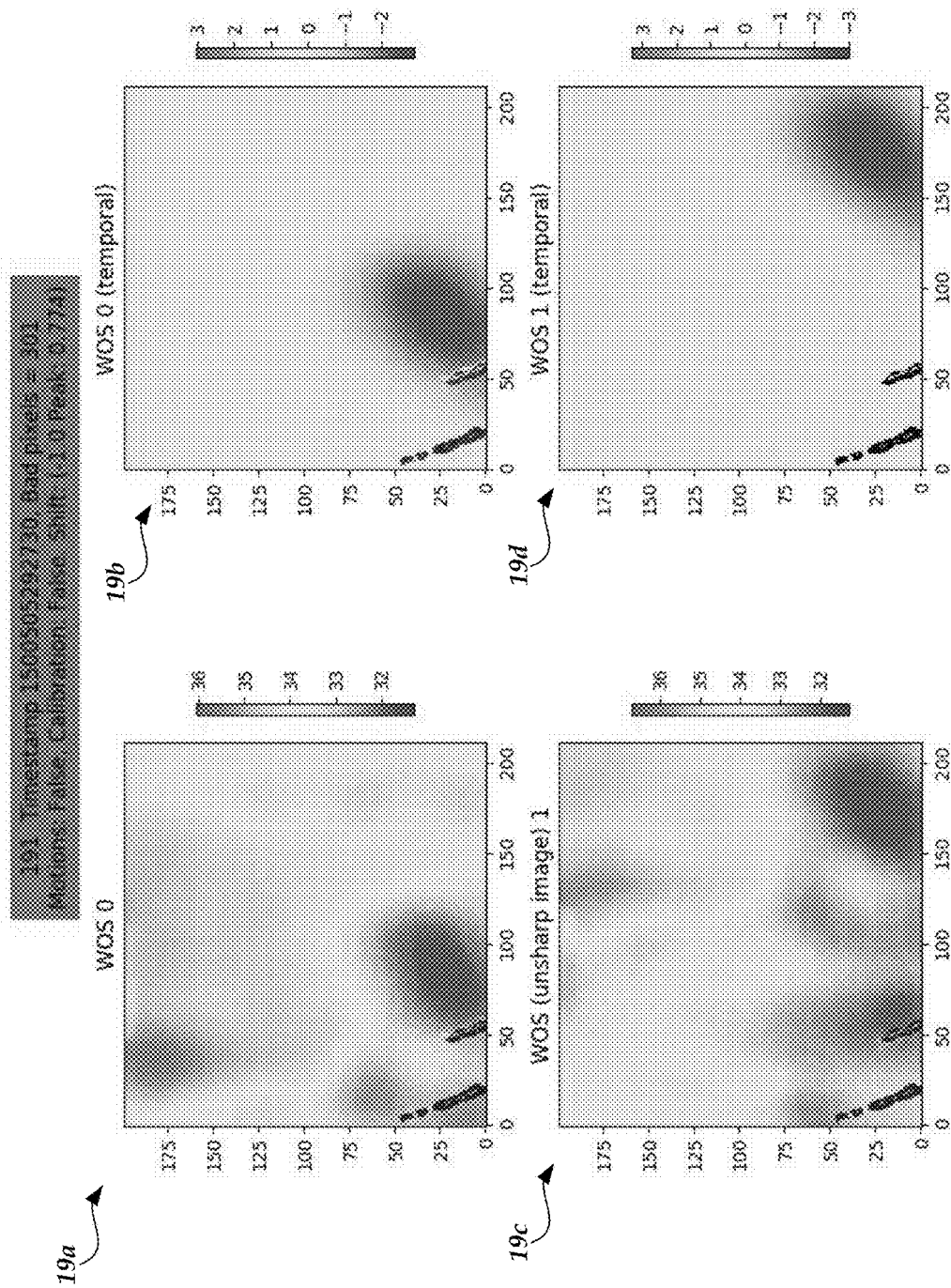
FIGS. 19A and 19B show an example of various stages of processing of data taken by window obscuration sensors with water drops sprinkled onto the optical window and with a moving tennis racket approximately 1 meter away from the optical window.
Figure 19B:
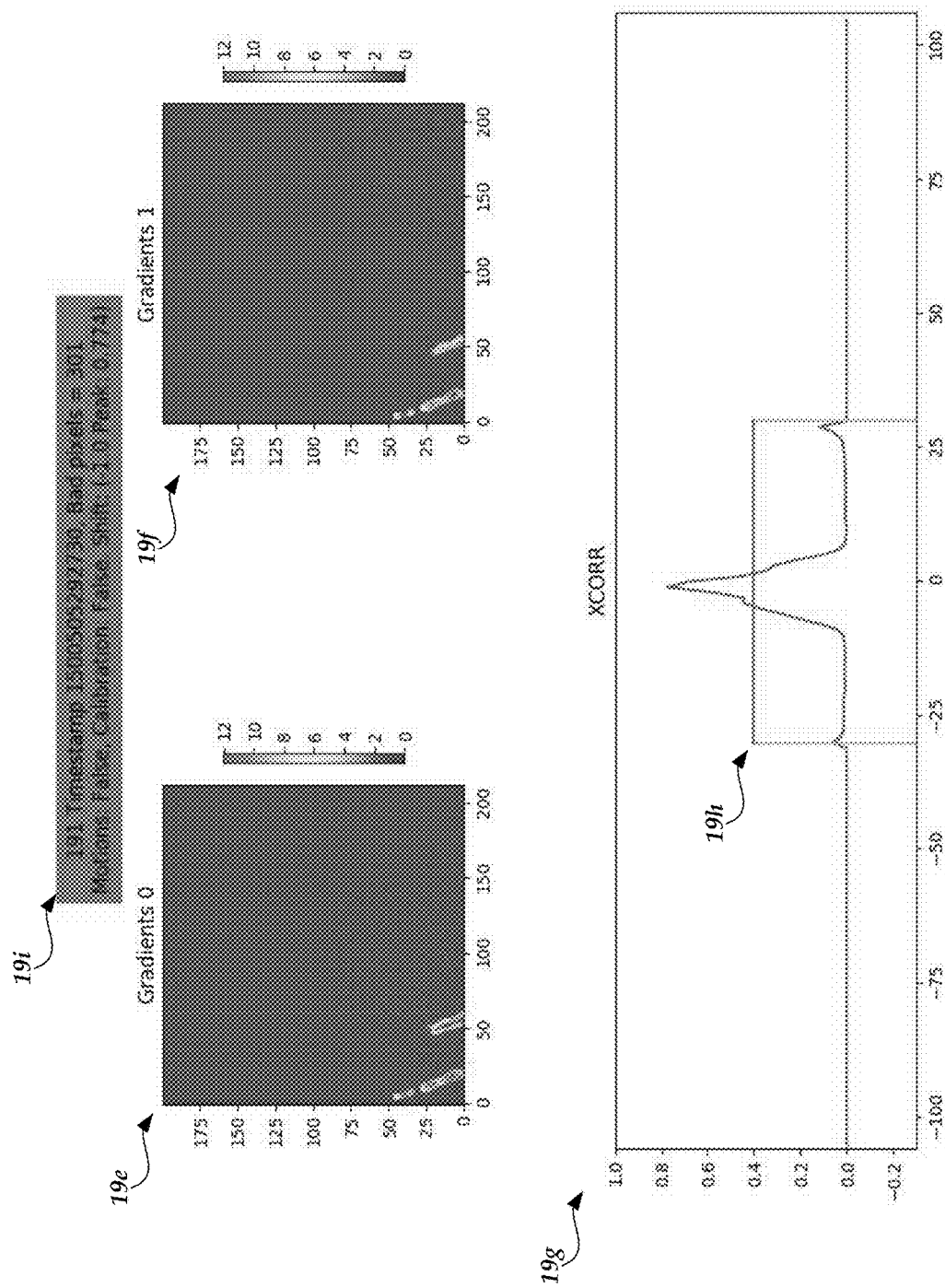

FIGS. 19A and 19B illustrate an example of the WOS alerting method 1002 of FIG. 10 in which water droplets are sprinkled onto the optical window 1506 and there is also a tennis racket moving across the scene at a distance of approximately 1 meter from the optical window. The example of FIGS. 19A and 19B illustrates how the WOS alert can be provided, even with a moving object potentially impacting the cross correlation calculations. For the sake of brevity, please refer to the discussions of FIGS. 16A and 16B for additional detail on the detection of water droplets on the optical window.

As shown in images 19a and 19b, the water droplets are clear and in focus, while the tennis racket is difficult to discern. Images 19b and 19d highlight the water droplets and the tennis racket. In particular, the tennis racket may be visible between columns 50 and 100 in image 19b and visible between columns 150 and 200 in image 19b. The sharp edges of the water droplets are similarly visible in images 19e and 19f, while the soft edges of the tennis racket at a distance of 1 meter may fall below the edge threshold and not appear in images 19e and 19f. Additionally, the cross-correlation values shown in graph 19g are relatively similar to those shown in graph 16g of FIG. 16B. As such, the WOS system has no trouble identifying the troublesome condition (water on the optical window), identifying a sufficient number of bad pixels (e.g., 301 "bad pixels"), and a sufficiently high cross-correlation value (e.g., a value of 0.774 at a shift of −1 pixels as shown in box 19h and banner 19i) and thereby deciding to issue a WOS alert (as shown in banner 19i), even in the presence of the moving tennis racket.

j. Water Droplets on the Optical Window with a Moving Object at 2 Meter

Figure 20A:
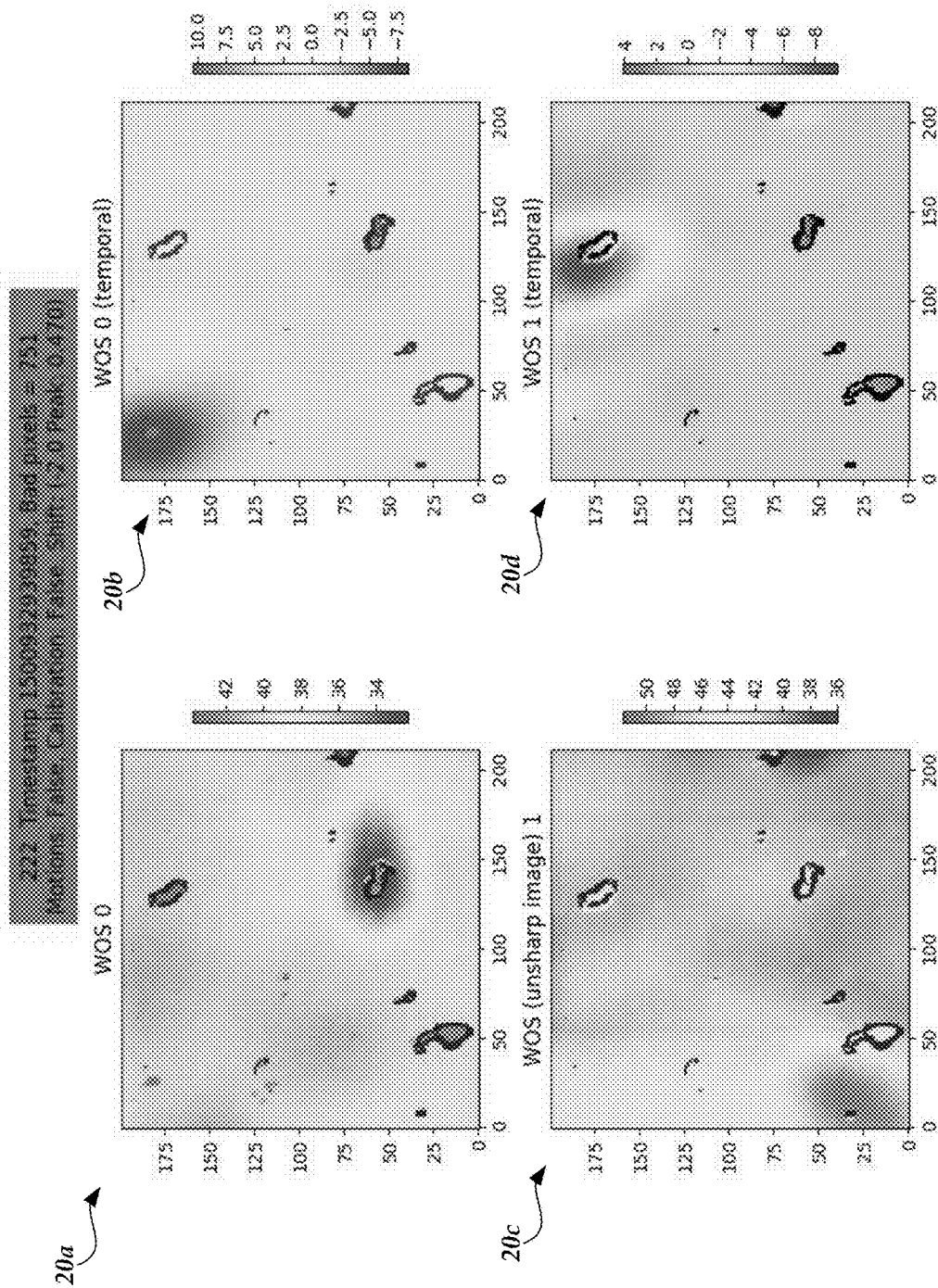
FIGS. 20A and 20B show an example of various stages of processing of data taken by window obscuration sensors with water drops sprinkled onto the optical window and with a moving object approximately 2 meters away from the optical window.
Figure 20B:
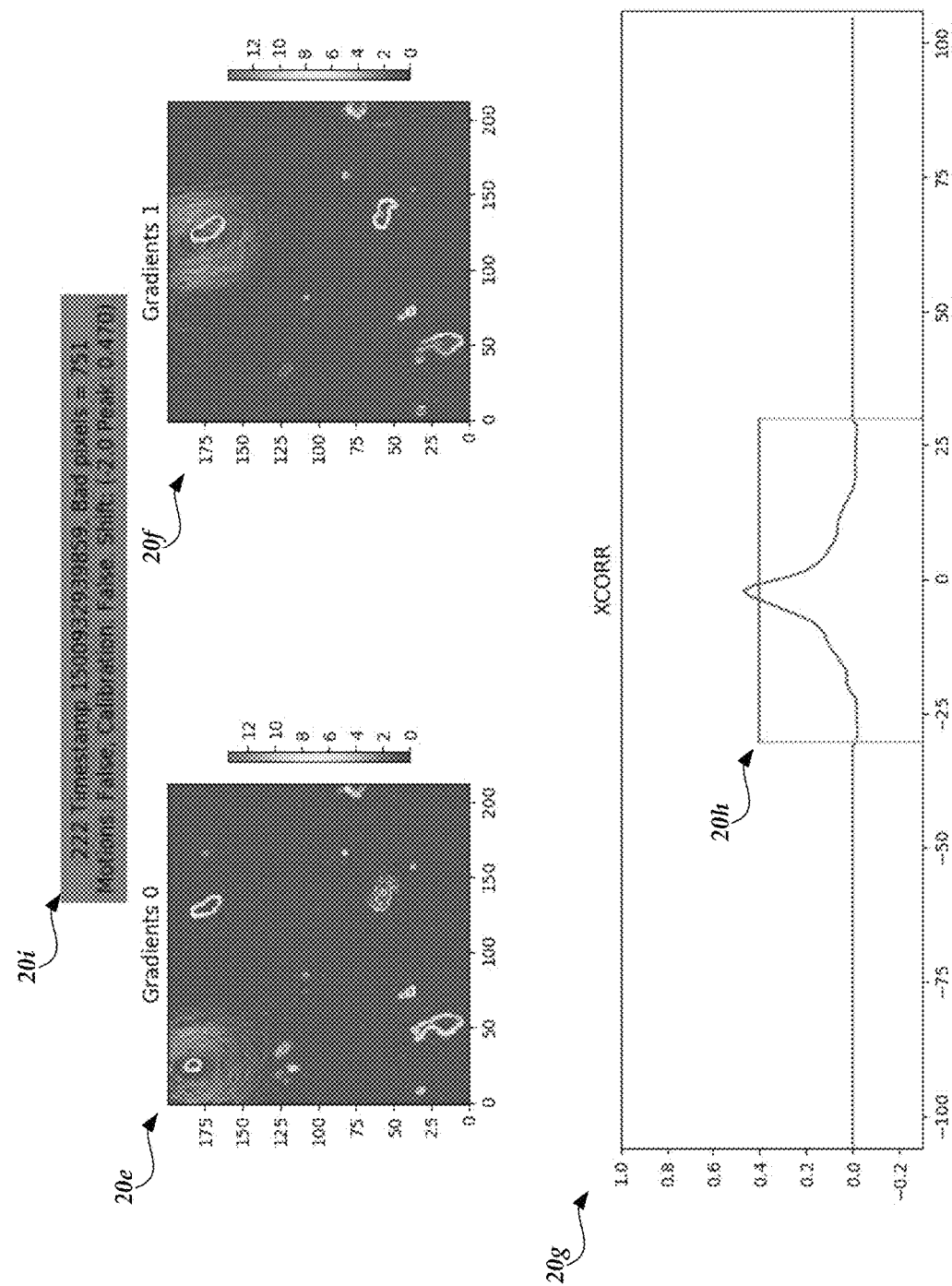

FIGS. 20A and 20B illustrate an example of the WOS alerting method 1002 of FIG. 10 in which water droplets are sprinkled onto the optical window 1506 and there is also an object across the scene at a distance of approximately 2 meters from the optical window. The example of FIGS. 20A and 20B illustrates how the WOS alert can be provided, even with a moving object potentially impacting the cross correlation calculations. For the sake of brevity, please refer to the discussions of FIGS. 16A and 16B for additional detail on the detection of water droplets on the optical window.

As shown in images 20a and 20b, the water droplets are clear and in focus, while the moving object is difficult to discern. Images 20b and 20d highlight the water droplets and illuminate the positions of the moving object (the dark spot in images 20b and 20d). The sharp edges of the water droplets are similarly visible in images 20e and 20f, while the soft edges of the object at a distance of 2 meter may fall mostly below the edge threshold and not appear in images 20e and 20f. Additionally, the cross-correlation values shown in graph 20g are relatively similar to those shown in graph 16g of FIG. 16B. As such, the WOS system has no trouble identifying the troublesome condition (water on the optical window), identifying a sufficient number of bad pixels (e.g., 751 "bad pixels"), and a sufficiently high cross-correlation value (e.g., a value of 0.470 at a pixel offset of −2 as shown in box 20h and banner 20i) and thereby deciding to issue a WOS alert (as shown in banner 20i), even in the presence of the moving object.

k. A Gas Release at 5 Centimeters

Figure 21A:
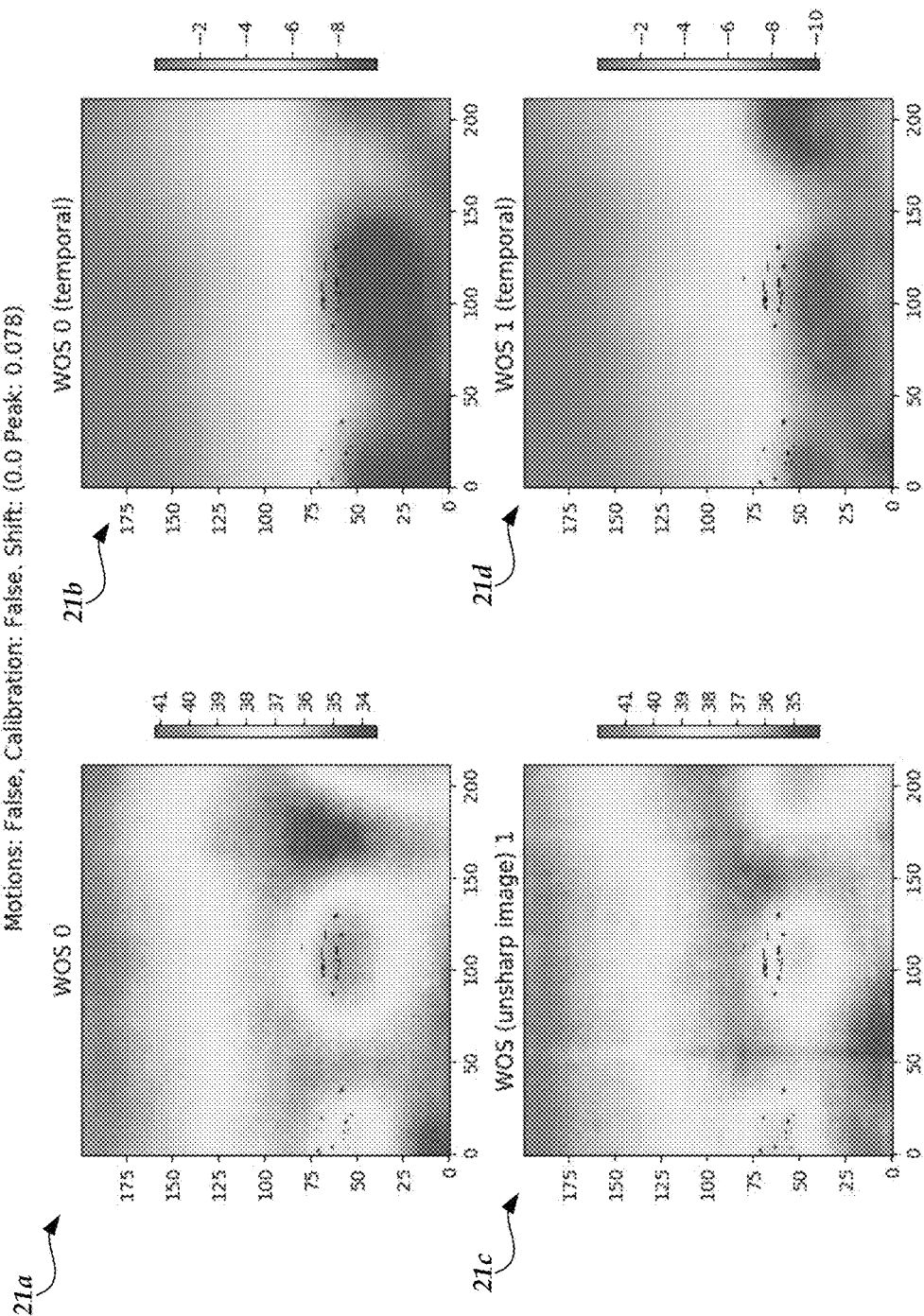
FIGS. 21A, 21B, and 21C show an example of various stages of processing of data taken by window obscuration sensors with a gas release at a distance of 5 cm away from the optical window.
Figure 21B:
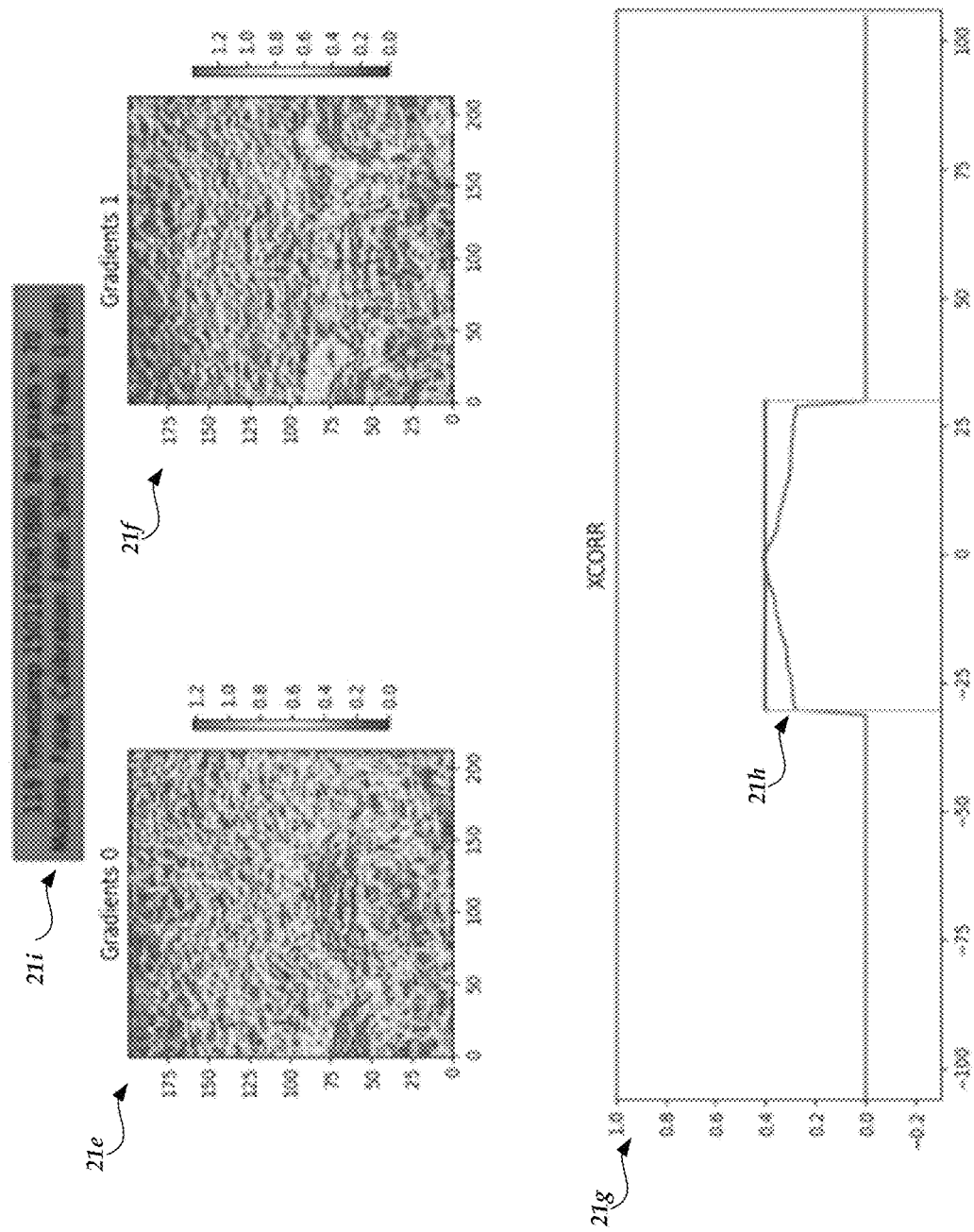
Figure 21C:
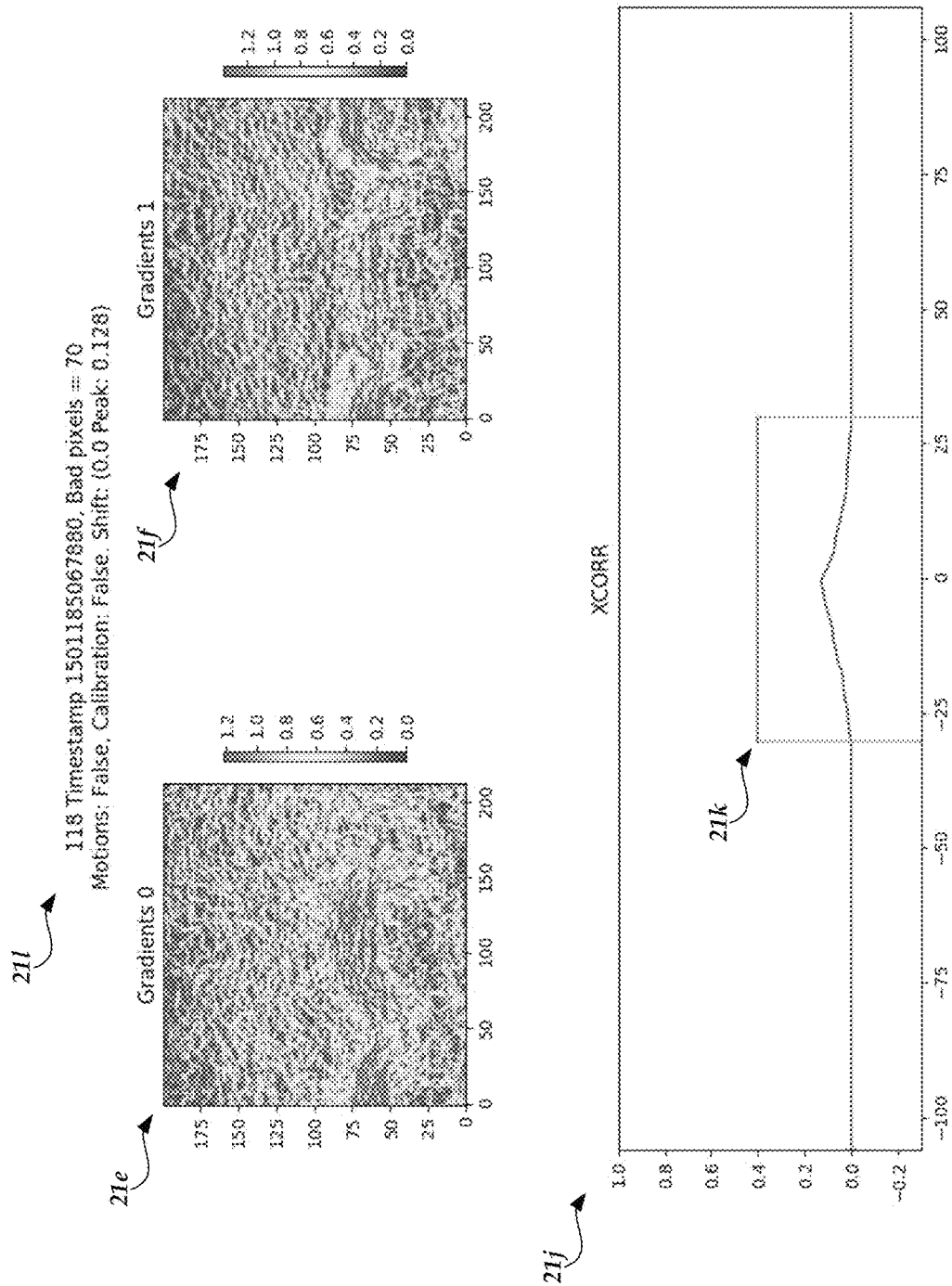

FIGS. 21A, 21B, and 21C illustrate a variation in which the object located in the near field region is actually a target species (e.g., a gas that the system 1000 is desired to detect). In particular, FIGS. 21A-21C illustrate an example of the WOS alerting method 1002 of FIG. 10 in which a gas (e.g., propane) is released in close proximity (e.g., at a 5 cm distance) of the optical window 1506 of one of the systems 1000. The gas release was configured to cover the full scene being imaged by the system.

Image 21a of FIG. 21A may be an image captured from a first WOS channel such as optical channel 6 of FIG. 8B and passed through an unsharp mask (such as in step 1006 of FIG. 10). In image 21a, the gas release is discernable as general variations across the image.

Image 21b may be a version of image 21a after applying an optional temporal mask (e.g., subtracting out of reference frame as in step 1008 of FIG. 10)). In image 21b, features that do not represent changes from a reference frame have been removed. Thus, in a fixed installation such as the illustrated example, background features and features associated with static objects are removed from image 21b. Generally, these features are not associated objects of interest to the WOS system (e.g., with objects in the near-field region). Image 21b does highlight the gas release, as subtracting the reference frame highlights that there are significant differences from the reference frame. However, the differences are relatively uniform across the scene, since the gas release covers the entire scene.

Image 21e of FIG. 21B may be a version of image 21b (or 21a if the temporal mask step is skipped) after applying an edge detection mask (e.g., after applying a Sobel filter as in step 1010 of FIG. 10. In image 21e, the soft features and edges of the background have been removed as the soft background features are not associated with objects of interest to the WOS system. In the present example, the gas release results in a proliferation of edges all across the scene as shown in images 21e and 21f.

Images 21c and 21d are equivalent versions of images 21a and 21b, respectively, but corresponding to a second WOS channel such as optical channel 7 of FIG. 8B. Similarly image 21f is an equivalent version of image 21e, but corresponding to the second WOS channel. Thus, images 21c, 21d, and 21f provide similar information, but with a beneficial parallax offset.

As shown in images 21e and 21f, a moderate number of pixels (e.g., 70 "bad pixels" as shown in banner 21i) have a gradient value above the predetermined threshold and the cross-correlation values may be relatively high (e.g., have values as high as 0.408 at a 0 pixel shift as shown in banner 21i). The number of such pixels and the cross-correlation values may be large enough to satisfy a WOS alert condition.

Graph 21g of FIG. 21B illustrates cross-correlation values for images 21e and 21f as a function of various horizontal offsets. As shown in graph 21g, the example with a gas release at 2 cm have a peak cross-correlation value just above the threshold illustrated by box 21h. Graph 21g specifically shows how the gas release causes significantly higher cross-correlation values across the entire range of pixel offsets. This result arises because the gas release causes absorption over the full image in a manner that is relatively independent of offset. As such, the WOS system described above would generally issue a WOS alert (as there is a sufficiently high cross correlation and a sufficient number of "bad" pixels).

However, it may be desirable not to issue a WOS alert for situations similar to the gas release example of FIGS. 21A-21B. As a result, the WOS system may be configured to subtract one of the smaller (e.g., a minimum) correlation value from the range of values inside box 21h from all of the correlation values inside box 21h. An example of an arrangement of this type is illustrated in FIG. 21C.

As shown in FIG. 21C, the cross-correlation values in graph 21j, after subtracting one of the lower values (e.g., the minimum value) within box 21h of FIG. 21B, are lower than the predetermined threshold (e.g., 0.4 as highlighted by box 21k). Thus, the WOS system may decide not to issue a WOS alert in such situations, as illustrated by banner 21l (which shows 70 "bad pixels" but a peak cross-correlation value of only 0.128 at a 0 pixel offset). In such situations, the systems 1000 may continue to search for target species, may recognize the spectral signature of the gas released in close proximity to the optical window, and may provide suitable alert to the user upon detection of the target species.

Thus, the modification of the WOS system described in connection with FIG. 21C (subtracting one of the lower cross-correlation values from all cross-correlation values) may beneficially enable to the WOS system not to trigger as WOS alarm merely by the presence of a target species in close proximity to the systems 1000. Instead, the system will only trigger WOS alarms when objects (which are not the desired target species) are near or on the optical window. It can generally be seen from FIGS. 11A-21C that subtracting the one of the lower cross-correlation values would not impair the ability of the WOS system to alert to the presence of water or other objects on or near the optical window, as the cross-correlation values for such conditions generally include at least one offset having a cross-correlation value near zero.

B. Additional Aspects and Variations of WOS Systems

1. Single-Channel Window Obscuration Sensors

In at least some designs, the systems 1000 disclosed herein can include a single channel window obscuration sensor, that detects objects on the optical window 1506 (FIG. 7). In particular, the WOS system may use image data from only a single optical channel such as optical channel 6 of FIG. 8B.

In such designs, the system may proceed under the method of FIG. 10, but may skip some of the steps. As an example, the system may skip the cross-correlation aspect of step 1012. In at least some designs, the WOS processing circuitry may apply an unsharp mask, a temporal difference mask (e.g., subtract out a reference image), and apply an edge detection process (e.g., apply a Sobel filter) to an image generated by a single channel WOS system. The processing circuitry may look at the number of "bad" pixels in the gradient image (e.g., the number of pixels in the gradient image showing sharp edges) to determine if there are objects on or near the optical window. In arrangements in which the single optical channel is focused on the optical window and region just in front of the optical window and more distant objects are blurry, these techniques may be sufficient to identify objects on or near the optical window with a single optical channel used in a WOS system.

2. Lens Aperture Sizing for Window Obscuration Sensors

In at least some designs, it may be beneficial to provide lenses, for any channel(s) used in a WOS system, having a suitable lens aperture sizing. As an example, it may be desirable for the lenses (from lens assembly 1502 of FIG. 9) for any channel(s) used in a WOS system have sufficiently large lens apertures (e.g., that the lenses are sufficiently fast with a sufficiently low f number) so as to ensure that objects outside of the immediate proximity (e.g., further than perhaps 20 cm, 50 cm, or 1 meter) are not also in focus for the WOS system's optical channel(s). If the WOS system were provided with lens apertures that were too small (e.g., had high f numbers), the depth of field of the lenses may extend undesirably far from the imaging system. As a result, the WOS system may be undesirably sensitive to distant objects. Since the WOS system is generally used in detecting nearby objects that may interfere with proper detection of target species, it is generally desirable to have the WOS system ignore distant objects.

In some designs, it may be desirable to provide a lens, for each WOS channel, having an f number between 3.0 and 1.0, between 2.0 and 1.0, between 1.375 and 1.0, between 1.0 and 0.875, between 1.0 and 0.7 or any combination of these ranges. The f number can be any value in any range defined by any of these values.

In at least some arrangements, dual-channel WOS systems may be less sensitive to the size of the lens apertures in the WOS system. In particular, dual-channel WOS systems may be able to utilize parallax effects to exclude distant objects, even if those objects are in focus due to a higher f number lens and an associated larger depth of field.

VI. Additional Examples

Various examples of imaging systems comprising an optical window and with capabilities to determine if the optical window is obscured (e.g., to detect objects on or in front of the window that may introduce obscuration that may degrade operation of the system) are described herein such as the additional examples enumerated below:

Additional Example 1

An Additional Example of an infrared (IR) imaging system comprising:
a housing;
an optical window disposed on the housing;
an optical detector system disposed within the housing; and
a plurality of spatially and spectrally distinct optical channels that transfer incident IR radiation from the optical window to the optical detector system, wherein a first optical channel out of the plurality of optical channels has a focus distance that is closer to the optical window than at least some of the other optical channels of the plurality of optical channels to detect obscuration that may degrade operation of the system.

Additional Example 2

The IR imaging system of Additional Example 1, wherein the first optical channel out of the plurality of optical channels has a focus less than 2 meters and other optical channels of the plurality of optical channels have a focus of greater than 10 meters.

Additional Example 3

The IR imaging system of any one of Additional Examples 1 to 2, wherein the first optical channel out of the plurality of optical channels has a focus less than 2 meters and other optical channels of the plurality of optical channels have a focus of greater than 20 meters.

Additional Example 4

The IR imaging system of any one of Additional Examples 1 to 3, wherein the first optical channel out of the plurality of optical channels has a focus less than 2 meters and other optical channels of the plurality of optical channels have a focus of greater than 30 meters.

Additional Example 5

The IR imaging system of any one of Additional Examples 1 to 4, wherein the first optical channel out of the plurality of optical channels has a focus of 1 meter or less and other optical channels of the plurality of optical channels have a focus of greater than 10 meters.

Additional Example 6

The IR imaging system of any one of Additional Examples 1 to 5, wherein the first optical channel out of the plurality of optical channels has a focus of 1 meter or less and other optical channels of the plurality of optical channels have a focus of greater than 20 meters.

Additional Example 7

The IR imaging system of any one of Additional Examples 1 to 6, wherein the first optical channel out of the plurality of optical channels has a focus of 1 meter or less and other optical channels of the plurality of optical channels have a focus of greater than 30 meters.

Additional Example 8

The IR imaging system of any one of Additional Examples 1 to 7, wherein at least some of the other optical channels of the plurality of optical channels have focus distances at least 5 meters greater than the focus distance of the first optical channel.

Additional Example 9

The IR imaging system of any one of Additional Examples 1 to 8, wherein at least some of the other optical channels of the plurality of optical channels have focus distances at least 10 meters greater than the focus distance of the first optical channel.

Additional Example 10

The IR imaging system of any one of Additional Examples 1 to 9, wherein at least some of the other optical channels of the plurality of optical channels have focus distances at least 20 meters greater than the focus distance of the first optical channel.

Additional Example 11

The IR imaging system of any one of Additional Examples 1 to 10, wherein the first optical channel out of the plurality of optical channels has a focus distance of 1 meter or less.

Additional Example 12

The IR imaging system of any one of Additional Examples 1 to 11, wherein the first optical channel out of the plurality of optical channels has a focus distance of 2 meter or less.

Additional Example 13

The IR imaging system of any one of Additional Examples 1 to 12, wherein the first optical channel and the other optical channels include imaging lenses for imaging objects onto the optical detector system, said imaging lenses having focal lengths.

Additional Example 14

The IR imaging system of any one of Additional Examples 1 to 13, wherein the focal lengths for lenses in the other optical channels exceed the focal length for the first optical channel.

Additional Example 15

The IR imaging system of any one of Additional Examples 1 to 14, wherein the focal lengths for lenses in the other optical channels exceed the focal length for the first optical channel by at least 2×.

Additional Example 16

The IR imaging system of any one of Additional Examples 1 to 15, wherein the focal lengths for lenses in the other optical channels exceed the focal length for the first optical channel by at least 5×.

Additional Example 17

The IR imaging system of any one of Additional Examples 1 to 16, wherein the first optical channel is in focus at the optical window to detect obscuration that may degrade operation of the system.

Additional Example 18

The IR imaging system of any one of Additional Examples 1 to 17, wherein the first optical channel has a depth of field over which the optical channel is substantially in focus and wherein the depth of field of the first optical channel extends between a depth of the optical window and approximately 1 meter beyond the optical window.

Additional Example 19

The IR imaging system of any one of Additional Examples 1 to 18, wherein the first optical channel has a depth of field over which the optical channel is substantially in focus and wherein the depth of field of the first optical channel extends between a depth of the optical window and approximately 50 cm beyond the optical window.

Additional Example 20

The IR imaging system of any one of Additional Examples 1 to 19, wherein the first optical channel has a depth of field over which the optical channel is substantially in focus and wherein the depth of field of the first optical channel extends between a depth of the optical window and approximately 20 cm beyond the optical window.

Additional Example 21

The IR imaging system of any one of Additional Examples 1 to 20, wherein the first optical channel has a depth of field over which the optical channel is substantially in focus and wherein the depth of field of the first optical channel extends between a depth of the optical window and approximately 10 cm beyond the optical window.

Additional Example 22

The IR imaging system of any one of Additional Examples 1 to 21, further comprising:
a processing unit comprising processing electronics configured to process image data from the first optical channel to detect obscuration that may degrade operation of the system.

Additional Example 23

The IR imaging system of any one of Additional Examples 1 to 22, wherein the processing unit is configured to evaluate how much of the image data is in focus to detect obscuration that may degrade operation of the system.

Additional Example 24

The IR imaging system of any one of Additional Examples 1 to 23, wherein the processing unit is configured to evaluate the contrast of the image data to detect obscuration that may degrade operation of the system.

Additional Example 25

The IR imaging system of any one of Additional Examples 1 to 24, wherein the processing unit is configured to perform edge enhancement of the image data.

Additional Example 26

The IR imaging system of any one of Additional Examples 1 to 25, wherein the processing unit is configured to perform edge detection of the image data.

Additional Example 27

The IR imaging system of any one of Additional Examples 1 to 26, wherein the processing unit is configured to perform normalization of the image data.

Additional Example 28

The IR imaging system of any one of Additional Examples 1 to 27, wherein the normalization of the image data comprises scaling the image data.

Additional Example 29

The IR imaging system of any one of Additional Examples 1 to 28, wherein the normalization of the image data comprises subtracting from the image data.

Additional Example 30

The IR imaging system of any one of Additional Examples 1 to 29, wherein the processing unit is configured to evaluate whether image data exceeds a threshold to determine whether obscuration is present that may degrade operation of the system.

Additional Example 31

The IR imaging system of any one of Additional Examples 1 to 30, wherein a second optical channel out of the plurality of optical channels has a focus distance that is closer to the optical window than at least some of the other optical channels of the plurality of optical channels to detect obscuration that may degrade operation of the system.

Additional Example 32

The IR imaging system of Additional Example 31, wherein the second optical channel out of the plurality of optical channels has a focus less than 2 meters and other optical channels of the plurality of optical channels have a focus of greater than 10 meters.

Additional Example 33

The IR imaging system of any one of Additional Examples 1 to 32, wherein the second optical channel out of the plurality of optical channels has a focus less than 2 meters and other optical channels of the plurality of optical channels have a focus of greater than 20 meters.

Additional Example 34

The IR imaging system of any one of Additional Examples 1 to 33, wherein the second optical channel out of the plurality of optical channels has a focus less than 2 meters and other optical channels of the plurality of optical channels have a focus of greater than 30 meters.

Additional Example 35

The IR imaging system of any one of Additional Examples 1 to 34, wherein the second optical channel out of the plurality of optical channels has a focus of 1 meter or less and other optical channels of the plurality of optical channels have a focus of greater than 10 meters.

Additional Example 36

The IR imaging system of any one of Additional Examples 1 to 35, wherein the second optical channel out of the plurality of optical channels has a focus of 1 meter or less and other optical channels of the plurality of optical channels have a focus of greater than 20 meters.

Additional Example 37

The IR imaging system of any one of Additional Examples 1 to 36, wherein the second optical channel out of the plurality of optical channels has a focus of 1 meter or less and other optical channels of the plurality of optical channels have a focus of greater than 30 meters.

Additional Example 38

The IR imaging system of any one of Additional Examples 1 to 37, wherein at least some of the other optical channels of the plurality of optical channels have focus distances at least 5 meters greater than the focus distance of the second optical channel.

Additional Example 39

The IR imaging system of any one of Additional Examples 1 to 38, wherein at least some of the other optical channels of the plurality of optical channels have focus distances at least 10 meters greater than the focus distance of the second optical channel.

Additional Example 40

The IR imaging system of any one of Additional Examples 1 to 39, wherein at least some of the other optical channels of the plurality of optical channels have focus distances at least 20 meters greater than the focus distance of the second optical channel.

Additional Example 41

The IR imaging system of any one of Additional Examples 1 to 40, wherein the second optical channel out of the plurality of optical channels has a focus distance of 1 meter or less.

Additional Example 42

The IR imaging system of any one of Additional Examples 1 to 41, wherein the second optical channel out of the plurality of optical channels has a focus distance of 2 meter or less.

Additional Example 43

The IR imaging system of any one of Additional Examples 1 to 42, wherein the second optical channel and the other optical channels include imaging lenses for imaging objects onto the optical detector system, said imaging lenses having focal lengths.

Additional Example 44

The IR imaging system of any one of Additional Examples 1 to 43, wherein the focal lengths for lenses in the other optical channels exceed the focal length for the second optical channel.

Additional Example 45

The IR imaging system of any one of Additional Examples 1 to 44, wherein the focal lengths for lenses in the other optical channels exceed the focal length for the second optical channel by at least 2×.

Additional Example 46

The IR imaging system of any one of Additional Examples 1 to 45, wherein the focal lengths for lenses in the other optical channels exceed the focal length for the second optical channel by at least 5×.

Additional Example 47

The IR imaging system of any one of Additional Examples 1 to 46, wherein a second optical channel out of the plurality of optical channels is in focus at the optical window to detect obscuration that may degrade operation of the system.

Additional Example 48

The IR imaging system of any one of Additional Examples 1 to 47, wherein the second optical channel has a depth of field over which the optical channel is substantially in focus and wherein the depth of field of the second optical channel extends between a depth of the optical window and approximately 1 meter beyond the optical window.

Additional Example 49

The IR imaging system of any one of Additional Examples 1 to 48, wherein the second optical channel has a depth of field over which the optical channel is substantially in focus and wherein the depth of field of the second optical channel extends between a depth of the optical window and approximately 50 cm beyond the optical window.

Additional Example 50

The IR imaging system of any one of Additional Examples 1 to 49, wherein the second optical channel has a depth of field over which the optical channel is substantially in focus and wherein the depth of field of the second optical channel extends between a depth of the optical window and approximately 20 cm beyond the optical window.

Additional Example 51

The IR imaging system of any one of Additional Examples 1 to 50, wherein the second optical channel has a depth of field over which the optical channel is substantially in focus and wherein the depth of field of the second optical channel extends between a depth of the optical window and approximately 10 cm beyond the optical window.

Additional Example 52

The IR imaging system of any one of Additional Examples 1 to 51, wherein the processing unit is configured to process image data from the second optical channel to detect obscuration that may degrade operation of the system.

Additional Example 53

The IR imaging system of any one of Additional Examples 1 to 52, wherein the processing unit is configured to evaluate how much of the image data from the second optical channel is in focus to detect obscuration that may degrade operation of the system.

Additional Example 54

The IR imaging system of any one of Additional Examples 1 to 53, wherein the processing unit is configured to evaluate the contrast of the image data from the second optical channel to detect obscuration that may degrade operation of the system.

Additional Example 55

The IR imaging system of any one of Additional Examples 1 to 54, wherein the processing unit is configured to perform edge enhancement of the image data from the second optical channel.

Additional Example 56

The IR imaging system of any one of Additional Examples 1 to 55, wherein the processing unit is configured to perform edge detection of the image data from the second optical channel.

Additional Example 57

The IR imaging system of any one of Additional Examples 1 to 56, wherein the processing unit is configured to perform normalization of the image data from the second optical channel.

Additional Example 58

The IR imaging system of any one of Additional Examples 1 to 57, wherein the normalization of the image data comprises scaling the image data from the second optical channel.

Additional Example 59

The IR imaging system of any one of Additional Examples 1 to 58, wherein the normalization of the image data comprises subtracting from the image data from the second optical channel.

Additional Example 60

The IR imaging system of any one of Additional Examples 1 to 59, wherein the processing unit is configured to evaluate whether image data from the second optical channel exceeds a threshold to determine whether obscuration is present that may degrade operation of the system.

Additional Example 61

The IR imaging system of any one of Additional Examples 1 to 60, wherein a plurality of the optical channels are in focus at optical infinity to detect a target species.

Additional Example 62

The IR imaging system of any one of Additional Examples 1 to 61, wherein a plurality of the optical channels are in focus at a distance of at least 10 meters to detect a target species.

Additional Example 63

The IR imaging system of any one of Additional Examples 1 to 62, wherein a plurality of the optical channels are in focus at a distance of at least 20 meters to detect a target species.

Additional Example 64

The IR imaging system of any one of Additional Examples 1 to 63, wherein the processing unit is further configured to process image data from the plurality of optical channels to detect the target species.

Additional Example 65

The IR imaging system of any one of Additional Examples 1 to 64, wherein the optical detector system comprises a plurality of optical detectors, each of which is associated with a respective one of the optical channels.

Additional Example 66

The IR imaging system of any one of Additional Examples 1 to 65, wherein the optical detector system comprises at least one optical detector having a plurality of regions, each of the regions being associated with a respective one of the optical channels.

Additional Example 67

The IR imaging system of any one of Additional Examples 1 to 66, wherein:
a second optical channel out of the plurality of optical channels is in focus at the optical window; and
the processing unit is configured to process image data from the first and second optical channels to detect obscuration that may degrade operation of the system.

Additional Example 68

The IR imaging system of any one of Additional Examples 1 to 67, wherein the processing unit is configured to:
compare image data from the first and second optical channels to detect obscuration that may degrade operation of the system.

Additional Example 69

The IR imaging system of any one of Additional Examples 1 to 68, wherein comparing the first and second images comprises comparing the first and second images and using differences between the first and second images caused by parallax to determine whether obscuration is present that may degrade operation of the system.

Additional Example 70

The IR imaging system of any one of Additional Examples 1 to 69, wherein comparing the first and second images comprises performing a correlation of the first and second images.

Additional Example 71

The IR imaging system of any one of Additional Examples 1 to 70, wherein the first and second optical channels are spatially distinct in a given direction and wherein processing unit is configured to:
comparing image data from the first and second optical channels at a plurality of offsets along the given direction to detect obscuration that may degrade operation of the system.

Additional Example 72

The IR imaging system of any one of Additional Examples 1 to 71, wherein the processing unit is configured to enhance edges in the image data from the two optical channels.

Additional Example 73

The IR imaging system of any one of Additional Examples 1 to 72, wherein the processing unit is configured to apply an unsharp mask to the image data from the two optical channels.

Additional Example 74

The IR imaging system of any one of Additional Examples 1 to 73, wherein the processing unit is configured to subtract at least one reference image from the image data from the two optical channels.

Additional Example 75

The IR imaging system of any one of Additional Examples 1 to 74, wherein the processing unit is configured to detect edges in the image data from the two optical channels.

Additional Example 76

The IR imaging system of any one of Additional Examples 1 to 75, wherein the processing unit is configured to apply an edge detection mask to the image data from the two optical channels.

Additional Example 77

The IR imaging system of any one of Additional Examples 1 to 76, wherein the processing unit is configured to apply a Sobel filter to the image data from the two optical channels.

Additional Example 78

The IR imaging system of any one of Additional Examples 1 to 77, wherein the processing unit is configured to apply a Sobel filter to the image data from the two optical channels to create first and second gradient images.

Additional Example 79

The IR imaging system of any one of Additional Examples 1 to 78, wherein the processing unit is configured to normalize the first and second gradient images.

Additional Example 80

The IR imaging system of any one of Additional Examples 1 to 79, wherein the processing unit is configured to cross-correlate the first and second gradient images to detect obscuration that may degrade operation of the system.

Additional Example 81

The IR imaging system of any one of Additional Examples 1 to 80, wherein the window is embedded in the housing or is in an opening in the housing.

Additional Example 82

The IR imaging system of any one of Additional Examples 1 to 81, wherein the IR imaging system is configured to compensate for effects of attenuation due to obscuration.

Additional Example 83

The IR imaging system of any one of Additional Examples 1 to 82, wherein said IR imaging system is configured such that operation of the system includes performing spectral analysis on images to detect target species and wherein said IR imaging system is configured to compensate for effects of attenuation due to obscuration on said spectral analysis.

Additional Example 84

The IR imaging system of any one of Additional Examples 1 to 83, wherein said IR imaging system is configured such that operation of the system includes performing spectral analysis on images to detect target species and wherein said IR imaging system is configured to deemphasize one or more frames of infrared image data from the other optical channels of the plurality of optical channels in the determination of the presence of a target species.

Additional Example 85

An Additional Example of an infrared (IR) imaging system for imaging a target species in a scene, the IR imaging system comprising:
  an optical window;
  a first camera system configured to acquire infrared image data of the scene through the optical window;
  a second camera system focused closer to the optical window than the first camera system; and
  a processing unit containing a processor configured to:
    analyze the infrared image data from the first camera system to detect the target species based on the infrared image data; and
    analyze image data from the second camera system to determine whether obscuration is present that may degrade operation of the system based on the image data from the second camera system.

Additional Example 86

The IR imaging system of Additional Example 85, wherein the first and second camera system comprise first and second optical channels that are spatially and spectrally distinct.

Additional Example 87

The IR imaging system of any one of Additional Examples 85 to 86, wherein said processing unit is configured to provide a window obscuration alert after determining that obscuration is present that may degrade operation of the system.

Additional Example 88

The IR imaging system of any one of Additional Examples 85 to 87, wherein the processing unit is configured to receive the window obscuration alert and, in response, to adjust the infrared image data from the first camera system in compensation for the obscuration.

Additional Example 89

The IR imaging system of any one of Additional Examples 85 to 88, wherein the processing unit is configured to receive the window obscuration alert and, in response, to disable analysis of the infrared image data from the first camera system.

Additional Example 90

The IR imaging system of any one of Additional Examples 85 to 89, wherein the processing unit is configured to receive the window obscuration alert and, in response, deemphasize one or more frames of infrared image data from the first camera system in the determination of the presence of a target species.

Additional Example 91

The IR imaging system of any one of Additional Examples 85 to 90, wherein the IR imaging system is configured to compensate for effects of attenuation due to obscuration.

Additional Example 92

The IR imaging system of any one of Additional Examples 85 to 91, wherein said IR imaging system is configured to perform spectral analysis on images to detect target species and is configured to compensate for effects of attenuation due to the obscuration on said spectral analysis.

Additional Example 93

The IR imaging system of any one of Additional Examples 85 to 92, wherein the processing unit is configured to provide the window obscuration alert to a user.

Additional Example 94

The IR imaging system of any one of Additional Examples 85 to 93, wherein the IR imaging system further comprises:
  an optical focal plane array (FPA) divided into portions; and
  a plurality of lens assemblies, each lens assembly configured to focus light from the scene onto a different one of the portions of the FPA.

Additional Example 95

The IR imaging system of any one of Additional Examples 85 to 94, wherein:
  the first camera system is formed from a plurality of the lens assemblies and a plurality of the portions of the FPA; and
  the second camera system is formed from one of the lens assemblies and one of the portions of the FPA.

Additional Example 96

The IR imaging system of any one of Additional Examples 85 to 95, wherein:
  the first camera system is formed from a plurality of the lens assemblies and a plurality of the portions of the FPA; and
  the second camera system is formed from two of the lens assemblies and two of the portions of the FPA.

Additional Example 97

The IR imaging system of any one of Additional Examples 85 to 96, wherein:
  the first camera system is formed from a plurality of the lens assemblies and a plurality of the portions of the FPA; and
  the second camera system is formed from two of the lens assemblies and two of the portions of the FPA, wherein the two lens assemblies and the two portions of the FPA that form the second camera system comprise adjacent lens assemblies and adjacent portions of the FPA.

Additional Example 98

The IR imaging system of any one of Additional Examples 85 to 97, wherein the IR imaging system further comprises:
  a plurality of optical focal plane arrays (FPA); and
  a plurality of lenses, different lenses configured to focus light from the scene onto a different ones of FPAs.

Additional Example 99

The IR imaging system of any one of Additional Examples 85 to 98, wherein the IR imaging system further comprises:
  a plurality of optical focal plane arrays (FPA); and
  a plurality of lens assemblies, different lens assemblies configured to focus light from the scene onto a different ones of FPAs.

Additional Example 100

The IR imaging system of any one of Additional Examples 85 to 99, wherein the processing unit is configured to evaluate how much of the image data is in focus to detect obscuration that may degrade operation of the system.

Additional Example 101

The IR imaging system of any one of Additional Examples 85 to 100, wherein the processing unit is configured to evaluate the contrast of the image data to detect obscuration that may degrade operation of the system.

Additional Example 102

The IR imaging system of any one of Additional Examples 85 to 101, wherein the processing unit is configured to perform edge enhancement of the image data.

Additional Example 103

The IR imaging system of any one of Additional Examples 85 to 102, wherein the processing unit is configured to perform edge detection of the image data.

Additional Example 104

The IR imaging system of any one of Additional Examples 85 to 103, wherein the processing unit is configured to perform normalization of the image data.

Additional Example 105

The IR imaging system of any one of Additional Examples 85 to 104, wherein the normalization of the image data comprises scaling the image data.

Additional Example 106

The IR imaging system of any one of Additional Examples 85 to 105, wherein the normalization of the image data comprises subtracting from the image data.

Additional Example 107

The IR imaging system of any one of Additional Examples 85 to 106, wherein the processing unit is configured to evaluate whether image data exceeds a threshold to determine whether obscuration is present that may degrade operation of the system.

Additional Example 108

The IR imaging system of any one of Additional Examples 85 to 107, wherein analyzing image data from the second camera system comprises:

analyzing image data from first and second optical channels of the second camera system to detect obscuration that may degrade operation of the system.

Additional Example 109

The IR imaging system of any one of Additional Examples 85 to 108, wherein the processing unit is configured to:
compare image data from the first and second optical channels to detect obscuration that may degrade operation of the system.

Additional Example 110

The IR imaging system of any one of Additional Examples 85 to 109, wherein comparing the first and second images comprises comparing the first and second images and using differences between the first and second images caused by parallax to determine whether obscuration is present that may degrade operation of the system.

Additional Example 111

The IR imaging system of any one of Additional Examples 85 to 110, wherein comparing the first and second images comprises performing a correlation of the first and second images.

Additional Example 112

The IR imaging system of any one of Additional Examples 85 to 111, wherein the first and second optical channels are spatially distinct in a given direction and wherein processing unit is configured to:
compare image data from the first and second optical channels at a plurality of offsets along the given direction to detect obscuration that may degrade operation of the system.

Additional Example 113

The IR imaging system of any one of Additional Examples 85 to 112, wherein the processing unit is configured to enhance edges in the image data from the first and second optical channels.

Additional Example 114

The IR imaging system of any one of Additional Examples 85 to 113, wherein the processing unit is configured to subtract at least one reference image from the image data from the first and second optical channels.

Additional Example 115

The IR imaging system of any one of Additional Examples 85 to 114, wherein the processing unit is configured to detect edges in the image data from the first and second optical channels.

Additional Example 116

The IR imaging system of any one of Additional Examples 85 to 115, wherein the processing unit is configured to apply an edge detection mask to the image data from the first and second optical channels.

Additional Example 117

The IR imaging system of any one of Additional Examples 85 to 116, wherein the processing unit containing the processor is configured to determine whether obscuration is present that may degrade operation of the system based on the image data from the second camera system by:
receiving a first image from a first portion of the FPA;
receiving a second image from a second portion of the FPA;
transforming the first and second images into respective first and second gradient images;
determining that the gradient images have gradient values that exceed a first predetermined threshold;
providing the window obscuration alert after determining that the gradient values exceed the first predetermined threshold.

Additional Example 118

The IR imaging system of any one of Additional Examples 85 to 117, wherein the processing unit containing the processor is configured to determine whether obscuration is present that may degrade operation of the system based on the image data from the second camera system by:
receiving a first image from a first portion of the FPA;
receiving a second image from a second portion of the FPA;
transforming the first and second images into respective first and second gradient images;
determining that the first and second gradient images have a cross-correlation value that exceeds a first predetermined threshold; and
providing the window obscuration alert after determining that the cross-correlation value exceeds the first predetermined threshold.

Additional Example 119

The IR imaging system of any one of Additional Examples 85 to 118, wherein the processing unit containing the processor is configured to determine whether obscuration is present that may degrade operation of the system on the image data from the second camera system by:
receiving a first image from a first portion of the FPA;
receiving a second image from a second portion of the FPA;
transforming the first and second images into respective first and second gradient images;
determining that the gradient images have gradient values that exceed a first predetermined threshold;
cross-correlating the first and second gradient images;
determining that the first and second gradient images have a cross-correlation value that exceeds a second predetermined threshold; and
providing the window obscuration alert after determining that the gradient values exceed the first predetermined threshold and the cross-correlation value exceeds the second predetermined threshold.

Additional Example 120

The IR imaging system of any one of Additional Examples 85 to 119, wherein:

determining that the first and second gradient images have a cross-correlation value that exceeds a second predetermined threshold comprises:
  determining a plurality of cross-correlation values, each being associated with a different alignment of the first and second gradient images; and
  determining that at least one cross-correlation value in the plurality of cross-correlation values exceeds the second predetermined threshold.

Additional Example 121

The IR imaging system of any one of Additional Examples 85 to 120, wherein:
  determining that the first and second gradient images have a cross-correlation value that exceeds a second predetermined threshold comprises:
  determining a plurality of cross-correlation values, each being associated with a different alignment of the first and second gradient images;
  identifying a first cross-correlation value in the plurality of cross-correlation values;
  subtracting the first cross-correlation value from each of the cross-correlation values in the plurality of cross-correlation values;
  after subtracting the first cross-correlation value, identifying a second cross-correlation value in the plurality of cross-correlation values; and
  determining that the second cross-correlation value exceeds the second predetermined threshold.

Additional Example 122

The IR imaging system of any one of Additional Examples 85 to 121, wherein transforming the first and second images into respective first and second gradient images comprises applying a Sobel filter to the first and second images.

Additional Example 123

The IR imaging system of any one of Additional Examples 85 to 122, wherein transforming the first and second images into respective first and second gradient images comprises applying a Sobel filter to the first and second images and removing values from the gradient images that fall below a predetermined threshold.

Additional Example 124

The IR imaging system of any one of Additional Examples 85 to 123, wherein, prior to cross-correlating the first and second gradient images, the processing unit is configured to normalize each of the gradient images.

Additional Example 125

The IR imaging system of any one of Additional Examples 85 to 124, wherein, prior to cross-correlating the first and second gradient images, the processing unit is configured to normalize each of the gradient images by, for each gradient image, subtracting a median value from each gradient image and dividing each gradient image by a standard deviation value.

Additional Example 126

The IR imaging system of any one of Additional Examples 85 to 125, wherein, prior to cross-correlating the first and second gradient images, the processing unit is configured to normalize each of the gradient images.

Additional Example 127

The IR imaging system of any one of Additional Examples 85 to 126, wherein, prior to transforming the first and second images into respective first and second gradient images, the processing unit is configured to subtract a first reference image from the first image and subtract a second reference image from the second image.

Additional Example 128

The IR imaging system of any one of Additional Examples 85 to 127, wherein the second camera system is focused within 1 meter of the optical window.

Additional Example 129

The IR imaging system of any one of Additional Examples 85 to 128, wherein the second camera system is focused within 2 meters of the optical window.

Additional Example 130

The IR imaging system of any one of Additional Examples 85 to 129, wherein the second camera system is focused on the optical window.

Additional Example 131

The IR imaging system of any one of Additional Examples 85 to 130, wherein the first camera system is focused at a distance of at least 10 meters.

Additional Example 132

The IR imaging system of any one of Additional Examples 85 to 131, wherein the first camera system is focused at a distance of at least 20 meters.

Additional Example 133

The IR imaging system of any one of Additional Examples 85 to 132, wherein the first camera system is focused at a distance of at least 25 meters.

Additional Example 134

The IR imaging system of any one of Additional Examples 85 to 133, wherein the first and second camera systems have respective imaging lenses having respective focal lengths, and the focal length for the first camera is 2 times as large as the focal length for the second camera.

Additional Example 135

The IR imaging system of any one of Additional Examples 85 to 134, wherein the first and second camera systems have respective imaging lenses having respective focal lengths, and the focal length for the first camera is 5 times as large as the focal length for the second camera.

Additional Example 136

An Additional Example of a method of detecting obscuration of an optical window in an IR imaging system, the IR imaging system comprising processing circuitry and a plurality of spatially and spectrally distinct optical channels, each optical channel including a set of lenses that focus incident IR light on a respective portion of an optical detector system, the method comprising:
- with the processing circuitry, receiving a first image from a first optical channel in the plurality of optical channels;
- with the processing circuitry, receiving a second image from a second optical channel in the plurality of optical channels; and
- with the processing circuitry, analyzing the first and second images to detect obscuration that may degrade operation of the system.

Additional Example 137

The method of Additional Example 136, wherein the first and second images are in focus at the depth of the optical window.

Additional Example 138

The method of any one of Additional Examples 136 to 137, wherein analyzing the first and second images comprises, with the processing circuitry, comparing the first and second images to identify obscuration that may degrade operation of the system.

Additional Example 139

The method of any one of Additional Examples 136 to 138, wherein analyzing the first and second images comprises, with the processing circuitry, comparing the first and second images and using differences between the first and second images caused by parallax to determine whether obscuration is present that may degrade operation of the system.

Additional Example 140

The method of any one of Additional Examples 136 to 139, wherein analyzing the first and second images comprises evaluating how much of the images are in focus to detect obscuration that may degrade operation of the system.

Additional Example 141

The method of any one of Additional Examples 136 to 140, wherein analyzing the first and second images comprises evaluating the contrast of the images to detect obscuration that may degrade operation of the system.

Additional Example 142

The method of any one of Additional Examples 136 to 141, further comprising performing edge enhancement.

Additional Example 143

The method of any one of Additional Examples 136 to 142, further comprising performing edge detection.

Additional Example 144

The method of any one of Additional Examples 136 to 143, further comprising normalizing image data.

Additional Example 145

The method of any one of Additional Examples 136 to 144, wherein the normalizing comprises scaling image data.

Additional Example 146

The method of any one of Additional Examples 136 to 145, wherein the normalizing comprises subtracting from image data.

Additional Example 147

The method of any one of Additional Examples 136 to 146, wherein analyzing the first and second images comprises performing a correlation of the first and second images.

Additional Example 148

The method of any one of Additional Examples 136 to 147, wherein analyzing the first and second images comprises comparing image data from the first and second images at a plurality of offsets along the given direction to detect obscuration that may degrade operation of the system.

Additional Example 149

The method of any one of Additional Examples 136 to 148, wherein analyzing the first and second images comprises evaluating whether image data exceeds a threshold to determine obscuration that may degrade operation of the system.

Additional Example 150

The method of any one of Additional Examples 136 to 149, wherein analyzing the first and second images comprises, with the processing circuitry, applying an unsharp mask to the first and second images.

Additional Example 151

The method of any one of Additional Examples 136 to 150, further comprising:
- with the processing circuitry, subtracting a first reference image from the first image and subtracting a second reference image from the second image.

Additional Example 152

The method of any one of Additional Examples 136 to 151, further comprising:
- with the processing circuitry, detecting edges in the first and second images.

Additional Example 153

The method of any one of Additional Examples 136 to 152, further comprising:
- with the processing circuitry, applying a Sobel filter to the first and second images.

Additional Example 154

The method of any one of Additional Examples 136 to 153, further comprising:

with the processing circuitry, applying a Sobel filter to the first and second images to create respective first and second gradient images.

Additional Example 155

The method of any one of Additional Examples 136 to 154, further comprising:
with the processing circuitry, normalizing the first and second gradient images.

Additional Example 156

The method of any one of Additional Examples 136 to 155, further comprising:
with the processing circuitry, cross-correlating the first and second gradient images.

Additional Example 157

The method of any one of Additional Examples 136 to 156, further comprising:
with the processing circuitry, determining that at least one cross-correlation between the first and second gradient images exceeds a first window obscuration threshold and that the first and second gradient images exceed a second window obscuration threshold and, in response, providing an alert that the optical window is obscured.

Additional Example 158

The method of any one of Additional Examples 136 to 157, wherein operation of the system comprises detecting a target species based on image data from said plurality of spatially and spectrally distinct optical channels.

Additional Example 159

The method of any one of Additional Examples 136 to 158, further comprising performing spectral analysis to detect said target species.

Additional Example 160

The method of any one of Additional Examples 136 to 159, further comprising adjusting image data from the plurality of optical channels to compensate for effects of attenuation due to the window being obscured.

Additional Example 161

The method of any one of Additional Examples 136 to 160, further comprising de-emphasizing one or more frames of image data from the plurality of optical channels in the determination of the presence of a target species.

Additional Example 162

The method of any one of Additional Examples 136 to 161, further comprising sending an alert when the window is obscured.

Additional Example 163

The IR imaging system of any one of Additional Examples 1 to 135, wherein said IR imaging system is configured such that operation of the system includes performing spectral analysis on images to detect target species.

Any of Additional Examples 1 to 163 can include any of the features described above (for example, any of the features in Examples 1 to 163).

VII. Additional Considerations

Each of the embodiments disclosed herein can be used to estimate various characteristics of gases present in a gas leak imaged by the infrared imaging systems disclosed herein.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In the drawings like numbers are used to represent the same or similar elements wherever possible. The depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The features recited in claims appended to this disclosure are intended to be assessed in light of the disclosure as a whole.

At least some elements of a device of the invention can be controlled—and at least some steps of a method of the invention can be effectuated, in operation—with a programmable processor governed by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While examples of embodiments of the system and method of the invention have been discussed in reference to the gas-cloud detection, monitoring, and quantification (including but not limited to greenhouse gases such as Carbon Dioxide, Carbon Monoxide, Nitrogen Oxide as well as hydrocarbon gases such as Methane, Ethane, Propane, n-Butane, iso-Butane, n-Pentane, iso-Pentane, neo-Pentane, Hydrogen Sulfide, Sulfur Hexafluoride, Ammonia, Benzene, p- and m-Xylene, Vinyl chloride, Toluene, Propylene oxide, Propylene, Methanol, Hydrazine, Ethanol, 1,2-dichloroethane, 1,1-dichloroethane, Dichlorobenzene, Chlorobenzene, to name just a few), embodiments of the invention can be readily adapted for other chemical detection applications. For example, detection of liquid and solid chemical spills, biological weapons, tracking targets based on their chemical composition, identification of satellites and space debris, opthalmological imaging, microscopy and cellular imaging, endoscopy, mold detection, fire and flame detection, and pesticide detection are within the scope of the invention.

As used herein, a phrase referring to "at least one of" a list of items refers to any combination of those items, including single members. As an example, "at least one of: a, b, or c" is intended to cover: a, b, c, a-b, a-c, b-c, and a-b-c.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above also may be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. An infrared (IR) imaging system comprising:
a housing;
an optical window disposed on the housing;
an optical detector system disposed within the housing; and
a plurality of spatially and spectrally distinct optical channels that transfer incident IR radiation from the optical window to the optical detector system, wherein a first optical channel out of the plurality of optical channels has a focus distance that is closer to the optical window than at least some of the other optical channels of the plurality of optical channels to detect obscuration that may degrade operation of the system.

2. The IR imaging system of claim 1, wherein the first optical channel out of the plurality of optical channels has a focus less than 2 meters and other optical channels of the plurality of optical channels have a focus of greater than 10 meters.

3. The IR imaging system of claim 1, wherein at least some of the other optical channels of the plurality of optical channels have focus distances at least 5 meters greater than the focus distance of the first optical channel.

4. The IR imaging system of claim 1, wherein the first optical channel is in focus at the optical window to detect obscuration that may degrade operation of the system.

5. The IR imaging system of claim 1, further comprising:
a processing unit comprising processing electronics configured to process image data from the first optical channel to detect obscuration that may degrade operation of the system.

6. The IR imaging system of claim 5, wherein:
a second optical channel out of the plurality of optical channels is in focus at the optical window; and
the processing unit is configured to compare image data from the first and second optical channels to detect obscuration that may degrade operation of the system.

7. The IR imaging system of claim 1, wherein the window is embedded in the housing or is in an opening in the housing.

8. An infrared (IR) imaging system for imaging a target species in a scene, the IR imaging system comprising:
an optical window;
a first camera system configured to acquire infrared image data of the scene through the optical window;
a second camera system focused closer to the optical window than the first camera system; and
a processing unit containing a processor configured to:
analyze the infrared image data from the first camera system to detect the target species based on the infrared image data; and
analyze image data from the second camera system to determine whether obscuration is present that may degrade operation of the system based on the image data from the second camera system.

9. The IR imaging system of claim 8, wherein said processing unit is configured to provide a window obscuration alert after determining that obscuration is present that may degrade operation of the system.

10. The IR imaging system of claim 8, wherein said processing unit is configured to compensate for effects of attenuation due to obscuration when analyzing the infrared image data to detect the target species.

11. The IR imaging system of claim 8, wherein the processing unit containing the processor is configured to determine whether obscuration is present that may degrade operation of the system based on the image data from the second camera system by:
receiving a first image from a first portion of the second camera system;
receiving a second image from a second portion of the second camera system;
transforming the first and second images into respective first and second gradient images;
determining that the first and second gradient images have a cross-correlation value that exceeds a first predetermined threshold; and
providing a window obscuration alert after determining that the cross-correlation value exceeds the first predetermined threshold.

12. A method of detecting obscuration of an optical window in an IR imaging system, the IR imaging system comprising processing circuitry and a plurality of spatially and spectrally distinct optical channels, each optical channel including a set of lenses that focus incident IR light on a respective portion of an optical detector system, the method comprising:
with the processing circuitry, receiving a first image from a first optical channel in the plurality of optical channels;
with the processing circuitry, receiving a second image from a second optical channel in the plurality of optical channels; and
with the processing circuitry, analyzing the first and second images to detect obscuration that may degrade operation of the system, said analyzing comprising:
creating first and second gradient images from the first and second images, respectively;
cross-correlating the first and second gradient images; and
determining that at least one cross-correlation between the first and second gradient images exceeds a first window obscuration threshold and that the first and second gradient images exceed a second window obscuration threshold and, in response, providing an alert that the optical window is obscured.

13. The method of claim 12, wherein analyzing the first and second images comprises, with the processing circuitry, comparing the first and second images to identify obscuration that may degrade operation of the system.

14. The method of claim 12, wherein analyzing the first and second images comprises, with the processing circuitry, comparing the first and second images and using differences between the first and second images caused by parallax to determine whether obscuration is present that may degrade operation of the system.

15. The method of claim 12, wherein analyzing the first and second images comprises evaluating how much of the images are in focus to detect obscuration that may degrade operation of the system.

16. The method of claim 12, wherein analyzing the first and second images comprises evaluating contrast levels of the images to detect obscuration that may degrade operation of the system.

17. The method of claim 12, further comprising adjusting image data from the plurality of optical channels to compensate for effects of attenuation due to obscuration.

18. The method of claim 12, wherein analyzing the first and second images comprises evaluating whether image data exceeds a threshold to determine whether obscuration is present that may degrade operation of the system.

19. The method of claim 12, further comprising detecting a target species based on image data from said plurality of spatially and spectrally distinct optical channels.

* * * * *